(12) United States Patent
Arnaout

(10) Patent No.: US 11,685,717 B2
(45) Date of Patent: Jun. 27, 2023

(54) POLYPEPTIDE INTEGRIN ANTAGONISTS

(71) Applicant: The General Hospital Corporation, Boston, MA (US)

(72) Inventor: M. Amin Arnaout, Chestnut Hill, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 17/266,339

(22) PCT Filed: Aug. 8, 2019

(86) PCT No.: PCT/US2019/045762
§ 371 (c)(1),
(2) Date: Feb. 5, 2021

(87) PCT Pub. No.: WO2020/033731
PCT Pub. Date: Feb. 13, 2020

(65) Prior Publication Data
US 2022/0356217 A1  Nov. 10, 2022

Related U.S. Application Data

(60) Provisional application No. 62/715,860, filed on Aug. 8, 2018, provisional application No. 62/757,126, filed on Nov. 7, 2018, provisional application No. 62/786,804, filed on Dec. 31, 2018.

(51) Int. Cl.
| | | |
|---|---|---|
| *C07D 211/22* | (2006.01) | |
| *A61P 7/04* | (2006.01) | |
| *A61K 45/06* | (2006.01) | |
| *C07K 14/70* | (2006.01) | |
| *C07K 14/705* | (2006.01) | |
| *C07K 14/47* | (2006.01) | |
| *A61K 38/00* | (2006.01) | |

(52) U.S. Cl.
CPC ............ *C07D 211/22* (2013.01); *A61K 45/06* (2013.01); *A61P 7/04* (2018.01); *C07K 14/4703* (2013.01); *C07K 14/70546* (2013.01); *A61K 38/00* (2013.01); *C07B 2200/13* (2013.01)

(58) Field of Classification Search
CPC ......... C07D 211/22; A61P 7/04; A61K 45/06; C07K 14/70546
See application file for complete search history.

(56) References Cited

U.S. PATENT DOCUMENTS

2017/0044236 A1* 2/2017 Arnaout ................. C07K 14/47

FOREIGN PATENT DOCUMENTS

| WO | WO 2013/185027 | 12/2013 |
| WO | WO 2015/103643 | 7/2015 |

OTHER PUBLICATIONS

Adams et al., "PHENIX: a comprehensive Python-based system for macromolecular structure solution," Acta Crystallogr. D. Biol. Crystallogr., Feb. 2010, 66(Pt 2):213-221.
Altschul et al., "Gapped BLAST and PSI-BLAST: a new generation of protein database search programs," Nucleic Acids Res., Sep. 1997, 25(17):3389-3402.
Andre et al., "CD40L stabilizes arterial thrombi by a beta3 integrin-dependent mechanism," Nat. Med., Mar. 2002, 8(3)247-252.
Benjamin et al., "Heart Disease and Stroke Statistics—2017 Update: A Report From the American Heart Association," Circulation, 2017, 135:e146-e603, 459 pages.
Bosch et al., "Platelet glycoprotein IIb/IIIa blockers during percutaneous coronary intervention and as the initial medical treatment of non-ST segment elevation acute coronary syndromes," Cochrane Database Syst Rev, Nov. 2013, 8(1):CD002130, 191 pages.
Bougie et al., "Acute thrombocytopenia after treatment with tirofiban or eptifibatide is associated with antibodies specific for ligand-occupied GPIIb/IIIa," Blood, Sep. 2002, 100(6):2071-2076.
Celi et al., "Thrombus formation: direct real-time observation and digital analysis of thrombus assembly in a living mouse by confocal and widefield intravital microscopy," J Thromb. Haemost., Jan. 2003, 1:60-68.
Coller & Shattil, "The GPIIb/IIIa (integrin alphaIIbbeta3) odyssey: a technology-driven saga of a receptor with twists, turns, and even a bend," Blood, Oct. 2008, 112(8):3011-3025.
Cox et al., "Integrins as therapeutic targets: lessons and opportunities," Nat Rev Drug Discov, Oct. 2010, 9(10):804-820.
Donner et al., "Platelets contribute to amyloid-β aggregation in cerebral vessels through integrin αIIbβ3-induced outside-in signaling and clusterin release," Sci. Signal., May 2016, 9(429):ra52, 17 pages.
Emsley et al., "Features and development of Coot," Acta Clystallogr. D. Biol. Crystallogr., Apr. 2010, D66(Pt 4):486-501.
Engebraaten et al., "Inhibition of In Vivo Tumour Growth by the Blocking of Host αvβ3 and αIIbβ3 Integrins," Anticancer Res., Jan. 2009, 29(1):131-137.
Franchi and Angiolillo, "Novel antiplatelet agents in acute coronary syndrome," Nat. Rev. Cardiol., Jan. 2015, 12(1):30-47, 18 pages.
Fuentes et al., "A chimeric platelet-targeted urokinase prodrug selectively blocks new thrombus formation," J Clin. Invest., Feb. 2016, 126(2):483-494.
Gerber et al., "Integrin-modulating therapy prevents fibrosis and autoimmunity in mouse models of scleroderma," Nature, Nov. 2013, 503(7474):126-130, 7 pages.
Gomes et al., "Breast adenocarcinoma cell adhesion to the vascular subendothelium in whole blood and under flow conditions: effects of alphavbeta3 and alphaIIbbeta3 antagonists," Clin. Exp. Metastasis, Jan. 2004, 21(6)553-561.

(Continued)

*Primary Examiner* — Amber D Steele
(74) *Attorney, Agent, or Firm* — Fish & Richardson P.C.

(57) ABSTRACT

The present application relates to polypeptides which are integrin antagonists. Methods of preparing the integrin antagonists and methods of treating diseases and disorders associated with abnormal levels and/or expression of one or more integrins are also provided.

24 Claims, 36 Drawing Sheets
Specification includes a Sequence Listing.

(56) References Cited

OTHER PUBLICATIONS

Greene et al., "Towards a standardization of the murine tail bleeding model," J. Thromb. Haemost., 2010, 8:2820-2822.
Haling et al., "Talin-dependent integrin activation is required for fibrin clot retraction by platelets," Blood, 2011, 117(5):1719-1722.
Hamaguchi et al., "Spreading of platelets on fibrin is mediated by the amino terminus of the beta chain including peptide beta 15-42," Blood, May 1993, 81(9):2348-2356.
Hantgan & Mousa, "Inhibition of platelet-mediated clot retraction by integrin antagonists," Thromb. Res., Mar. 1998, 89(6):271-279.
Hohmann et al., "Delayed targeting of CD39 to activated platelet GPIIb/IIIa via a single-chain antibody: breaking the link between antithrombotic potency and bleeding?," Blood, Apr. 2013, 121(16):3067-3075.
Holmes et al., "Variable responses to inhibition of fibrinogen binding induced by tirofiban and eptifibatide in blood from healthy subjects," Am. J. Cardiol., Jul. 1999, 84(2):203-207.
International Preliminary Report on Patentability in International Appln. No. PCT/US2019/045762, dated Feb. 9, 2021, 7 pages.
International Search Report and Written Opinion in International Appln. No. PCT/US2019/045762, dated Jan. 16, 2020, 14 pages.
Invitiation to Pay Additional Fees and, Where Applicable, Protest Fee in International Appln. No. PCT/US2019/045762, dated Nov. 4, 2019, 2 pages.
Jenkins et al., "Tyrosine Phosphorylation of the β3 Cytoplasmic Domain Mediates Integrin-Cytoskeletal Interactions*," J Biol. Chem., May 1998, 273(22):13878-13885.
Klinkhardt et al., "Differential in Vitro Effects of the Platelet Glycoprotein IIb/IIIa Inhibitors abixicimab or SR121566A on Platelet Aggregation, Fibrinogen Binding and Platelet Secretory Parameters," Thromb. Res., Feb. 2000, 97(4):201-207.
Lavergne et al., "Platelet Integrins in Tumor Metastasis: Do They Represent a Therapeutic Target?," Cancers (Basel), Sep. 2017, 9(10):133, 17 pages.
Léon et al., "Megakaryocyte-restricted MYH9 inactivation dramatically affects hemostasis while preserving platelet aggregation and secretion," Blood, Nov. 2007, 110:3183-3191.
Ley et al., "Integrin-based therapeutics: biologicalbasis, clinical use and new drugs," Nat. Rev. Drug. Discov., Mar. 2016, 15(3):173-183, 11 pages.
Li et al., "RUC-4: A Novel αIIbβ3 Antagonist for Prehospital Therapy of Myocardial Infarctio," Arterioscler. Thromb. Vase. Biol., Aug. 2014, 34(10):2321-2329, 10 pages.
Litvinov et al., "The Platelet Integrin αIIbβ3 Differentially Interacts with Fibrin Versus Fibrinogen," J Biol. Chem., Apr. 2016, 291(15)7858-7867.
Liu et al., "The Roles of Platelet GPIIb/IIIa and αvβ3 Integrins during HeLa Cells Adhesion, Migration, and Invasion to Monolayer Endothelium under Static and Dynamic Shear Flow," J Biomed Biotechnol., 2009, 2009:829243, 10 pages.
Magallon et al., "Humanized Mouse Model of Thrombosis is Predictive of the Clinical Efficacy of Antiplatelet Agents," Circulation, Jan. 2011, 123:319-326.
Maile et al., "A Monoclonal Antibody Against αVβ3 Integrin Inhibits Development of Atherosclerotic Lesions in Diabetic Pigs," Sci. Transl.Med., Feb. 2010, 2(18):18ra11, 9 pages.
Massberg et al., "Effects of 2 different antiplatelet regimens with abciximab or tirofiban on platelet function in patients undergoing coronary stenting," Am. Heart J., Nov. 2003, 146(5):E19, 9 pages.
McFadyen and Peter, "Novel Antithrombotic Drugs on the Horizon: The Ultimate Promise to Prevent Clotting While Avoiding Bleeding," Circ. Res., Oct. 2017, 121(10):1133-1135, 3 pages.
Miller et al., "Small-molecule inhibitors of integrin α2β1 that prevent pathological thrombus formation via an allosteric mechanism," Proc. Natl. Acad Sci. US.A., Jan. 2009, 106(3):719-724.
Moore et al., "Engineered knottin peptide enables noninvasive optical imaging of intracranial medulloblastoma," PNAS, Sep. 2013, 110(36):14598-14603.

Morrow et al., "Vorapaxar in the Secondary Prevention of Atherothrombotic Events," N Engl. J Med, Apr. 2012, 366:1404-1413, 10 pages.
Mousa et al., "Comparative In Vitro Efficacy of Different Platelet Glycoprotein IIb/IIIa Antagonists on Platelet-Mediated Clot Strength Induced by Tissue Factor With Use of Thromboelastography," Arterioscler. Thromb. Vase. Biol., Apr. 2000, 20:1162-1167, 8 pages.
Mukai et al., "Reassignment of a rare sense codon to a non-canonical amino acid in *Escherichia coli*," Nucleic Acids Res., Sep. 2015, 43(16):8111-22.
Ndrepepa et al., "Correlates of poor outcome among patients with bleeding after coronary interventions," Coron. Artery Dis., Sep. 2014, 25(6):456-462.
Neyman et al., "Analysis of the spatial and temporal characteristics of platelet-delivered factor VIII-based clots," Blood, 2008, 112(4):1101-1108.
Osdoit and Rosa, "Fibrin clot retraction by human platelets correlates with alpha(IIb)beta(3) integrin-dependent protein tyrosine dephosphorylation," J Biol. Chem., Mar. 2001, 276(9):6703-6710.
Otwinowski and Minor, "Processing of X-ray diffraction data collected in oscillation mode," Methods Enzymol., 1997, 276:307-326.
Podolnikova et al., "The interaction of integrin αIIbβ3 with fibrin occurs through multiple binding sites in the αIIb β-propeller domain," J Biol. Chem., 2013, 289(4):2371-2383.
Ponticelli et al., "Renal allograft thrombosis," Nephrol. Dial. Transplant, May 2009, 24(5):1388-1393.
Quencer et al., "Hemodialysis access thrombosis," Cardiovasc Diagn Ther, Dec. 2017, 7(Suppl 3):S299-S308.
Raab-Westphal et al., "Integrins as Therapeutic Targets: Successes and Cancers," Cancers (Basel), Aug. 2017, 9(9):110, 28 pages.
Richards et al., "Engineered fibronectin type III domain with a RGDWXE sequence binds with enhanced affinity and specificity to human alphavbeta3 integrin," J Mol. Biol., Mar. 2003, 326(5):1475-1488.
Savage and Ruggeri, "Selective recognition of adhesive sites in surface-bound fibrinogen by glycoprotein IIb-IIIa on nonactivated platelets," J Biol. Chem., Jun. 1991, 266(17):11227-11233.
Schrör and Weber, "Comparative pharmacology of GP IIb/IIIa antagonists," J Thromb. Thrombolysis, Apr. 2003, 15(2):71-80.
Sheldrake and Patterson, "Function and Antagonism of β," Curr. Cancer Drug Targets, 2009, 9(4):519-540.
Shen et al., "A directional switch of integrin signalling and a new anti-thrombotic strategy," Nature, Nov. 2013, 503(7474):131-135, 17 pages.
Silverman et al., "Engineered cystine-knot peptides that bind alpha(v)beta(3) integrin with antibody-like affinities," J Mol. Biol., Nov. 2008, 385(4):1064-1075.
Tam et al., "Abciximab (ReoPro, Chimeric 7E3 Fab) Demonstrates Equivalent Affinity and Functional Blockade of Glycoprotein IIb/IIIa and αvβ3 Integrins," Circulation, Sep. 1998, 98:1085-1091.
The Admiral Investigators, "Three-year duration of benefit from abciximab in patients receiving stents for acute myocardial infarction in the randomized double-blind Admiral study," Eur. Heart J, Dec. 2005, 26(23):2520-2523.
Topol et al., "Multi-year follow-up of abciximab therapy in three randomized, placebo-controlled trials of percutaneous coronary revascularization," Am. J Med, Jul. 2002, 113(1):1-6.
Tricoci et al., "Thrombin-Receptor Antagonist Vorapaxar in Acute Coronary Syndromes," N Engl. J Med, Jan. 2012, 366(1):20-33.
Trikha et al., "Multiple roles for platelet GPIIb/IIIa and alphavbeta3 integrins in tumor growth, angiogenesis, and metastasis," Cancer Res., May 2002, 62(10):2824-2833.
Tsai et al., "Increased Risk of Bleeding in Patients on Clopidogrel Therapy After Drug-Eluting Stents Implantation," Circ. Cardiovasc. Interv., May 2010, 3230-235, 7 pages.
Tucker et al., "Clot Reaction," Methods Mol. Biol., 2012, 788:101-107.
Tutwiler et al., "Interplay of Platelet Contractility and Elasticity of Fibrin/Erythrocytes in Blood Clot Retraction," Biophys. J, Feb. 2017, 112(4):714-723.
Ungerer et al., "Novel antiplatelet drug revacept (Dimeric Glycoprotein VI-Fc) specifically and efficiently inhibited collagen-induced plate-

(56) References Cited

OTHER PUBLICATIONS let aggregation without affecting general hemostasis in humans," Circulation, May 2011, 123(17):1891-1899.

Van Agthoven et al., "Structural basis for pure antagonism of integrin αVβ3 by a high-affinity form of fibronectin," Nat. Struct. Mol. Biol., Apr. 2014, 21(4):383-388.

Wallentin et al., "Ticagrelor versus clopidogrel in patients with acute coronary syndromes," N Engl. J Med, Sep. 2009, 361(11):1045-1057.

Wang et al., "Leukocyte integrin Mac-1 regulates thrombosis via interaction with platelet GPIbα," Nat. Commun., May 2017, 8:15559, 15 pages.

Wolf et al., "Binding of CD40L to Mac-1's I-Domain Involves the EQLKKSKTL Motif and Mediates Leukocyte Recruitment and Atherosclerosis—But Does Not Affect Immunity and Thrombosis in Mice," Circ. Res., Oct. 2011, 109:1269-1279.

Xiong et al., "Crystal structure of the extracellular segment of integrin alpha Vbeta3," Science, Oct. 2001, 294(5541):339-345.

Zheng et al., "Discovery and antiplatelet activity of a selective PI3Kβ inhibitor (MIPS-9922)," Eur. J Med Chem., Oct. 2016, 122:339-351.

Zhu et al., "Structure-Guided Design of a High-Affinity Platelet Integrin αIIbβ3 Receptor Antagonist That Disrupts Mg2+ Binding to the MIDAS," Sci. Transl. Med., Mar. 2012, 4(125):125ra132, 13 pages.

Estevez et al., "Targeting integrin and integrin signaling in treating thrombosis," Translational Sciences, Jan. 2015, 35(1):24-29, 7 pages.

Extended European Search Report in European Appln. No. 19848229.1, dated Aug. 25, 2022, 10 pages.

* cited by examiner

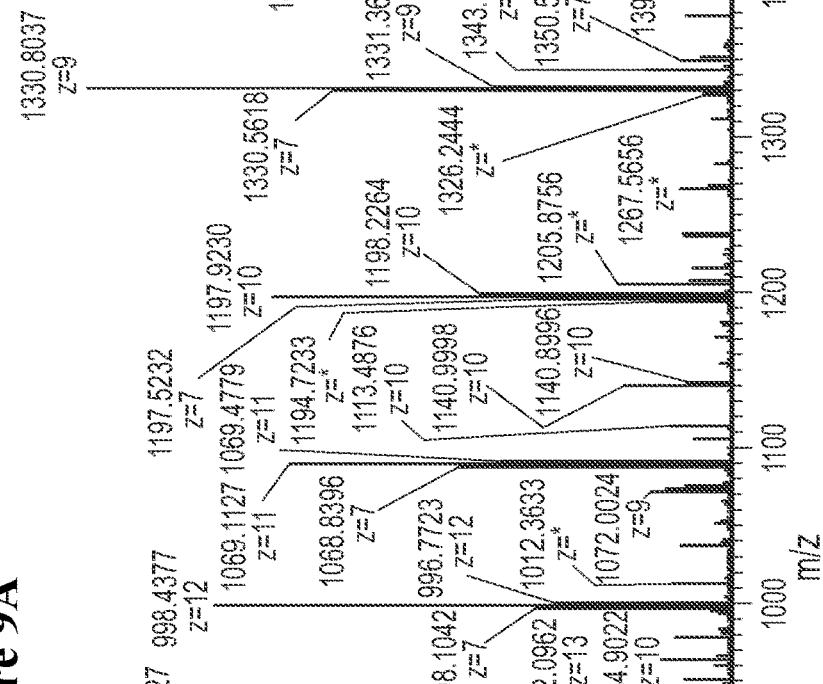
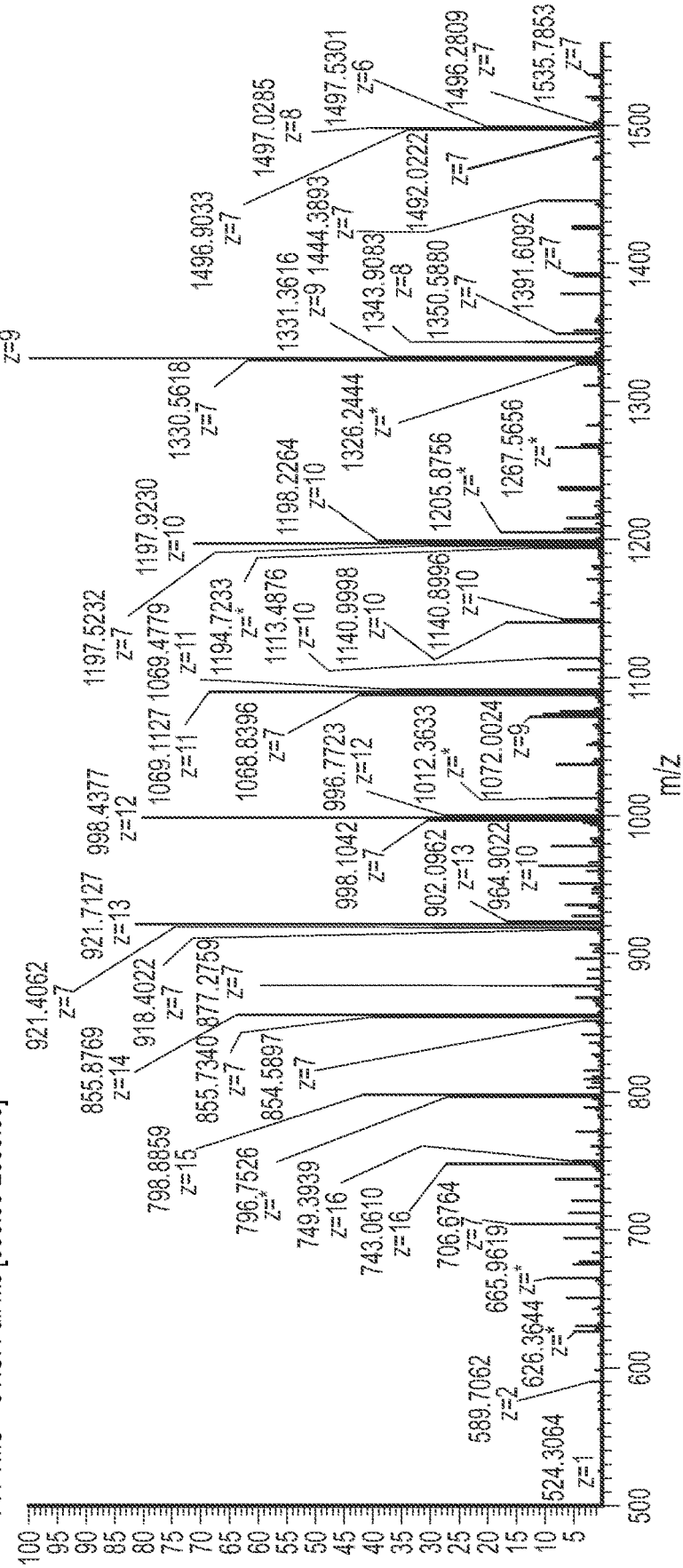
Figure 9A
Figure 9B

| Sample : Hr10 | | | |
|---|---|---|---|
| | m/z | Charge | mass |
| m/z_largest | 1497.0285 | 8 | 11968.228 |
| m/z_2 | 1330.8037 | 9 | 11968.2333 |
| m/z_3 | 1197.9230 | 10 | 11969.23 |
| m/z_4 | 1069.1127 | 11 | 11969.2397 |
| m/z_5 | 998.4377 | 12 | 11969.2524 |
| m/z_6 | 921.7127 | 13 | 11969.2651 |
| m/z_7 | 855.8769 | 14 | 11968.2766 |
| m/z_8 | 798.8859 | 15 | 11968.2885 |
| m/z_9 | 749.0610 | 16 | 11969.296 |
| Average mass | | SO | |
| 11,968.8122 | | 0.528 | |

Figure 9C

| Agonist | Inhibitor | Mean IC$_{50}$ (nM) | S.E. | P value |
|---|---|---|---|---|
| Collagen (1µg/ml) | Hr10 | 75.5 | 23.3 | 0.7 |
|  | Eptifibatide | 70.9 | 12.1 |  |
| ADP (20µM) | Hr10 | 62.5 | 19.2 | 0.0024 |
|  | Eptifibatide | 26.3 | 2.8 |  |
| TRAP (10µM) | Hr10 | 51.0 | 12.3 | 0.023 |
|  | Eptifibatide | 28.0 | 3.1 |  |

Figure 11D

POLYPEPTIDE INTEGRIN ANTAGONISTS

CROSS-REFERENCE TO RELATED APPLICATIONS

This application is a 371 National Phase of International Application No. PCT/US2019/045762, filed Aug. 8, 2019, which claims the benefit of U.S. Provisional Application Serial Nos. 62/715,860, filed Aug. 8, 2018; 62/757,126, filed Nov. 7, 2018; and 62/786,804, filed Dec. 31, 2018, the disclosure of each of which is incorporated herein by reference in its entirety.

FEDERALLY SPONSORED RESEARCH OR DEVELOPMENT

This invention was made with Government support under Grant No R01 DK088327-01, awarded by the National Institute of Diabetes and Digestive and Kidney Diseases. The Government has certain rights in the invention.

SEQUENCE LISTING

This application contains a Sequence Listing that has been submitted electronically as an ASCII text file named "29539-0423US1_SL_ST25.txt." The ASCII text file, created on Aug. 11, 2022, is 22,920 bytes in size. The material in the ASCII text file is hereby incorporated by reference in its entirety.

TECHNICAL FIELD

This present application relates to a novel class of pure integrin antagonists and methods of using the same.

BACKGROUND

Integrins are a/s heterodimeric cell adhesion receptors of metazoa, consisting of a bilobular head and two legs or tails that both span the plasma membrane. Integrins are unusual receptors, as they often exist on the cell surface in an inactive state (e.g., unable to engage a physiologic ligand). This is an important feature of integrin biology; for example, it allows patrolling blood platelets and immune cells to circulate with minimal aggregation or interaction with vessel walls. Physiological stimuli (e.g., chemokines), acting through the short integrin cytoplasmic tails, induce allosteric changes in the ectodomain required for extracellular physiologic ligand binding (i.e. "inside-out" signaling). Binding of extracellular ligands can induce "outside-in" signaling by initiating additional structural rearrangements, detectable in the isolated ectodomain using biophysical assays, and in integrins on the cell surface by their expression of novel epitopes (Ligand-induced binding sites, LIBS) including the epitopes of monoclonal antibodies (mAbs) AP5, LIBS-1 and LIBS-6. These ligand-induced structural rearrangements can trigger cell spreading, for example via connections established between integrin cytoplasmic tails and actin. Disruption of these regulatory processes can influence the pathogenesis of many diseases.

SUMMARY

The present application provides, inter alia, a polypeptide, wherein the polypeptide has at least 95% sequence identity to a polypeptide selected from the group consisting of:

(SEQ ID NO: 1)
$R^1$-SDVPRDLEVVAATPTSLLISWDAPAVTVRYYRITYGETGGNSPVQEFT

VPGSKSTATISGLKPGVDYTITVYAVTP(Har)GDWNEGGPISINYRT-$R^2$;

(SEQ ID NO: 2)
$R^1$-SDVPRDLEVVAATPTSLLISWDAPAVTVRYYRITYGETGGNSPVQEFT

VPGSKSTATISGLKPGVDYTITVYAVTPKGDWNEGGPISINYRT-$R^2$;; and (SEQ ID NO: 3)
$R^1$-SDVPRDLEVVAATPTSLLISWDAPAVTVRYYRITYGETGGNSPVQEFT

VPGSKSTATISGLKPGVDYTITVYAVTPRGDWNEGGPISINYRT-$R^2$;

wherein:
$R^1$ is absent or a histidine tag;
$R^2$ is absent or GKKGK (SEQ ID NO: 6).

In some embodiments, the polypeptide has at least 99% sequence identity to a polypeptide selected from the group consisting of:
$R^1$-SDVPRDLEVVAATPTSLLISWDAPAVTVRYYRI-TYGETGGNSPV (SEQ ID NO: 1)
$R^1$-SDVPRDLEVVAATPTSLLISWDAPAVTVRYYRITYGETGGNSPVQEFT VPGSKSTATISGLKPGVDYTITVYAVTP(Har)GDWNEGGPISINYRT-$R^2$;

(SEQ ID NO: 2)
$R^1$-SDVPRDLEVVAATPTSLLISWDAPAVTVRYYRITYGETGGNSPVQEFT

VPGSKSTATISGLKPGVDYTITVYAVTPKGDWNEGGPISINYRT-$R^2$;; and (SEQ ID NO: 3)
$R^1$-SDVPRDLEVVAATPTSLLISWDAPAVTVRYYRITYGETGGNSPVQEFT

VPGSKSTATISGLKPGVDYTITVYAVTPRGDWNEGGPISINYRT-$R^2$.

In some embodiments, $R^1$ is a histidine tag. In some embodiments, the histidine tag comprises a polypeptide having at least 95% sequence identity to a polypeptide having the sequence ASHHHHHHLVPRGS (SEQ ID NO: 5).

In some embodiments, the histidine tag comprises a fluorescent small molecule. In some embodiments, the fluorescent small molecule is Alexa Fluor 647. In some embodiments, $R^1$ is absent.

In some embodiments, $R^2$ is GKKGK (SEQ ID NO: 6). In some embodiments, $R^2$ is absent.

In some embodiments, the polypeptide has at least 95% sequence identity to a polypeptide which is:

(SEQ ID NO: 7)
SDVPRDLEVVAATPTSLLISWDAPAVTVRYYRITYGETGGNSPVQEFTVPG

SKST ATISGLKPGVDYTITVYAVTP(Har)GDWNEGGPISINYRT.

In some embodiments, the polypeptide has at least 99% sequence identity to a polypeptide which is:

(SEQ ID NO: 7)
SDVPRDLEVVAATPTSLLISWDAPAVTVRYYRITYGETGGNSPVQEFTVPG

SKST ATISGLKPGVDYTITVYAVTP(Har)GDWNEGGPISINYRT.

In some embodiments, the polypeptide is:

(SEQ ID NO: 7)
SDVPRDLEVVAATPTSLLISWDAPAVTVRYYRITYGETGGNSPVQEFTVPG

SKSTATISGLKPGVDYTITVYAVTP(Har)GDWNEGGPISINYRT.

In some embodiments, the polypeptide has at least 95% sequence identity to a polypeptide which is:

(SEQ ID NO: 8)
ASHHHHHHLVPRGSSDVPRDLEVVAATPTSLLISWDAPAVTVRYYRITYGE

TGGNSPVQEFTVPGSKSTATISGLKPGVDYTITVYAVTP(Har)GDWNEGG

PISINYRT.

In some embodiments, the polypeptide has at least 99% sequence identity to a polypeptide which is:

(SEQ ID NO: 8)
ASHHHHHHLVPRGSSDVPRDLEVVAATPTSLLISWDAPAVTVRYYRITYGE

TGGNSPVQEFTVPGSKSTATISGLKPGVDYTITVYAVTP(Har)GDWNEGG

PISINYRT.

In some embodiments, the polypeptide is:

(SEQ ID NO: 8)
ASHHHHHHLVPRGSSDVPRDLEVVAATPTSLLISWDAPAVTVRYYRITYGE

TGGNSPVQEFTVPGSKSTATISGLKPGVDYTITVYAVTP(Har)GDWNEGG

PISINYRT.

In some embodiments, the polypeptide has at least 95% sequence identity to a polypeptide which is:

(SEQ ID NO: 9)
ASHHHHHHLVPRGSSDVPRDLEVVAATPTSLLISWDAPAVTVRYYRITYGE

TGGNSPVQEFTVPGSKSTATISGLKPGVDYTITVYAVTP(Har)GDWNEGG

PISINYRTGKKGK.

In some embodiments, the polypeptide has at least 99% sequence identity to a polypeptide which is:

(SEQ ID NO: 9)
ASHHHHHHLVPRGSSDVPRDLEVVAATPTSLLISWDAPAVTVRYYRITYGE

TGGNSPVQEFTVPGSKSTATISGLKPGVDYTITVYAVTP(Har)GDWNEGG

PISINYRTGKKGK.

In some embodiments, the polypeptide is:

(SEQ ID NO: 9)
ASHHHHHHLVPRGSSDVPRDLEVVAATPTSLLISWDAPAVTVRYYRITYGE

TGGNSPVQEFTVPGSKSTATISGLKPGVDYTITVYAVTP(Har)GDWNEGG

PISINYRTGKKGK.

In some embodiments, the polypeptide has at least 95% sequence identity to a polypeptide which is:

(SEQ ID NO: 10)
SDVPRDLEVVAATPTSLLISWDAPAVTVRYYRITYGETGGNSPVQEFTVPG

SKSTATISGLKPGVDYTITVYAVTPKGDWNEGGPISINYRT;.

In some embodiments, the polypeptide has at least 99% sequence identity to a polypeptide which is:

(SEQ ID NO: 10)
SDVPRDLEVVAATPTSLLISWDAPAVTVRYYRITYGETGGNSPVQEFTVPG

SKSTATISGLKPGVDYTITVYAVTPKGDWNEGGPISINYRT;.

In some embodiments, the polypeptide is:

(SEQ ID NO: 10)
SDVPRDLEVVAATPTSLLISWDAPAVTVRYYRITYGETGGNSPVQEFTVPG

SKSTATISGLKPGVDYTITVYAVTPKGDWNEGGPISINYRT;.

In some embodiments, the polypeptide has at least 95% sequence identity to a polypeptide which is:

(SEQ ID NO: 11)
SDVPRDLEVVAATPTSLLISWDAPAVTVRYYRITYGETGGNSPVQEFTVPG

SKSTATISGLKPGVDYTITVYAVTPRGDWNEGGPISINYRT.

In some embodiments, the polypeptide has at least 99% sequence identity to a polypeptide which is:

(SEQ ID NO: 11)
SDVPRDLEVVAATPTSLLISWDAPAVTVRYYRITYGETGGNSPVQEFTVPG

SKSTATISGLKPGVDYTITVYAVTPRGDWNEGGPISINYRT.

In some embodiments, the polypeptide is:

(SEQ ID NO: 11)
SDVPRDLEVVAATPTSLLISWDAPAVTVRYYRITYGETGGNSPVQEFTVPG

SKSTATISGLKPGVDYTITVYAVTPRGDWNEGGPISINYRT.

The present application further provides a pharmaceutical composition comprising a polypeptide provided herein, and a pharmaceutically acceptable carrier.

The present application further provides a crystal, comprising αVβ3 domain complexed with a polypeptide provided herein.

In some embodiments, the crystal comprises the following cell dimensions:

| | |
|---|---|
| a (Å) | 129.7 |
| b (Å) | 129.7 |
| c (Å) | 308.2 |

The present application further provides a crystal, comprising αIIbβ3 domain complexed with a polypeptide provided herein.

The present application further provides a composition comprising a crystal provided herein.

The present application further provides a method of inhibiting integrin binding and activation in a cell, comprising contacting the cell with an effective amount of a polypeptide provided herein.

The present application further provides a method of inhibiting integrin binding and activation in a subject, comprising administering to the subject a therapeutically effective amount of a polypeptide provided herein.

The present application further provides a method of treating a disease or disorder associated with abnormal activity of one or more integrins in a subject, comprising administering to the subject a therapeutically effective amount of a polypeptide provided herein.

The present application further provides a method of treating a disease or disorder associated with abnormal expression of one or more integrins in a subject, comprising administering to the subject a therapeutically effective amount of a polypeptide provided herein.

In some embodiments, the integrin is selected from the group consisting of αVβ3, αIIbβ3, αvβ1, α4β1, α4β7, αvβ5, αvβ6, and αvβ8.

In some embodiments, the disease or disorder is selected from the group consisting of thrombosis, unstable angina, first or recurrent myocardial infarction, ischemic sudden death, diastolic dysfunction, transient ischemic attack, stroke, atherosclerosis, venous thrombosis, deep vein thrombosis, thrombophlebitis, arterial embolism, coronary and cerebral arterial thrombosis, myocardial infarction, cerebral embolism, kidney embolism, pulmonary embolism, fibrosis, renal fibrosis, delayed graft function, diabetes, tumor angiogenesis, melanoma, cancer metastasis, diabetic nephropathy, diabetic retinopathy, neovascular glaucoma, restenosis, osteoporosis, multiple sclerosis, asthma, ulcerative colitis, skin burns, random flaps, blunt trauma, pitcher shoulder injury, and macular degeneration. In some embodiments the disease or disorder is selected from the group consisting of cancer metastasis, diabetic retinopathy, neovascular glaucoma, thrombosis, restenosis, osteoporosis, and macular degeneration.

In some embodiments, the disease or disorder is thrombosis. In some embodiments, the thrombosis is associated with abnormal activity of integrin αIIbβ3.

In some embodiments, the thrombosis is associated with abnormal expression of integrin αIIbβ3.

In some embodiments, the disease or disorder is fibrosis. In some embodiments, the fibrosis is associated with abnormal activity of an integrin selected from the group consisting of integrin αvβ1, integrin αvβ3, integrin αvβ5, integrin αvβ6, and integrin αvβ8. In some embodiments, the fibrosis is associated with abnormal expression of an integrin selected from the group consisting of integrin αvβ1, integrin αvβ3, integrin αvβ5, integrin αvβ6, and integrin αvβ8. In some embodiments, the fibrosis is selected from the group consisting of liver fibrosis, lung fibrosis, and pancreatic fibrosis.

In some embodiments, the disease or disorder is multiple sclerosis. In some embodiments, the multiple sclerosis is associated with abnormal activity of integrin α4β1. In some embodiments, the multiple sclerosis is associated with abnormal expression of integrin α4β1.

In some embodiments, the disease or disorder is ulcerative colitis. In some embodiments, the ulcerative colitis is associated with abnormal activity of integrin α4β7. In some embodiments, the ulcerative colitis is associated with abnormal expression of integrin α4β7.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used.

The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

DESCRIPTION OF DRAWINGS

FIGS. 9A-9C show mass spectroscopy analysis of Hr10. FIG. 9A shows the translated sequence of Hr10 lacking the N-terminal methionine. The homoarginine (Har) and glycine (replacing $S^{1500}K$) residues are indicated in red. The isotopically-averaged calculated molecular weight is displayed (Protein calculator v3.4). FIG. 9B shows the mass spectrum from the intact Hr10 sample. Major peaks are displayed with assigned charges. FIG. 9C shows a table of the largest peaks showing the m/z ratios for the larges peaks, the calculated charge and resulting molecular weight. The molecular weight calculated from nine peaks is 119868.9±0.5 (mean S.D.) as compared to the calculated weight of the protein lacking the N-terminal Met and with a single L-Har substitution (11969.3).

FIG. 11D shows respective $IC_{50}$, S.E. and p-values from a Fisher test.

DETAILED DESCRIPTION

Figure 1:
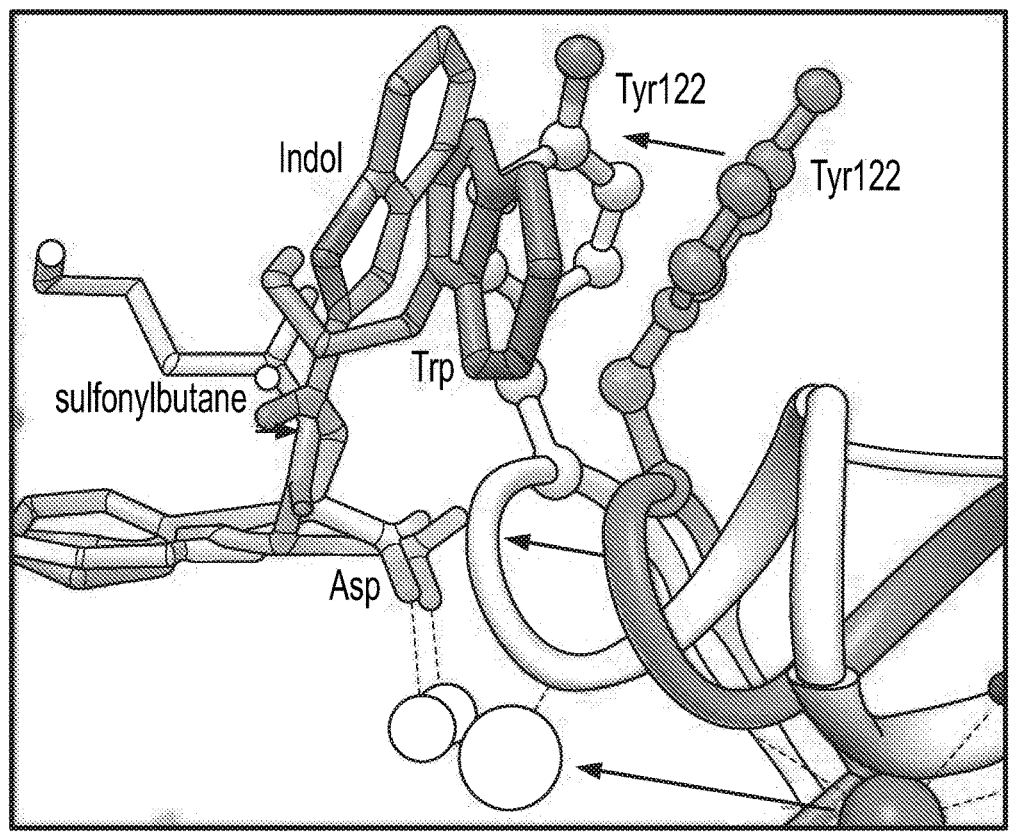
FIG. 1 shows ribbon diagrams of crystal structures of tirofiban-integrin (in white) and Hr10-integrin (in magenta) complexes superposed on the respective of PA domains. The activating inward movement of Ty122 together with the ADMIDAS ion (arrows) is blocked by Hr10 and by the model of the tirofiban variant, mTirofiban (in green, Compound 3, i.e., m-tirofiban) where an indol group is inserted into the tirofiban structure replacing the sulfonylbutane moiety. The metal ions are in the respective colors.
Figure 1:
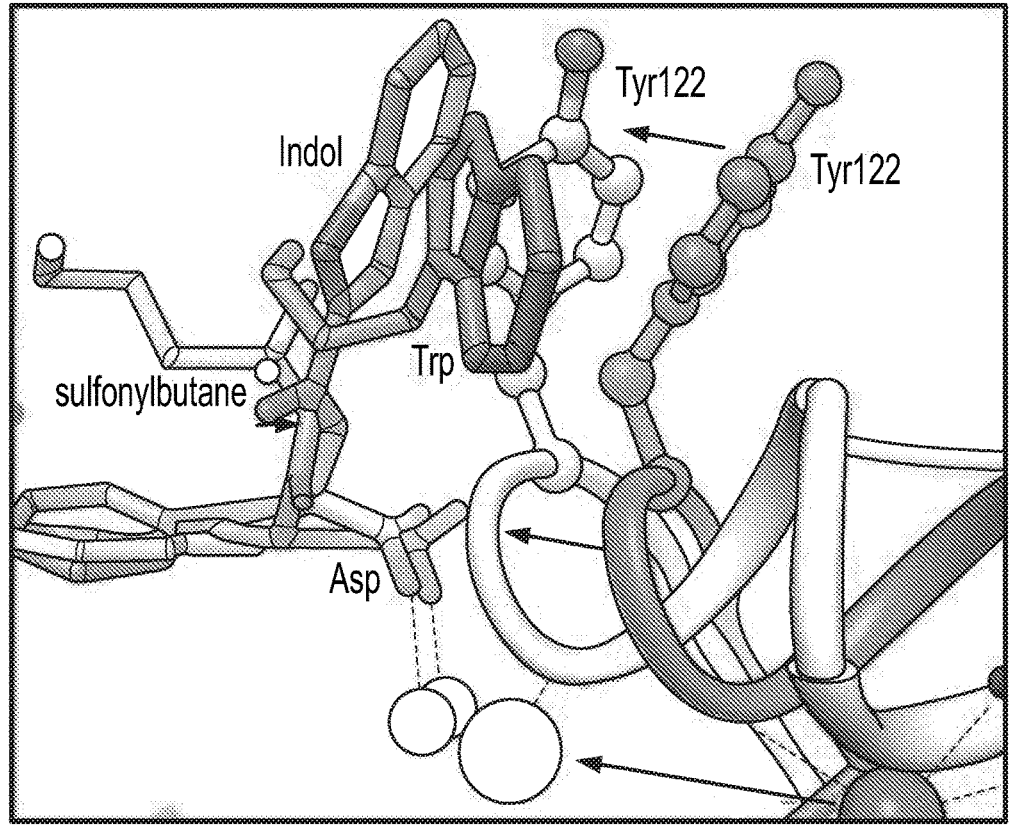

Integrin activity has been linked to numerous human diseases including, for example, heart attacks, stroke, cancer, and other diseases as disclosed herein. Integrin ligand-mimetic antagonists based on the Arg-Gly-Asp (RGD) motif, however, act as partial agonists, inducing conformational changes in the integrin upon binding that can trigger potentially fatal immune reactions and paradoxical cell adhesion in treated patients. These adverse effects have hindered development of anti-integrin therapeutics.

Anti-thrombosis drugs that directly target αIIbβ3 can result in serious bleeding, an adverse outcome that remains high with use of the newer inhibitors of $P_2Y_{12}$ and thrombin receptors (see e.g., Wallentin et al, *N. Engl. J. Med.* 361, 1045-1057 (2009); and Morrow et al, *N. Engl. J. Med.* 366, 1404-1413 (2012)). Platelet activation and accumulation at the site of blood vessel injury are the initial steps in hemostasis. When activated by several agonists including adenosine diphosphate (ADP), thrombin or collagen, platelets adhere to the disrupted surface, and aggregate upon binding of soluble fibrinogen in circulating blood to agonist-activated αIIbβ3 (see e.g., Coller & Shattil, *Blood,* 112, 3011-3025 (2008)). Fibrin generated by thrombin at or near the platelet surface also binds αIIbβ3, driving clot retraction (see e.g., Hantgan & Mousa, *Thromb. Res.* 89, 271-279 (1998)), thereby consolidating the integrity of the hemostatic plug, restoring blood flow and promoting wound closure (see e.g., Tutwiler et al, *Biophys. J.* 112, 714-723 (2017)). Excessive platelet activation by agonists may lead to formation of occlusive thrombi, which are responsible for acute myocardial infarction and stroke (see e.g., Benjamin et al, *Circulation* 135, e146-e603 (2017)), hemodialysis access failure (see e.g., Quencer et al, *Cardiovasc Diagn Ther* 7, S299-S308 (2017)), early loss of kidney allograft (see e.g., Ponticelli et al, *Nephrol. Dial. Transplant* 24, 1388-1393 (2009)), tumor growth and metastasis (see e.g., Lavergne et al, *Cancers (Basel)* 9 (2017)), and may also contribute to fibril formation in cerebral vessels of Alzheimers disease patients (see e.g., Donner et al, *Sci. Signal.* 9, ra52 (2016)).

The three parenteral anti-αIIbβ3 drugs eptifibatide, tirofiban and abciximab (which additionally inhibits αVβ3) have demonstrated efficacy in reducing death and ischemic complications in victims of heart attacks (see e.g., Bosch et al, Cochrane Database Syst Rev, CD002130 (2013)). However, their clinical use in acute coronary syndrome has been associated with serious bleeding, which often requires cessation of therapy, putting heart attack victims at high risk of re-thrombosis. And orally active anti-αIIbβ3 agents given to patients at risk of acute coronary syndromes were abandoned because of increased risk of patient death linked to paradoxical coronary thrombosis (see e.g., Ndrepepa et al, *Coron. Artery Dis.* 25, 456-462 (2014); Ley et al, *Nat. Rev. Drug. Discov.* 15, 173-183 (2016); and Raab-Westphal et al, *Cancers* (Basel) 9 (2017)). Concluding that the adverse outcomes resulting from targeting αIIbβ3 are unavoidable, pharmaceutical companies developed inhibitors of the platelet ADP receptor $P_2Y_{12}$ and thrombin receptor βARI, both upstream of αIIbβ3. However, a considerable number of patients receiving these newer drugs continue to experience serious bleeding and thrombotic events (see e.g., Tsai et al, *Circ. Cardiovasc. Interv.* 3, 230-235 (2010); Tricoci et al, *N. Engl. J. Med.* 366, 20-33 (2012); and Franchi et al, *Nat. Rev. Cardiol.* 12, 30-47 (2015)). Thus, there remains an unmet clinical need for new anti-thrombosis drugs that maintain efficacy while preserving hemostasis (see e.g., McFadyen et al, *Circ. Res.* 121, 1133-1135 (2017)).

Several attempts of developing new anti-thrombosis drugs that maintain efficacy but preserve hemostasis have been reported, for example, targeting collagen receptors α2β1 and GPVI (see e.g., Miller et al, *Proc. Natl. Acad. Sci. U.S.A.* 106, 719-724 (2009); and Ungerer et al, *Circulation,* 123, 1891-1899 (2011), accelerating ADP degradation with CD39 (see e.g., Hohmann et al, *Blood,* 121, 3067-3075 (2013)), or interfering with ADP-induced cell signaling with a PI3Kβ inhibitor (see e.g., Zheng et al, *Eur. J. Med. Chem.* 122, 339-351 (2016)). However, these approaches do not affect platelet activation induced by other potent agonists, and some targets (e.g., PI3Kβ and α2β1) are not platelet-specific. Platelet-leukocyte interactions have also been reported: interfering with binding of leukocyte integrin CD11b to platelet GP1bα delayed thrombosis without prolonging bleeding time in normal mice (see e.g., Wang et al, *Nat. Commun.* 8, 15559 (2017). However, platelet-leukocyte interactions are mediated by multiple receptor-counterreceptor pairs, the relative importance of which may vary with the nature of the pathologic state. Two recent reports discuss targeting αIIbβ3 more directly. In one approach, a short cytoplasmic β3-derived peptide inhibited αIIbβ3 outside-in signaling and prevented thrombosis without prolonging bleeding time, but is not β-integrin specific (see e.g., Shen et al, *Nature*, 503, 131-135 (2013). The second approach utilized low affinity non-RGD small molecules RUC2 and RUC4 that engage the arginine pocket in αIIb (see e.g., Zhu et al, *Sci. Transl. Med.* 4, 125ra132 (2012)) and prevent FeCl$_3$-induced thrombotic arterial occlusion in mice but its effects on clot retraction or bleeding were not reported (see e.g., Li et al, *Arterioscler. Thromb. Vasc. Biol.* 34, 2321-2329 (2014)).

The present application shows that pure orthosteric antagonists of αIIbβ3 block arteriolar thrombosis while preserving hemostasis, thus demonstrating that partial agonism and antagonism are not inseparable. Pure orthosteric antagonism of αIIbβ3 offers significant advantages over the other approaches aimed at preserving hemostasis. For example, by targeting αIIbβ3 MIDAS directly, pure antagonists block binding of several prothrombotic ligands, some of which (e.g. CD40L) (see e.g., Andre et al, *Nat. Med.* 8, 247-252 (2002)) bind leukocyte CD11b (see e.g., Wolf et al, *Circ. Res.* 1269-1279 (2011)) and thus contribute to platelet-leukocyte interactions. In addition, these high affinity pure orthosteric inhibitors do not induce conformational changes directly and, in fact, block these changes when induced by inside-out integrin activation. As disclosed herein, Hr10, a variant of a human natural ligand, is expected to be minimally immunogenic. The present application further describes success in converting the partial agonist, tirofiban, into a pure antagonist using the Hr10/integrin structure, which underscores the primacy of the stable π-π Trp$^{1496}$-β3-Tyr$^{122}$ contact in preventing the activating global conformational change in αIIbβ3, and suggest that this approach may be applicable to engineering drug candidates targeting other integrins, where inadvertent conformational changes may compromise patient safety.

The dual specificity of Hr10, as described herein, to both β3 integrins is shared with the drug abciximab (see e.g., Tam et al, *Circulation*, 98, 1085-1091 (1998)), a property thought to contribute to the long-term clinical benefits of abciximab in acute coronary syndromes (see e.g., Topol et al, *Am. J. Med.* 113, 1-6 (2002); and Admiral et al, *Eur. Heart J.* 26, 2520-2523 (2005)). In addition, dual specificity to both β3 integrins has shown a wide range of anticancer effects (see e.g., Sheldrake et al, *Curr. Cancer Drug Targets,* 9, 519-540 (2009)). For example, abciximab was effective at blocking tumor growth and angiogenesis through targeting the interaction of tumor cells with platelets and endothelial cells, in addition to direct effects on the tumor tissue (see e.g., Trikha et al, *Cancer Res.* 62, 2824-2833 (2002)); Gomes et al, *Clin. Exp. Metastasis,* 21, 553-561 (2004); Engebraaten et al, *Anticancer Res.* 29, 131-137 (2009); and Liu et al, *J. Biomed. Biotechnol.* 2009, 829243 (2009)). Hr10 may thus offer an attractive clinical candidate with minimal bleeding risk and an expected low to absent immunogenicity.

The present application provides polypeptides which act as pure (non-activating) integrin antagonists and overcome the adverse properties described above.

Polypeptides

Accordingly, the present application provides polypeptides which can function as integrin antagonists. In some embodiments, the polypeptide has at least 75% sequence identity, (e.g. at least 80% sequence identity, at least 90% sequence identity, at least 95% sequence identity, at least 99% sequence identity, and the like) to a polypeptide selected from the group consisting of:

```
                                         (SEQ ID NO: 1)
R¹-SDVPRDLEVVAATPTSLLISWDAPAVTVRYYRITYGETGGNSPVQEFT

VPGSKSTATISGLKPGVDYTITVYAVTP(Har)GDWNEGGPISINYRT-

R²;
                                         (SEQ ID NO: 2)
R¹-SDVPRDLEVVAATPTSLLISWDAPAVTVRYYRITYGETGGNSPVQEFT

VPGSKSTATISGLKPGVDYTITVYAVTPKGDWNEGGPISINYRT-R²;;
and
                                         (SEQ ID NO: 3)
R¹-SDVPRDLEVVAATPTSLLISWDAPAVTVRYYRITYGETGGNSPVQEFT

VPGSKSTATISGLKPGVDYTITVYAVTPRGDWNEGGPISINYRT-R²;
``` wherein:

R$^1$ is absent or selected from the group consisting of a histidine tag, the human Fc fragment of IgG comprising a C-terminal histidine tag, an intervening spacer sequence, or a combination thereof;

R$^2$ is absent or X$^1$-KKGK (SEQ ID No: 4);

wherein:

X$^1$ is absent or G.

In some embodiments, the polypeptide has at least 75% sequence identity, (e.g. at least 80% sequence identity, at least 90% sequence identity, at least 95% sequence identity, at least 99% sequence identity, and the like) to a polypeptide selected from the group consisting of:

```
                                         (SEQ ID NO: 1)
R¹-SDVPRDLEVVAATPTSLLISWDAPAVTVRYYRITYGETGGNSPVQEFT

VPGSKSTATISGLKPGVDYTITVYAVTP(Har)GDWNEGGPISINYRT-

R²;
                                         (SEQ ID NO: 2)
R¹-SDVPRDLEVVAATPTSLLISWDAPAVTVRYYRITYGETGGNSPVQEFT

VPGSKSTATISGLKPGVDYTITVYAVTPKGDWNEGGPISINYRT-R²;;
and
                                         (SEQ ID NO: 3)
R¹-SDVPRDLEVVAATPTSLLISWDAPAVTVRYYRITYGETGGNSPVQEFT

VPGSKSTATISGLKPGVDYTITVYAVTPRGDWNEGGPISINYRT-R²;
``` wherein:

R$^1$ is absent or a histidine tag; and

R$^2$ is absent or GKKGK (SEQ ID No: 6).

In some embodiments, the polypeptide has at least 80% sequence identity to a polypeptide selected from the group consisting of SEQ ID No: 1; SEQ ID No: 2; and SEQ ID No: 3. In some embodiments, the polypeptide has at least 85% sequence identity to a polypeptide selected from the group consisting of SEQ ID No: 1; SEQ ID No: 2; and SEQ ID No: 3. In some embodiments, the polypeptide has at least 90% sequence identity to a polypeptide selected from the group consisting of SEQ ID No: 1; SEQ ID No: 2; and SEQ ID No: 3. In some embodiments, the polypeptide has at least 95% sequence identity to a polypeptide selected from the group consisting of SEQ ID No: 1; SEQ ID No: 2; and SEQ ID No: 3. In some embodiments, the polypeptide has at least 97% sequence identity to a polypeptide selected from the group consisting of SEQ ID No: 1; SEQ ID No: 2; and SEQ ID No: 3. In some embodiments, the polypeptide has at least 98% sequence identity to a polypeptide selected from the group consisting of SEQ ID No: 1; SEQ ID No: 2; and SEQ ID No: 3. In some embodiments, the polypeptide has at least 99% sequence identity to a polypeptide selected from the group consisting of SEQ ID No: 1; SEQ ID No: 2; and SEQ ID No: 3. In some embodiments, the polypeptide is selected from the group consisting of SEQ ID No: 1; SEQ ID No: 2; and SEQ ID No: 3.

In some embodiments, R¹ is absent. In some embodiments, R¹ is a histidine tag. In some embodiments, the histidine tag comprises a polypeptide comprising about 5 to about 20 amino acids, for example, about 5 to about 15, about 5 to 10, about 10 to about 20, about 10 to about 15, or about 15 to about 20 amino acids. In some embodiments, the histidine tag comprises a polypeptide having at least 75% sequence identity (e.g., at least 80%, at least 85%, at least 90%, at least 95%, at least 97%, or at least 99%) to a polypeptide having the sequence ASHHHHHHLVPRGS (SEQ ID NO: 5). In some embodiments, the histidine tag comprises a polypeptide having at least 95% sequence identity to a polypeptide having the sequence ASHHHHHHLVPRGS (SEQ ID NO: 5). In some embodiments, the histidine tag comprises a polypeptide having the sequence ASHHHHHHLVPRGS (SEQ ID NO: 5).

In some embodiments, the histidine tag comprises at least one fluorescent small molecule. In some embodiments, the histidine tag comprises one fluorescent small molecule. In some embodiments, the fluorescent small molecule is Alexa Fluor 647.

In some embodiments, R¹ is the human Fc fragment of IgG comprising a C-terminal histidine tag, an intervening spacer sequence, or a combination thereof. In some embodiments, the Fc fragment of human IgG gamma chain comprises a polypeptide having at least 75% sequence identity (e.g., at least 80%, at least 85%, at least 90%, at least 95%, at least 97%, at least 99%) to a polypeptide having the sequence:

(SEQ ID NO: 16)
GPKSCDKTHTCPPCPAPELLGGPSVFLFPPKPKDTLMISRTPEVTCVVVDV

SHEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTCL

VKGFYPSDIAVEWESNGQPENNYKATPPVLDSDGSFFLYSKLTVDKSRWQQ

GNVFSCSVMHEALHNHYTQKSLSLSPGKHHHHHH.

In some embodiments, the Fc fragment of human IgG gamma chain is a polypeptide having the sequence:

(SEQ ID NO: 16)
GPKSCDKTHTCPPCPAPELLGGPSVFLFPPKPKDTLMISRTPEVTCVVVDV

SHEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTCL

VKGFYPSDIAVEWESNGQPENNYKATPPVLDSDGSFFLYSKLTVDKSRWQQ

GNVFSCSVMHEALHNHYTQKSLSLSPGKHHHHHH.

In some embodiments, the histidine tag comprises a polypeptide having at least 75% sequence identity (e.g., at least 80%, at least 85%, at least 90%, at least 95%, at least 97%, at least 99%) to a polypeptide having the sequence ASHHHHHHLVPRGS (SEQ ID NO: 5) and at least one fluorescent small molecule. In some embodiments, the histidine tag comprises a polypeptide having the sequence ASHHHHHHLVPRGS (SEQ ID NO: 5) and a fluorescent small molecule. In some embodiments, the fluorescent small molecule is Alexa Fluor 647.

In some embodiments, R² is absent. In some embodiments, R² is X¹-KKGK (SEQ ID NO: 4). In some embodiments, R² is GKKGK (SEQ ID NO: 6). In some embodiments, R² is KKGK (SEQ ID NO: 31).

In some embodiments, the polypeptide has at least 75% sequence identity (e.g., at least 80%, at least 85%, at least 90%, at least 95%, at least 97%, or at least 99%) to a polypeptide which is:

(SEQ ID NO: 7)
SDVPRDLEVVAATPTSLLISWDAPAVTVRYYRITYGETGGNSPVQEFTVPG

SKSTATISGLKPGVDYTITVYAVTP(Har)GDWNEGGPISINYRT.

In some embodiments, the polypeptide has at least 95% sequence identity to a polypeptide which is SEQ ID NO: 7. In some embodiments, the polypeptide has at least 99% sequence identity to a polypeptide which is SEQ ID NO: 7.

In some embodiments, the polypeptide is:

(SEQ ID NO: 7)
SDVPRDLEVVAATPTSLLISWDAPAVTVRYYRITYGETGGNSPVQEFTVP

GSKSTATISGLKPGVDYTITVYAVTP(Har)GDWNEGGPISINYRT.

In some embodiments, the polypeptide has at least 75% sequence identity (e.g., at least 80%, at least 85%, at least 90%, at least 95%, at least 97%, or at least 99%) to a polypeptide which is:

(SEQ ID NO: 8)
ASHHHHHHLVPRGSSDVPRDLEVVAATPTSLLISWDAPAVTVRYYRITYGE

TGGNSPVQEFTVPGSKSTATISGLKPGVDYTITVYAVTP(Har)GDWNEGG

PISINYRT.

In some embodiments, the polypeptide has at least 95% sequence identity to a polypeptide which is SEQ ID NO: 8. In some embodiments, the polypeptide has at least 99% sequence identity to a polypeptide which is SEQ ID NO: 8.

In some embodiments, the polypeptide is:

(SEQ ID NO: 8)
ASHHHHHHLVPRGSSDVPRDLEVVAATPTSLLISWDAPAVTVRYYRITYGE

TGGNSPVQEFTVPGSKSTATISGLKPGVDYTITVYAVTP(Har)GDWNEGG

PISINYRT.

In some embodiments, the polypeptide has at least 75% sequence identity (e.g., at least 80%, at least 85%, at least 90%, at least 95%, at least 97%, or at least 99%) to a polypeptide which is:

(SEQ ID NO: 9)
ASHHHHHHLVPRGSSDVPRDLEVVAATPTSLLISWDAPAVTVRYYRITYGE

TGGNSPVQEFTVPGSKSTATISGLKPGVDYTITVYAVTP(Har)GDWNEGG

PISINYRTGKKGK.

In some embodiments, the polypeptide has at least 95% sequence identity to a polypeptide which is SEQ ID NO: 9. In some embodiments, the polypeptide has at least 99% sequence identity to a polypeptide which is SEQ ID NO: 9.

In some embodiments, the polypeptide is:

(SEQ ID NO: 9)
ASHHHHHHLVPRGSSDVPRDLEVVAATPTSLLISWDAPAVTVRYYRITYGE

TGGNSPVQEFTVPGSKSTATISGLKPGVDYTITVYAVTP(Har)GDWNEGG

PISINYRTGKKGK.

In some embodiments, the polypeptide has at least 75% sequence identity (e.g., at least 80%, at least 85%, at least 90%, at least 95%, at least 97%, or at least 99%) to a polypeptide which is:

(SEQ ID NO: 10)
SDVPRDLEVVAATPTSLLISWDAPAVTVRYYRITYGETGGNSPVQEFTVPG

SKSTATISGLKPGVDYTITVYAVTPKGDWNEGGPISINYRT;.

In some embodiments, the polypeptide has at least 95% sequence identity to a polypeptide which is SEQ ID NO: 10. In some embodiments, the polypeptide has at least 99% sequence identity to a polypeptide which is SEQ ID NO: 10.

In some embodiments, the polypeptide is:

(SEQ ID NO: 10)
SDVPRDLEVVAATPTSLLISWDAPAVTVRYYRITYGETGGNSPVQEFTVPG

SKSTATISGLKPGVDYTITVYAVTPKGDWNEGGPISINYRT;.

In some embodiments, the polypeptide has at least 75% sequence identity (e.g., at least 80%, at least 85%, at least 90%, at least 95%, at least 97%, or at least 99%) to a polypeptide which is:

(SEQ ID NO: 11)
SDVPRDLEVVAATPTSLLISWDAPAVTVRYYRITYGETGGNSPVQEFTVPG

SKSTATISGLKPGVDYTITVYAVTPRGDWNEGGPISINYRT.

In some embodiments, the polypeptide has at least 95% sequence identity to a polypeptide which is SEQ ID NO: 11. In some embodiments, the polypeptide has at least 99% sequence identity to a polypeptide which is SEQ ID NO: 12.

In some embodiments, the polypeptide is:

(SEQ ID NO: 11)
SDVPRDLEVVAATPTSLLISWDAPAVTVRYYRITYGETGGNSPVQEFTVPG

SKSTATISGLKPGVDYTITVYAVTPRGDWNEGGPISINYRT.

The present application further provides a crystal, comprising αVβ3 domain complexed with a polypeptide provided herein. In some embodiments, the present application provides a composition comprising a crystal described herein.

In some embodiments, the crystal comprises αVβ3 domain complexed with a polypeptide having at least 75% sequence identity (e.g., at least 80%, at least 85%, at least 90%, at least 95%, at least 97%, or at least 99%) to a polypeptide selected from the group consisting of a SEQ ID NO: 1, SEQ ID NO: 2, SEQ ID NO: 3, SEQ ID NO: 7, SEQ ID NO: 8, SEQ ID NO: 9, SEQ ID NO: 10, and SEQ ID NO: 11.

In some embodiments, the crystal comprises αVβ3 domain complexed with a polypeptide having at least 95% sequence identity to a polypeptide which is SEQ ID NO: 1. In some embodiments, the crystal comprises αVβ3 domain complexed with a polypeptide having at least 99% sequence identity to a polypeptide which is SEQ ID NO: 1. In some embodiments, the crystal comprises αVβ3 domain complexed with a polypeptide which is SEQ ID NO: 1.

In some embodiments, the crystal comprises αVβ3 domain complexed with a polypeptide having at least 95% sequence identity to a polypeptide which is SEQ ID NO: 2. In some embodiments, the crystal comprises αVβ3 domain complexed with a polypeptide having at least 99% sequence identity to a polypeptide which is SEQ ID NO: 2. In some embodiments, the crystal comprises αVβ3 domain complexed with a polypeptide which is SEQ ID NO: 2.

In some embodiments, the crystal comprises αVβ3 domain complexed with a polypeptide having at least 95% sequence identity to a polypeptide which is SEQ ID NO: 3. In some embodiments, the crystal comprises αVβ3 domain complexed with a polypeptide having at least 99% sequence identity to a polypeptide which is SEQ ID NO: 3. In some embodiments, the crystal comprises αVβ3 domain complexed with a polypeptide which is SEQ ID NO: 3.

In some embodiments, the crystal comprises αVβ3 domain complexed with a polypeptide having at least 95% sequence identity to a polypeptide which is SEQ ID NO: 7. In some embodiments, the crystal comprises αVβ3 domain complexed with a polypeptide having at least 99% sequence identity to a polypeptide which is SEQ ID NO: 7. In some embodiments, the crystal comprises αVβ3 domain complexed with a polypeptide which is SEQ ID NO: 7.

In some embodiments, the crystal comprises αVβ3 domain complexed with a polypeptide having at least 95% sequence identity to a polypeptide which is SEQ ID NO: 8. In some embodiments, the crystal comprises αVβ3 domain complexed with a polypeptide having at least 99% sequence identity to a polypeptide which is SEQ ID NO: 8. In some embodiments, the crystal comprises αVβ3 domain complexed with a polypeptide which is SEQ ID NO: 8.

In some embodiments, the crystal comprises αVβ3 domain complexed with a polypeptide having at least 95% sequence identity to a polypeptide which is SEQ ID NO: 9. In some embodiments, the crystal comprises αVβ3 domain complexed with a polypeptide having at least 99% sequence identity to a polypeptide which is SEQ ID NO: 9. In some embodiments, the crystal comprises αVβ3 domain complexed with a polypeptide which is SEQ ID NO: 9.

In some embodiments, the crystal comprises αVβ3 domain complexed with a polypeptide having at least 95% sequence identity to a polypeptide which is SEQ ID NO: 10. In some embodiments, the crystal comprises αVβ3 domain complexed with a polypeptide having at least 99% sequence identity to a polypeptide which is SEQ ID NO: 10. In some embodiments, the crystal comprises αVβ3 domain complexed with a polypeptide which is SEQ ID NO: 10.

In some embodiments, the crystal comprises αVβ3 domain complexed with a polypeptide having at least 95% sequence identity to a polypeptide which is SEQ ID NO: 11. In some embodiments, the crystal comprises αVβ3 domain complexed with a polypeptide having at least 99% sequence identity to a polypeptide which is SEQ ID NO: 11. In some embodiments, the crystal comprises αVβ3 domain complexed with a polypeptide which is SEQ ID NO: 11.

In some embodiments, the crystal provided herein comprises the following cell dimensions:

| | |
|---|---|
| a (Å) | 129.7 |
| b (Å) | 129.7 |
| c (Å) | 308.2 |

In some embodiments, the crystal comprises αIIbβ3 domain complexed with a polypeptide having at least 75% sequence identity (e.g., at least 80%, at least 85%, at least 90%, at least 95%, at least 97%, or at least 99%) to a polypeptide selected from the group consisting of a SEQ ID NO: 1, SEQ ID NO: 2, SEQ ID NO: 3, SEQ ID NO: 7, SEQ ID NO: 8, SEQ ID NO: 9, SEQ ID NO: 10, and SEQ ID NO: 11.

In some embodiments, the crystal comprises αIIbβ3 domain complexed with a polypeptide having at least 95% sequence identity to a polypeptide which is SEQ ID NO: 1. In some embodiments, the crystal comprises αIIbβ3 domain complexed with a polypeptide having at least 99% sequence identity to a polypeptide which is SEQ ID NO: 1. In some embodiments, the crystal comprises αIIbβ3 domain complexed with a polypeptide which is SEQ ID NO: 1.

In some embodiments, the crystal comprises αIIbβ3 domain complexed with a polypeptide having at least 95% sequence identity to a polypeptide which is SEQ ID NO: 2. In some embodiments, the crystal comprises αIIbβ3 domain complexed with a polypeptide having at least 99% sequence identity to a polypeptide which is SEQ ID NO: 2. In some embodiments, the crystal comprises αIIbβ3 domain complexed with a polypeptide which is SEQ ID NO: 2.

In some embodiments, the crystal comprises αIIbβ3 domain complexed with a polypeptide having at least 95% sequence identity to a polypeptide which is SEQ ID NO: 3. In some embodiments, the crystal comprises αIIbβ3 domain complexed with a polypeptide having at least 99% sequence identity to a polypeptide which is SEQ ID NO: 3. In some embodiments, the crystal comprises αIIbβ3 domain complexed with a polypeptide which is SEQ ID NO: 3.

In some embodiments, the crystal comprises αIIbβ3 domain complexed with a polypeptide having at least 95% sequence identity to a polypeptide which is SEQ ID NO: 7. In some embodiments, the crystal comprises αIIbβ3 domain complexed with a polypeptide having at least 99% sequence identity to a polypeptide which is SEQ ID NO: 7. In some embodiments, the crystal comprises αIIbβ3 domain complexed with a polypeptide which is SEQ ID NO: 7.

In some embodiments, the crystal comprises αIIbβ3 domain complexed with a polypeptide having at least 95% sequence identity to a polypeptide which is SEQ ID NO: 8. In some embodiments, the crystal comprises αIIbβ3 domain complexed with a polypeptide having at least 99% sequence identity to a polypeptide which is SEQ ID NO: 8. In some embodiments, the crystal comprises αIIbβ3 domain complexed with a polypeptide which is SEQ ID NO: 8.

In some embodiments, the crystal comprises αIIbβ3 domain complexed with a polypeptide having at least 95% sequence identity to a polypeptide which is SEQ ID NO: 9. In some embodiments, the crystal comprises αIIbβ3 domain complexed with a polypeptide having at least 99% sequence identity to a polypeptide which is SEQ ID NO: 9. In some embodiments, the crystal comprises αIIbβ3 domain complexed with a polypeptide which is SEQ ID NO: 9.

In some embodiments, the crystal comprises αIIbβ3 domain complexed with a polypeptide having at least 95% sequence identity to a polypeptide which is SEQ ID NO: 10. In some embodiments, the crystal comprises αIIbβ3 domain complexed with a polypeptide having at least 99% sequence identity to a polypeptide which is SEQ ID NO: 10. In some embodiments, the crystal comprises αIIbβ3 domain complexed with a polypeptide which is SEQ ID NO: 10.

In some embodiments, the crystal comprises αIIbβ3 domain complexed with a polypeptide having at least 95% sequence identity to a polypeptide which is SEQ ID NO: 11. In some embodiments, the crystal comprises αIIbβ3 domain complexed with a polypeptide having at least 99% sequence identity to a polypeptide which is SEQ ID NO: 11. In some embodiments, the crystal comprises αIIbβ3 domain complexed with a polypeptide which is SEQ II) NO: 11.

The present application further provides three-dimensional structures of an integrin ectodomain inhibitor complex, at 3-3.1 Angstrom, or 2.5 Angstrom, resolution or better. The present application exemplifies representative ectodomains, however, ectodomains from other integrins can also be used. In some embodiments, the ectodomain comprises a conserved Tyr that corresponds to Tyr122 in β3. In some embodiments, the alpha domain can be any alpha domain. In some embodiments, the alpha domain is selected from the group of alpha domains provided in Table A.

TABLE A

| | GenBank Acc. No. | |
|---|---|---|
| Integrin | mRNA | Protein |
| alpha V | NM_002210.4 | NP_002201.1 (isoform 1) |
| | NM_001144999.2 | NP_001138471.1 (isoform 2) |
| | NM_001145000.2 | NP_001138472.1 (isoform 3) |
| alpha 1 | NM_181501.1 | NP_852478.1 |
| alpha 2 | NM_002203.3 | NP_002194.2 |
| alpha 2b | NM_000419.3 | NP_000410.2 |
| alpha 3 | NM_002204.2 | NP_002195.1 (isoform a) |
| | NM_005501.2 | NP_005492.1 (isoform b) |
| alpha 4 | NM_000885.4 | NP_000876.3 |
| alpha 5 | NM_002205.2 | NP_002196.2 |
| alpha 6 | NM_001079818.1 | NP_001073286.1 (isoform a) |
| | NM_000210.2 | NP_000201.2 (isoform b) |
| alpha 7 | NM_001144996.1 | NP_001138468.1 (isoform 1) |
| | NM_002206.2 | NP_002197.2 (isoform 2) |
| | NM_001144997.1 | NP_001138469.1 (isoform 3) |
| alpha 8 | NM_003638.2 | NP_003629.2 (isoform 1) |
| | NM_001291494.1 | NP_001278423.1 (isoform 2) |
| alpha 9 | NM_002207.2 | NP_002198.2 |
| alpha 10 | NM_003637.4 | NP_003628.2 (isoform 1) |
| | NM_001303040.1 | NP_001289969.1 (isoform 2) |
| | NM_001303041.1 | NP_001289970.1 (isoform 1) |
| alpha 11 | NM_001004439.1 | NP_001004439.1 |
| alpha L | NM_002209.2 | NP_002200.2 (isoform a) |
| | NM_001114380.1 | NP_001107852.1 (isoform b) |
| alpha M | NM_001145808.1 | NP_001139280.1 (isoform 1) |
| | NM_000632.3 | NP_000623.2 (isoform2) |
| alpha X | NM_001286375.1 | NP_001273304.1 (isoform 1) |
| | NM_000887.4 | NP_000878.2 (isoform 2) |

Alpha and beta domain sequences with 80%, 85%, 90%, 95%, 97%, or 99% or more sequence identity to the sequences provided in Table A can also be used.

In some embodiments, the three-dimensional structure of the ectodomain/inhibitor complex described herein is defined by a set of structural coordinates. In some embodiments, the three-dimensional structure of the ectodomain/inhibitor complex described herein is defined by the set of structural coordinates disclosed in Table 1.

As used herein, the term "structural coordinates" refers to Cartesian coordinates derived from mathematical equations related to the patterns obtained on diffraction of a monochromatic beam of X-rays by the atoms (scattering centers) of an ectodomain/inhibitor complex in crystal form. The diffraction data are used to calculate an electron density map of the repeating unit of the crystal. The electron density maps are then used to establish the positions of the individual atoms of the ectodomain/inhibitor complex.

Slight variations in structural coordinates can be generated by mathematically manipulating the integrin/ligand structural coordinates. For example, the structural coordinates disclosed herein could be manipulated by crystallographic permutation, fractionalization, addition or subtraction of the entire set, inversion, or any combination of the above. Alternatively, modifications in the crystal structure due to mutations, additions, substitutions, and/or deletions of amino acids, or other changes in any of the components that make up the crystal, could also yield variations in structural coordinates. Such slight variations in the individual coordinates will have little effect on the overall configuration. If such variations are within an acceptable standard error as compared to the original coordinates, the resulting three-dimensional shape is considered to be structurally equivalent. In some embodiments, the structure has unit cell parameters as disclosed herein with a variability of at most 5% in all cell parameters.

Figure 6A:
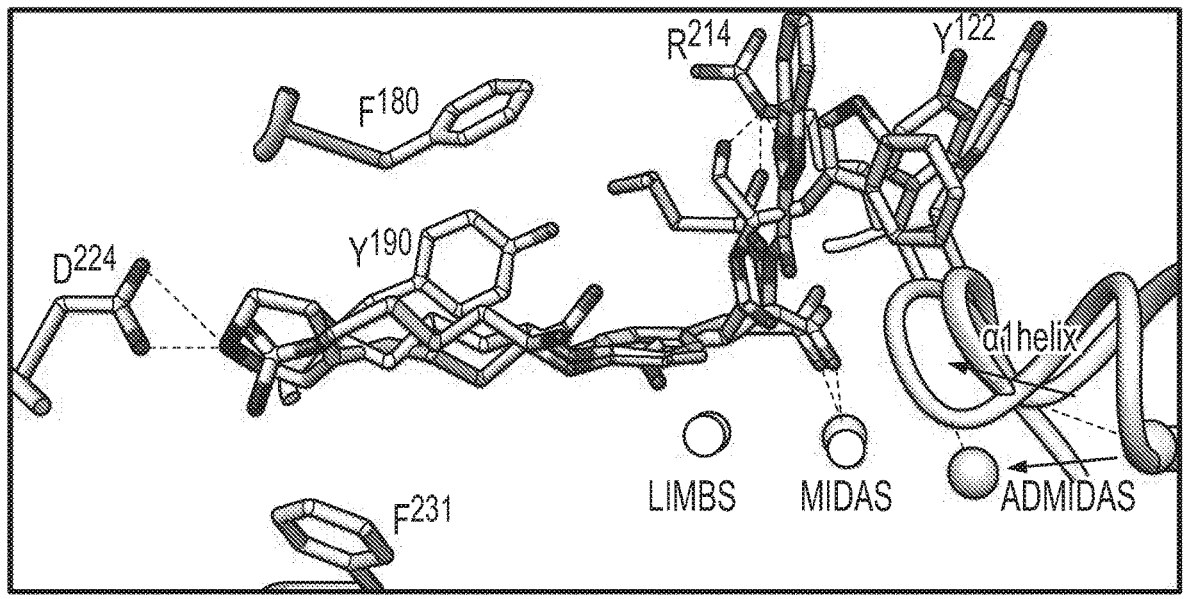
FIG. 6A shows a model of bound M-tirofiban (gold) superposed on the crystal structures of tirofiban/αIIbβ3 (gray) and Hr10/αVβ3 (light blue). The PA domain of each was used in superposition. The metal ions at LIMBS, MIDAS and ADMIDAS and relevant residues are shown in the respective colors. Contacts are shown as dotted red lines.
Figure 7A:
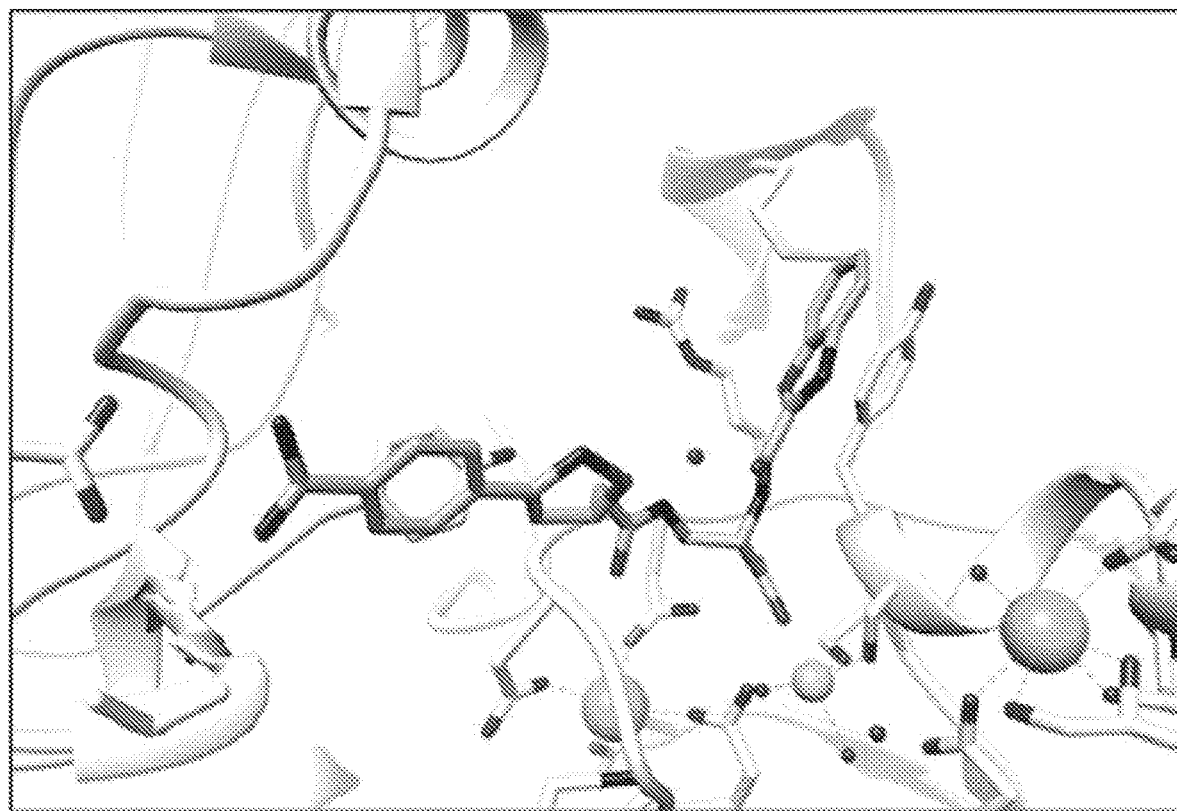
FIGS. 7A-7F show crystal structure models for modification of compounds Roxofiban (FIG. 7A), TDI-4161 (FIG. 7B), Compound C8 (FIG. 7C), Firategrast (FIG. 7D), R00505376 (FIG. 7E), and Carotegrast (FIG. 7F), to produce pure integrin antagonists.
Figure 7B:
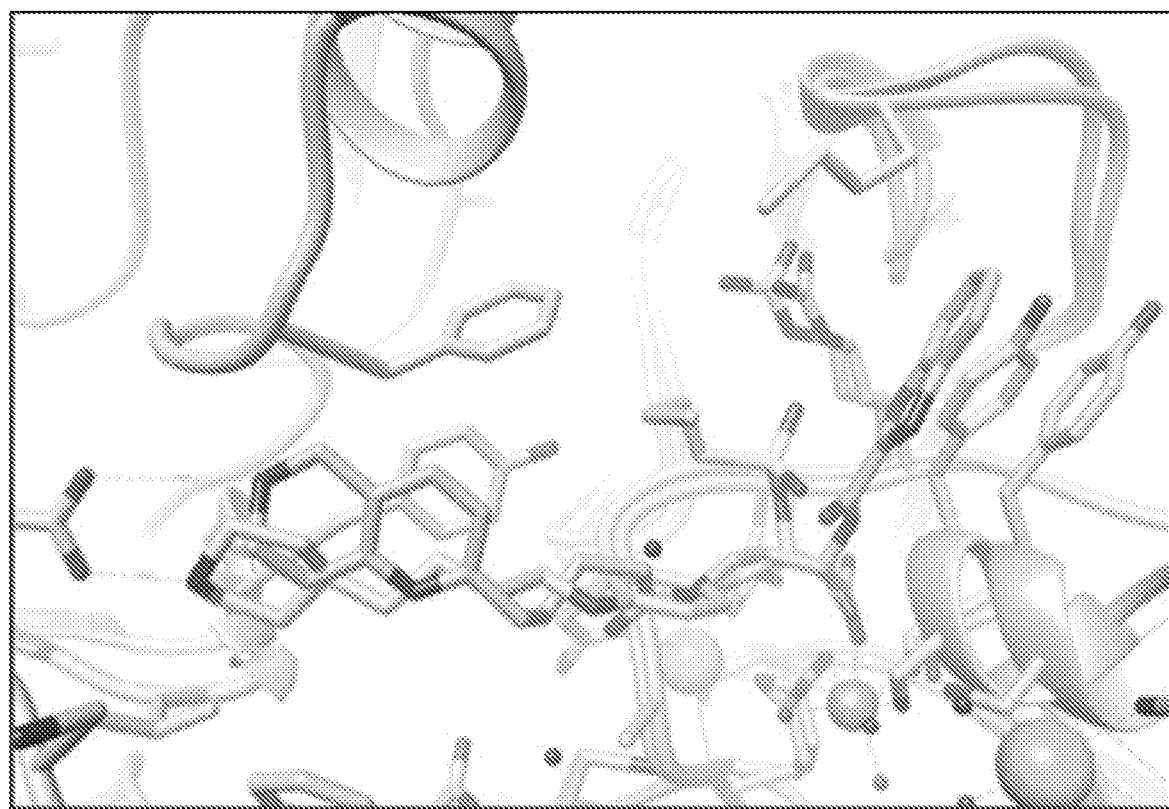
Figure 7C:
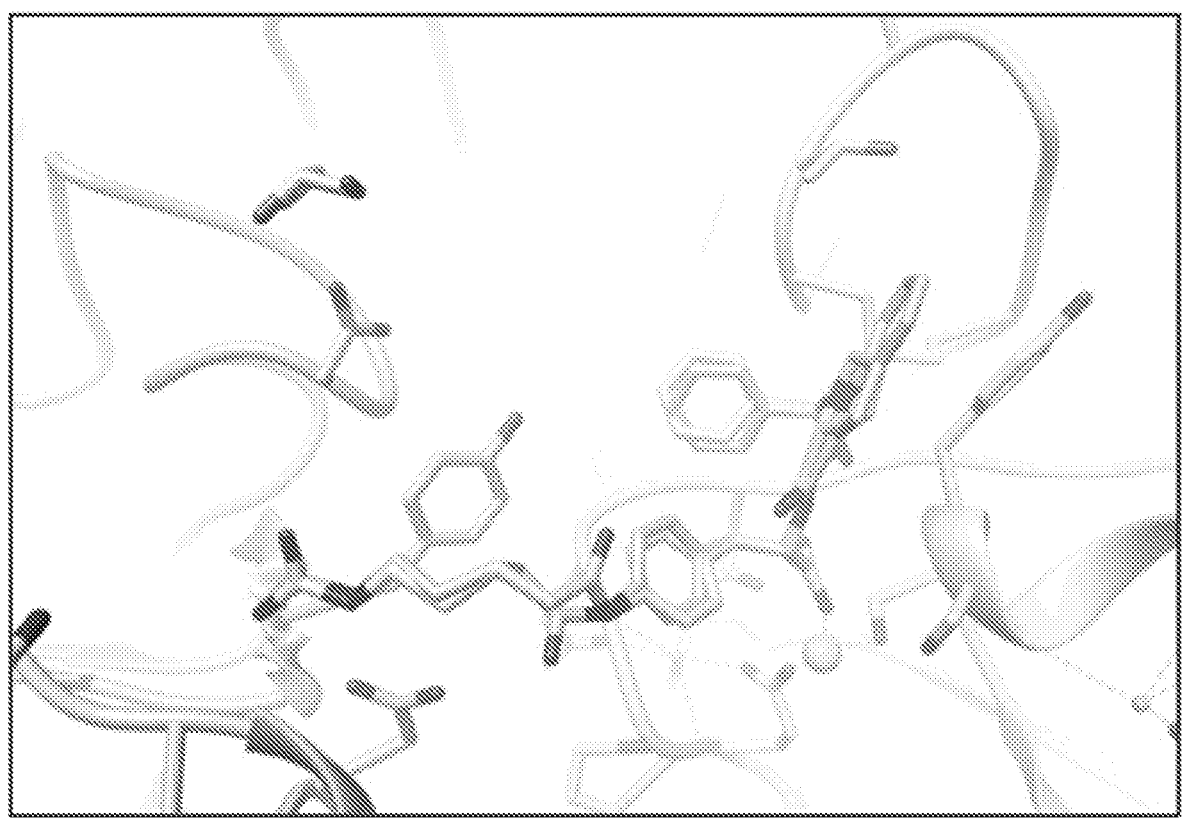
Figure 7D:
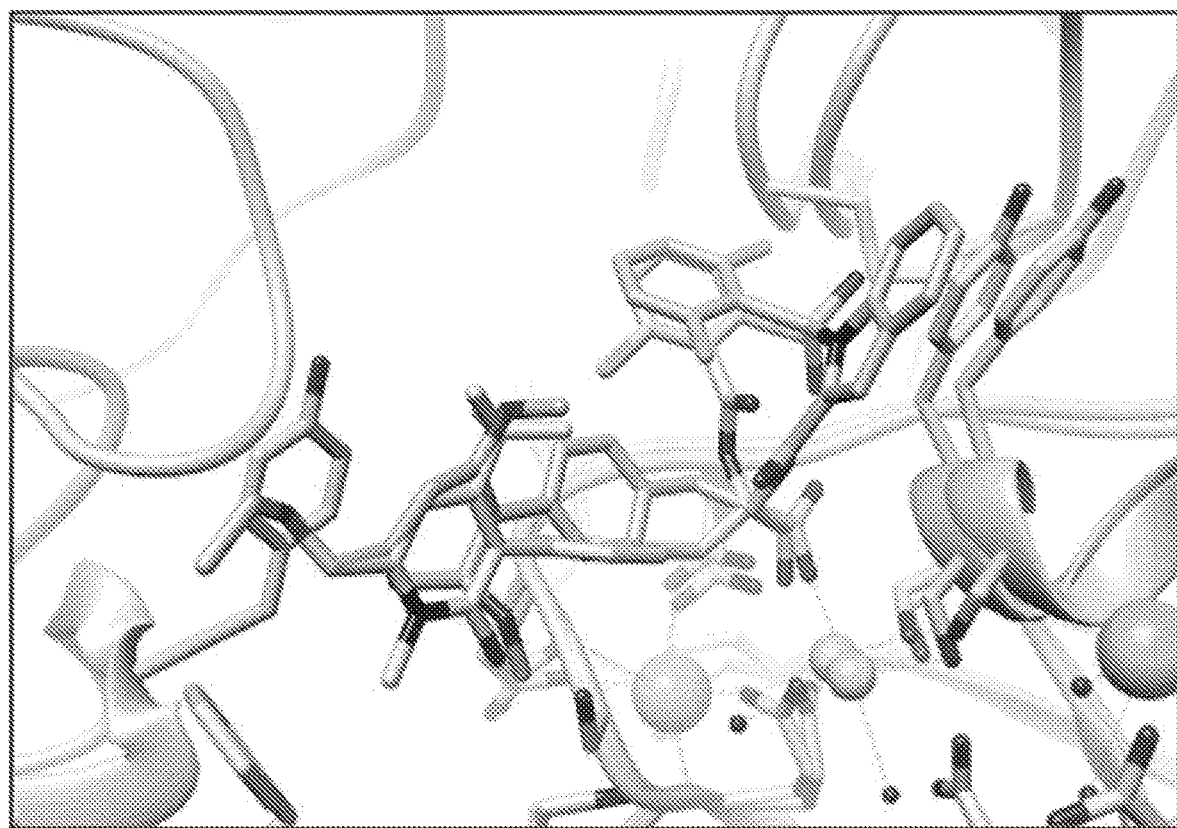
Figure 7E:
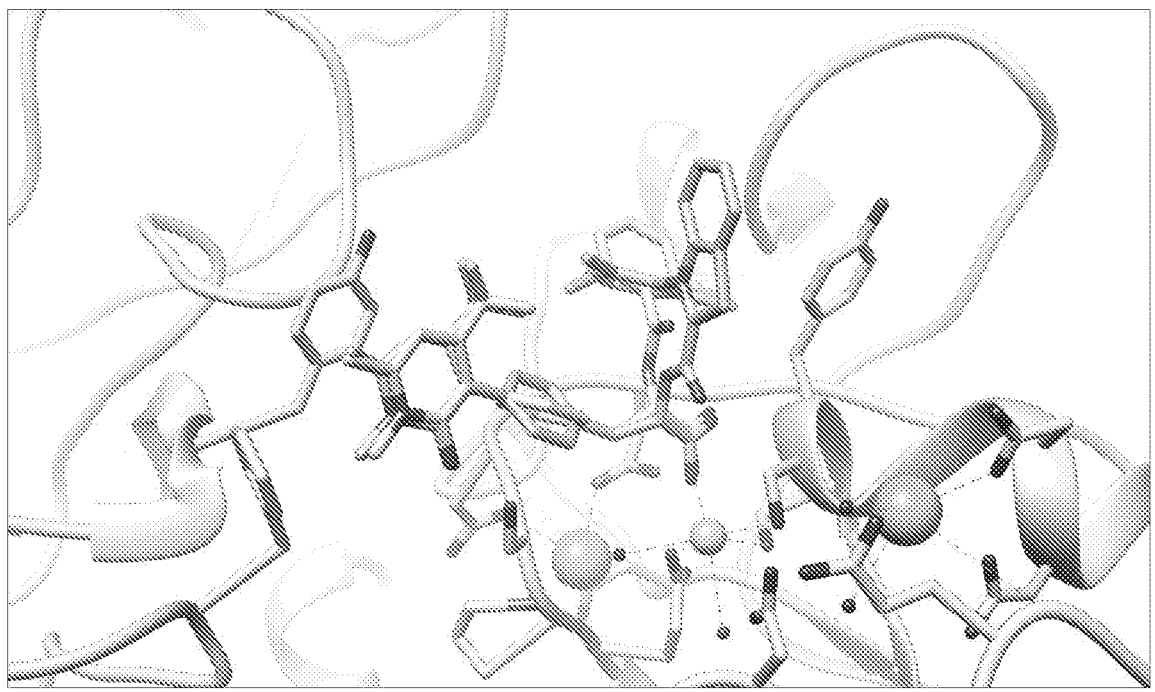
Figure 7F:
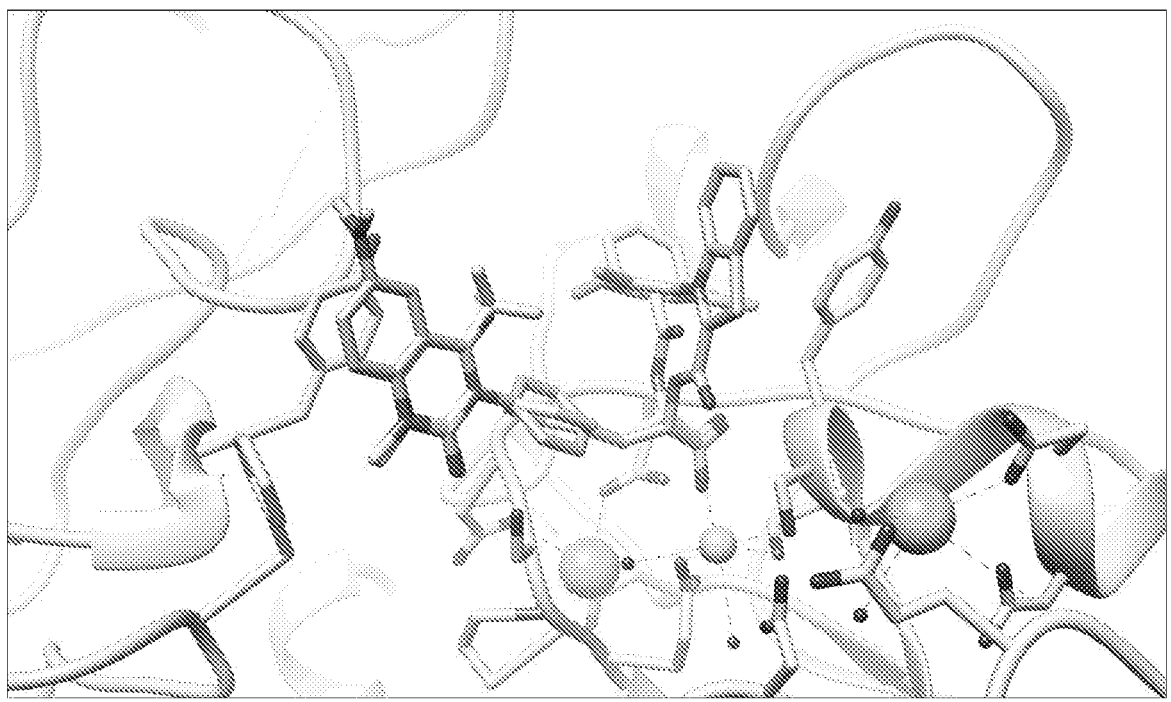
Figure 8A:
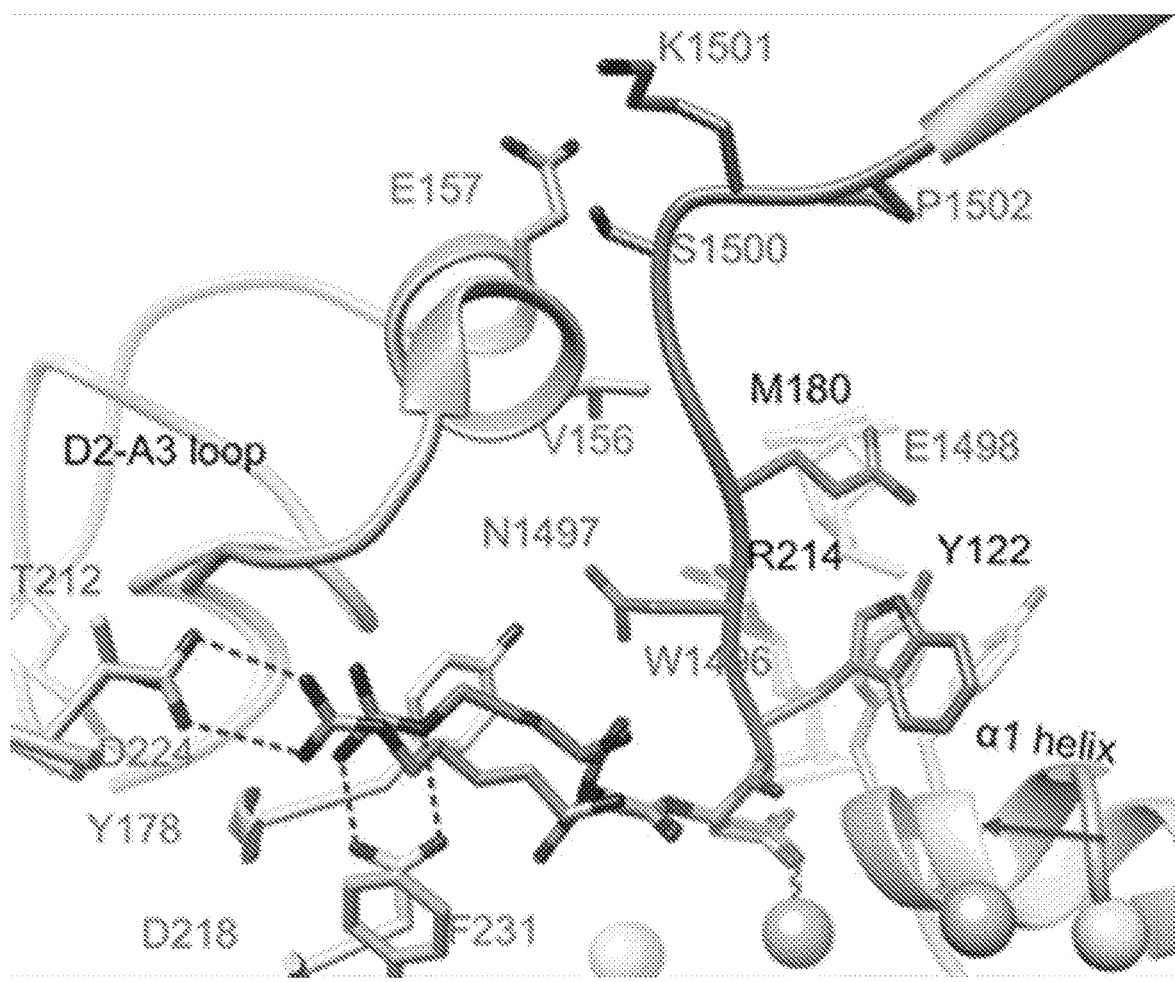
FIG. 8A shows ribbon diagrams of hFN10/αVβ3 (light green) and eptifibatide/αIIbβ3 (light purple) crystal structures superposed on the PA domain of each, with the metal ions at LIMBS, MIDAS and ADMIDAS shown as spheres in the respective colors. Relevant segments of the propeller and PA domains and of hFN10 (dark green) and eptifibatide (dark gray) are shown. The MIDAS ion is ligated by the aspartate residue of each ligand. Residues (single letter code) specific to each structure are shown in the respective color, with residues or loops common in both shown in black. Oxygen, nitrogen, and sulfur atoms are in red, blue and yellow, respectively. The inward movement (red arrow) of the α1 helix (and ADMIDAS ion) towards MIDAS, driven by binding of the partial agonist eptifibatide to αIIbβ3, is absent in hFN10-bound αVβ3, the result of a A-K interaction between ligand $W^{1496}$ and β3-$Y^{122}$. β3-$R^{214}$ and β3-$M^{180}$ contribute to the stability of ligand $W^{1496}$. The homoarginine from eptifibatide forms a bidentate salt bridge with αIIb-D2, whereas $R^{1493}$ of hFN10 contacts αV-$D^{218}$ (replaced by $F^{231}$ in αIIb). A clash between the c-terminal F-G loop of hFN10 and the longer D2-A3 loop of αIIb propeller, replacement of $D^{218}$ in αV with $F^{231}$ in αIIb and the shorter side chain of $R^{1493}$ (vs. homoarginine in eptifibatide) are predicted to account for the poor binding of hFN10 to αIIbβ3.
Figure 10A:
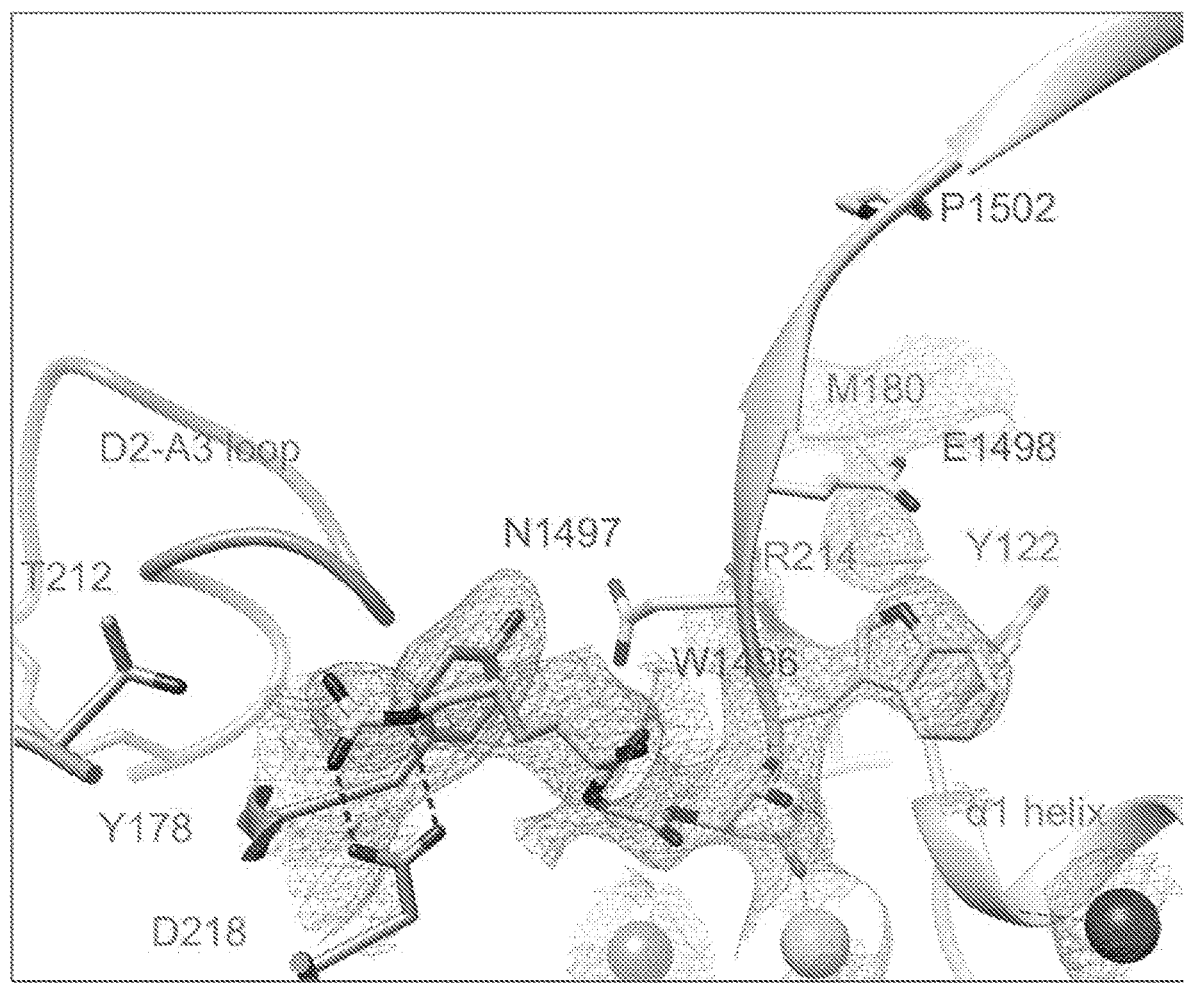
FIG. 10A shows a representative bibbon diagram of the crystal structure of Hr10/αVβ3 complex (same view as FIG. 8A) showing the electron density map at 1.0 σ (blue mesh) of the ligand-binding region. Relevant portions of Hr10 (light green), αV propeller (light blue) and the β3A domain (rose color) are shown. Side-chains are shown as sticks in the respective colors. The $Mn^{2+}$ ions at LIMBS, MIDAS and ADMIDAS are in grey, cyan, and magenta spheres, respectively. Oxygen, nitrogen, and sulfur atoms are colored as in FIG. 8A. Water molecules are not shown. Hr10's $W^{1496}$ forms a π-π interaction with β3-$Y^{122}$, and $Har^{1493}$ forms a bidentate salt bridge with αV-$D^{218}$.
Figure 10B:
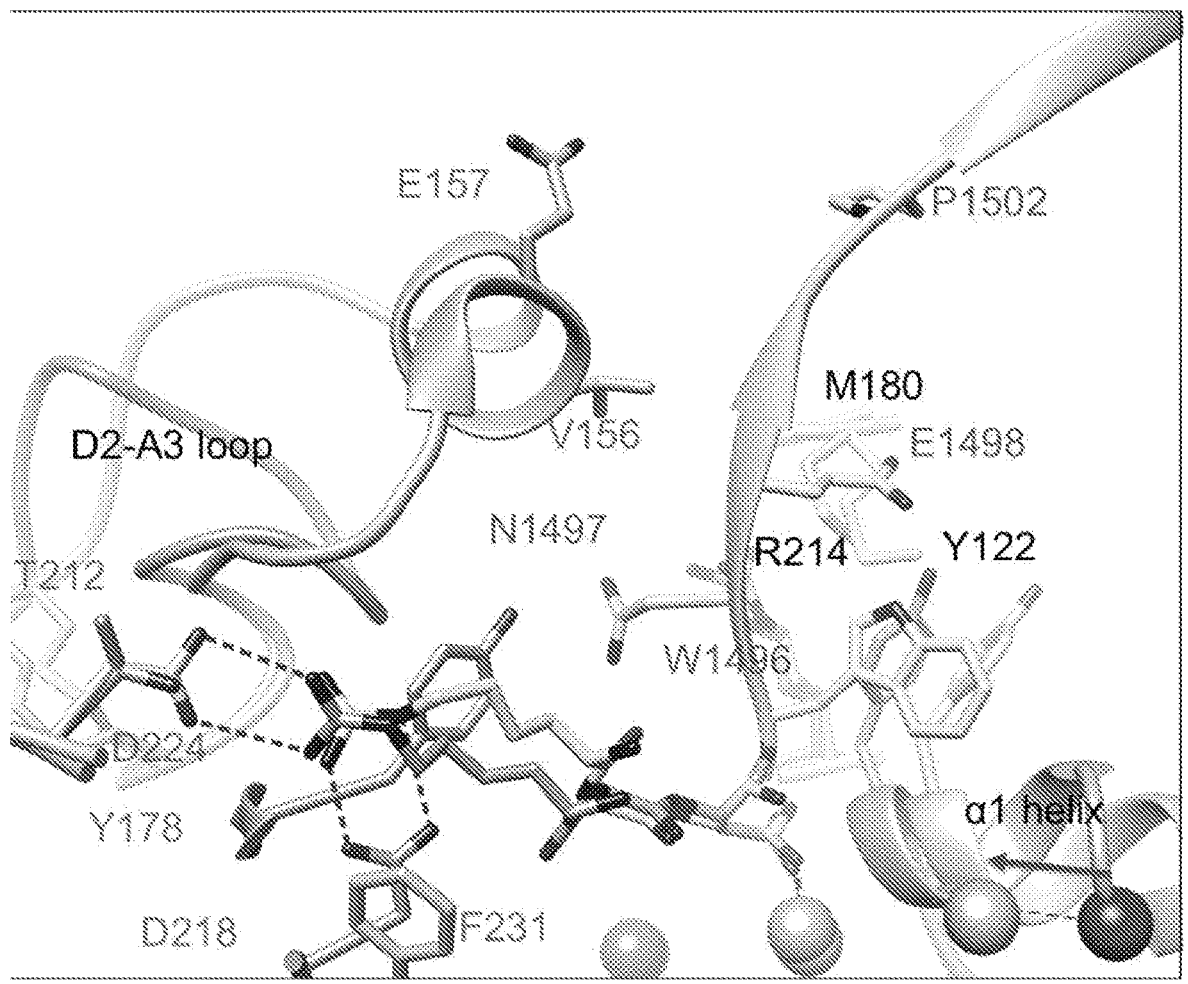
FIG. 10B shows ribbon diagrams of the crystal structures of Hr10/αVβ3 (light green) and eptifibatide/αIIbβ3 (light purple) superposed on the βA domain of each. View, domain, side chain and metal ion colors are as in FIG. 10A. Note the removal of the predicted clash of Hr10 with D2-A3 loop of αIIb and predicted formation of $Har^{1493}$-αIIb-$D^{224}$ salt bridge.

In some embodiments, the crystal is a crystal having a crystal structure model substantially as shown in FIG. 1. In some embodiments, the crystal is a crystal having a crystal structure model substantially as shown in FIG. 6A. In some embodiments, the crystal is a crystal having a crystal structure model substantially as shown in FIG. 7A. In some embodiments, the crystal is a crystal having a crystal structure model substantially as shown in FIG. 7B. In some embodiments, the crystal is a crystal having a crystal structure model substantially as shown in FIG. 7C. In some embodiments, the crystal is a crystal having a crystal structure model substantially as shown in FIG. 7D. In some embodiments, the crystal is a crystal having a crystal structure model substantially as shown in FIG. 7E. In some embodiments, the crystal is a crystal having a crystal structure model substantially as shown in FIG. 7F. In some embodiments, the crystal is a crystal having a crystal structure model substantially as shown in FIG. 8A. In some embodiments, the crystal is a crystal having a crystal structure model substantially as shown in FIG. 10A. In some embodiments, the crystal is a crystal having a crystal structure model substantially as shown in FIG. 10B.

The following abbreviations may be used throughout the present application:

| Amino Acid | Singe Letter Abbreviation | Three Letter Abbreviation |
| --- | --- | --- |
| Alanine | A | Ala |
| Threonine | T | Thr |
| Valine | V | Val |
| Cysteine | C | Cys |
| Leucine | L | Leu |
| Tyrosine | Y | Tyr |
| Isoleucine | I | Ile |
| Asparagine | N | Asn |
| Proline | P | Pro |
| Glutamine | Q | Gln |
| Phenylalanine | F | Phe |
| Aspartic Acid | D | Asp |
| Tryptophan | W | Trp |
| Glutamic Acid | E | Glu |
| Methionine | M | Met |
| Lysine | K | Lys |
| Glycine | G | Gly |
| Arginine | R | Arg |
| Serine | S | Ser |

-continued

| Amino Acid | Singe Letter Abbreviation | Three Letter Abbreviation |
| --- | --- | --- |
| Histidine | H | His |
| Homoarginine | — | Har |

In some embodiments, the polypeptides provided herein are purified polypeptides. As used herein, a "purified" polypeptide refers to a polypeptide that has been removed from its natural environment, i.e., it has been separated from cellular components that naturally accompany it. Typically, a polypeptide is isolated when it is at least 60% (e.g., 70%, 80%, 90%, 95%, or 99%), by weight, free from proteins and molecules that are naturally associated with it.

Also provided are isolated or purified polypeptide sequences that have at least 75% sequence identity (e.g., at least 80%, at least 85%, at least 90%, at least 95%, or at least 99% sequence identity) a polypeptide sequence disclosed herein. In some embodiments, the polypeptide has 100% sequence identity to one of the specific polypeptide sequences provided herein. In calculating percent sequence identity, two sequences are aligned and the number of identical matches of amino acid residues between the two sequences is determined. The number of identical matches is divided by the length of the aligned region (i.e. the number of aligned amino acid residues) and multiplied by 100 to arrive at a percent sequence identity value. It will be appreciated that the length of the aligned region can be a portion of one or both sequences up to the full-length size of the shortest sequence. It will be appreciated that a single sequence can align differently with other sequences and hence, can have different percent sequence identity values over each aligned region. It is noted that the percent identity value is usually rounded to the nearest integer. For example, 78.1%, 78.2%, 78.3%, and 78.4% are rounded down to 78%, while 78.5%, 78.6%, 78.7%, 78.8%, and 78.9% are rounded up to 79%. It is also noted that the length of the aligned region is always an integer.

The alignment of two or more sequences to determine percent sequence identity is performed using the algorithm described by Altschul et al. (1997, *Nucleic Acids Res.*, 25:3389-3402) as incorporated into BLAST (basic local alignment search tool) programs, available at ncbi.nlm.nih.gov on the World Wide Web). BLAST searches can be performed to determine percent sequence identity between a sequence having the activity described herein (i.e., inhibition of integrin activity) and any other sequence or portion thereof aligned using the Altschul et al. algorithm. BLASTP is the program used to align and compare the identity between amino acid sequences. When utilizing a BLAST program to calculate the percent identity between a sequence provided herein and another sequence, the default parameters of the program are used.

In some embodiments, the polypeptides and salts provided herein are substantially isolated. By "substantially isolated" is meant that the polypeptide is at least partially or substantially separated from the environment in which it was formed or detected. Partial separation can include, for example, a composition enriched in the polypeptide provided herein. Substantial separation can include compositions containing at least about 50%, at least about 60%, at least about 70%, at least about 80%, at least about 90%, at least about 95%, at least about 97%, or at least about 99% by weight of the polypeptides provided herein, or salt thereof. Methods for isolating polypeptide and their salts are routine in the art.

The phrase "pharmaceutically acceptable" is employed herein to refer to those polypeptides, salts, and compositions, which are, within the scope of sound medical judgment, suitable for use in contact with the tissues of human beings and animals without excessive toxicity, irritation, allergic response, or other problem or complication, commensurate with a reasonable benefit/risk ratio.

The present application also includes pharmaceutically acceptable salts of the polypeptides described herein. As used herein, "pharmaceutically acceptable salts" refers to derivatives of the disclosed polypeptides wherein the parent polypeptide is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present application include the conventional non-toxic salts of the parent polypeptide formed, for example, from non-toxic inorganic or organic acids. The pharmaceutically acceptable salts of the present application can be synthesized from the parent polypeptide which contains a basic or acidic moiety by conventional chemical methods. Generally, such salts can be prepared by reacting the free acid or base forms of these polypeptides with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (MeCN) are preferred. Lists of suitable salts are found in *Remington's Pharmaceutical Sciences*, 17th ed., Mack Publishing Company, Easton, Pa., 1985, p. 1418 and *Journal of Pharmaceutical Science*, 66, 2 (1977). Conventional methods for preparing salt forms are described, for example, in *Handbook of Pharmaceutical Salts: Properties, Selection, and Use*, Wiley-VCH, 2002.

In some embodiments, the polypeptide provided herein is a pharmaceutically acceptable salt of the polypeptide. All polypeptides, and pharmaceutically acceptable salts thereof, can be found together with other substances such as water and solvents (e.g. hydrates and solvates) or can be isolated.

Polypeptides provided herein can be synthesized according to standard synthesis methods. Charged groups on the polypeptides can be neutralized if desired. For example, the C-terminal carboxylate moiety can be amidated with an —NH$_2$ group, yielding a C(=O)NH$_2$ moiety. Amino acids with many different protecting groups appropriate for immediate use in the solid phase synthesis of polypeptides are commercially available. Additional methods for preparing polypeptides disclosed herein can be found, for example, in S. J. Moore et al. *PNAS* 2013 110(36):14598-14603; and Silverman, A. P. et al. *J. Mol. Biol.* (2009) 385, 1064-1075.

In some embodiments, the polypeptide provided herein comprise a non-native sequence (e.g., a tag, a label, etc.). In some embodiments, a polypeptide provided herein comprises a tag (e.g., a histidine tag). In some embodiments, the tag is fused to the polypeptide sequence of the polypeptide. In some embodiments, the tag is fused to the N-terminus, or the C-terminus, or any combination thereof. In some embodiments, the tag is fused to the N-terminus. In some embodiments, the tag is fused to the C-terminus. In some embodiments, the tag is fused to the N-terminus and the C-terminus.

In some embodiments, the tag is inserted into the polypeptide sequence (e.g., in a solvent accessible surface loop). Exemplary tags include, but are not limited to, affinity tags (e.g., myc, maltose binding protein, 6×his, metal chelating peptides such as multiple histine residues or histidine-tryptophan modules that allow purification on immobilized metals, protein A domains that allow purification on immobilized immunoglobulin, and the domain utilized in the FLAGS extension/affinity purification system), fluorescent tags (e.g., Alexa Fluor 647, green fluorescent protein).

In some embodiments, the tag is a composition detectable by spectroscopic, photochemical, biochemical, immuno-chemical, chemical, or other physical means. For example, tags suitable for use in the present application include, but are not limited to, biotin, digoxigenin, or haptens, as well as proteins which can be made detectable, fluorescent dyes (e.g., Alexa Fluor 647, fluorescein isothiocyanate, Texas red, rhodamine, and the like), radiolabels (e.g., $^3$H, $^{125}$I, $^{35}$S, $^{14}$C, or $^{32}$P), dyes (e.g., alexa, cy3 cy5), chemical conjugates (e.g., quantum dots), enzymes (e.g., horse radish peroxidase, alkaline phosphatase, and others commonly used in an ELISA), and colorimetric labels such as colloidal gold, colored glass or plastic beads (e.g., polystyrene, polypropylene, latex, etc.).

In some embodiments the tag comprises a detectable moiety (e.g., a fluorescent small molecule). For example, where the tag comprises a radioactive moiety, means for detection can include a scintillation counter or photographic film, as in autoradiography. Where the tag comprises a fluorescent moiety, it may be detected by exciting the fluorochrome with the appropriate wavelength of light and detecting the resulting fluorescence. The fluorescence may be detected visually, by the use of electronic detectors such as charge coupled devices (CCDs) or photomultipliers and the like. Similarly, enzymatic tags may be detected by providing the appropriate substrates for the enzyme and detecting the resulting reaction product. Colorimetric or chemiluminescent tags may be detected simply by observing the color associated with the tag.

In some embodiments, the present application further provides methods for identifying a potential inhibitor of an integrin (e.g., a pure integrin antagonist. In some embodiments, the method comprises contacting the integrin (e.g., αVβ6, αVβ1, α4β7, α4β1, and the like) ectodomain or full-length integrin with a potential inhibitor and measuring the ability of the potential inhibitor to bind and/or inhibit the integrin (e.g., the ectodomain or full-length integrin).

In some embodiments, the method comprises:

(i) contacting an integrin (e.g., full integrin or an integrin ectodomain) with a potential inhibitor to form a composition; and (ii) crystallizing the composition to form a crystalline complex wherein the potential inhibitor is bound to the integrin (e.g., the integrin ectodomain).

In some embodiments, the crystal comprises the following cell dimensions:

| | |
|---|---|
| a (Å) | 129.7 |
| b (Å) | 129.7 |
| c (Å) | 308.2 |

In some embodiments, the crystal is a crystal having a crystal structure model substantially as shown in FIG. 1. In some embodiments, the crystal is a crystal having a crystal structure model substantially as shown in FIG. 6A. In some embodiments, the crystal is a crystal having a crystal structure model substantially as shown in FIG. 7A. In some embodiments, the crystal is a crystal having a crystal structure model substantially as shown in FIG. 7B. In some embodiments, the crystal is a crystal having a crystal structure model substantially as shown in FIG. 7C. In some embodiments, the crystal is a crystal having a crystal structure model substantially as shown in FIG. 7D. In some embodiments, the crystal is a crystal having a crystal structure model substantially as shown in FIG. 7E. In some embodiments, the crystal is a crystal having a crystal structure model substantially as shown in FIG. 7F. In some embodiments, the crystal is a crystal having a crystal structure model substantially as shown in FIG. 8A. In some embodiments, the crystal is a crystal having a crystal structure model substantially as shown in FIG. 10A. In some embodiments, the crystal is a crystal having a crystal structure model substantially as shown in FIG. 10B.

In some embodiments, the method comprises:

(i) contacting an integrin (e.g., αVβ6, αVβ1, α4β7, α4β1, and the like) ectodomain or full-length integrin with a potential inhibitor, (ii) measuring the ability of the potential inhibitor to bind and/or inhibit the integrin ectodomain or full-length integrin;

(iii) contacting an integrin (e.g., αVβ6, αVβ1, α4β7, α4β1, and the like) ectodomain or full-length integrin with a polypeptide provided herein;

(iv) measuring the ability of the polypeptide provided herein to bind and/or inhibit the integrin ectodomain or full-length integrin; and (v) comparing the results of steps (ii) and (iv).

In some embodiments, the polypeptide provided herein is useful as a positive control or a standard.

In some embodiments, the polypeptide provided herein is a synthetic polypeptide. In some embodiments, the screening method further comprises:

(vi) preparing a synthetic polypeptide useful for identifying the pure integrin antagonist. In some embodiments, step (vi) is repeated two or more times (i.e., to generate a library of synthetic polypeptides). In some embodiments, step (vi) is performed prior to step (i). In some embodiments, step (vi) is performed prior to step (ii).

In some embodiments, the integrin is selected from the group consisting of αVβ6, αVβ1, α4β7, and α4β1. In some embodiments, the integrin is αVβ6. In some embodiments, the integrin is αVβ1. In some embodiments, the integrin is α4β7. In some embodiments, the integrin is α4β1.

In some embodiments, the synthetic polypeptide is a polypeptide having at least 75% sequence identity (e.g., at least 80%, at least 85%, at least 90%, at least 95%, at least 97%, or at least 99%) to a polypeptide selected from the group consisting of:

```
                                        (SEQ ID NO: 17)
GSSDVPRDLEVVAATPTSLLISWDAPAVTVRYYRITYGETGGNSPVQEFTV

PGSKSTATISGLKPGVDYTITVYA-R3-ISINYRTGKKGK;

(SEQ ID NO: 29)
GSSDVPRDLEVVAATPTSLLISWDAPAVTVRYYRITYGETGGNSPVQEFTV

PGSKSTATISGLKPGVDYTITVYA-R3-GGPISINYRTGKKGK;
and (SEQ ID NO: 30)
GSSDVPRDLEVVAATPTSLLISWDAPAVTVRYYRITYGETGGNSPVQEFTV

PGSKSTATISGLKPGVDYTITVYA-R3-GGPISINYRTGKKGK;
``` wherein $R^3$ is a peptide having at least 75% sequence identity (e.g., at least 80%, at least 85%, at least 90%, at least 95%, at least 97%, or at least 99%) to a peptide which is:

$$X^8-X^9-X^{10}-X^{11}-X^{12}-X^{13}-X^{14}-X^{15}-X^{16}-X^{17}-X^{18}-X^{19}-X^{20}$$
(SEQ ID NO: 18)

wherein:

$X^8$, $X^9$, $X^{10}$, $X^{18}$, $X^{19}$, and $X^{20}$ are each independently selected from any amino acid;

$X^{11}$ is selected from the group consisting of R, I, and L;

$X^{12}$ is selected from the group consisting of G and D;

$X^{13}$ is selected from the group consisting of D, S, and T;

$X^{14}$ is absent or selected from the group consisting of L and W;

$X^{15}$ is absent or selected from any amino acid;

$X^{16}$ is absent or selected from any amino acid; and $X^{17}$ is absent or selected from the group consisting of L and I.

In some embodiments, the synthetic polypeptide is a polypeptide having at least 75% sequence identity (e.g., at least 80%, at least 85%, at least 90%, at least 95%, at least 97%, or at least 99%) to a polypeptide which is SEQ ID NO: 17. In some embodiments, the synthetic polypeptide is a polypeptide having at least 95% sequence identity to a polypeptide which is SEQ ID NO: 17. In some embodiments, the synthetic polypeptide is a polypeptide having at least 99% sequence identity to a polypeptide which is SEQ ID NO: 17.

In some embodiments, the synthetic polypeptide is a polypeptide having at least 75% sequence identity (e.g., at least 80%, at least 85%, at least 90%, at least 95%, at least 97%, or at least 99%) to a polypeptide which is SEQ ID NO: 29. In some embodiments, the synthetic polypeptide is a polypeptide having at least 95% sequence identity to a polypeptide which is SEQ ID NO: 29. In some embodiments, the synthetic polypeptide is a polypeptide having at least 99% sequence identity to a polypeptide which is SEQ ID NO: 29.

In some embodiments, the synthetic polypeptide is a polypeptide having at least 75% sequence identity (e.g., at least 80%, at least 85%, at least 90%, at least 95%, at least 97%, or at least 99%) to a polypeptide which is SEQ ID NO: 30. In some embodiments, the synthetic polypeptide is a polypeptide having at least 95% sequence identity to a polypeptide which is SEQ ID NO: 30. In some embodiments, the synthetic polypeptide is a polypeptide having at least 99% sequence identity to a polypeptide which is SEQ ID NO: 30.

In some embodiments. $X^{11}$ is R. In some embodiments, $X^{11}$ is I. In some embodiments, $X^{11}$ is L.

In some embodiments, $X^{11}$ is G. In some embodiments, $X^{12}$ is D.

In some embodiments, $X^{13}$ is D. In some embodiments, $X^{13}$ is S. In some embodiments, $X^{13}$ is T.

In some embodiments, $X^{11}$-$X^{12}$-$X^{13}$ is RGD. In some embodiments, $X^{11}$-$X^{12}$-$X^{13}$ is IDS. In some embodiments, $X^{11}$-$X^{12}$-$X^{13}$ is IDT. In some embodiments, $X^{11}$-$X^{12}$-$X^{13}$ is LDS. In some embodiments, $X^{11}$-$X^{12}$-$X^{13}$ is LDT.

In some embodiments, $X^{14}$ is absent. In some embodiments, $X^{14}$ selected from the group consisting of L and W. In some embodiments, $X^{14}$ is L. In some embodiments, $X^{14}$ is W.

In some embodiments, $X^{15}$ is absent. In some embodiments, $X^{15}$ is selected from any amino acid.

In some embodiments, $X^{16}$ is absent. In some embodiments, $X^{16}$ is selected from any amino acid.

In some embodiments, $X^{17}$ is absent. In some embodiments, $X^{17}$ is selected from the group consisting of L and I. In some embodiments, $X^{17}$ is L. In some embodiments, $X^{17}$ is I.

In some embodiments, $R^3$ is a peptide having at least 75% sequence identity (e.g., at least 80%, at least 85%, at least 90%, at least 95%, at least 97%, or at least 99%) to a peptide selected from the group consisting of:

$$X^8-X^9-X^{10}-R-G-D-L-X^{15}-X^{16}-X^{17}-X^{18}-X^{19}-X^{20};\quad \text{(SEQ ID NO: 19)}$$

$$X^8-X^9-X^{10}-R-G-D-W-X^{18}-X^{19}-X^{20};\quad \text{(SEQ ID NO: 20)}$$

$$X^8-X^9-X^{10}-R-G-D-W-X^{18}-X^{19}-X^{20};\quad \text{(SEQ ID NO: 21)}$$
and $$X^8-X^9-X^{10}-X^{11}-D-X^{13}-X^{18}-X^{19}-X^{20}.\quad \text{(SEQ ID NO: 22)}$$

In some embodiments, $R^3$ is a peptide having at least 75% sequence identity (e.g., at least 80%, at least 85%, at least 90%, at least 95%, at least 97%, or at least 99%) to a peptide which is:

$$X^8-X^9-X^{10}-R-G-D-L-X^{15}-X^{16}-X^{17}-X^{18}-X^{19}-X^{20}.\quad \text{(SEQ ID NO: 19)}$$

In some embodiments, $R^3$ is a peptide having at least 75% sequence identity (e.g., at least 80%, at least 85%, at least 90%, at least 95%, at least 97%, or at least 99%) to a peptide which is:

$$X^8-X^9-X^{10}-R-G-D-W-X^{18}-X^{19}-X^{20}.\quad \text{(SEQ ID NO: 20)}$$

In some embodiments, $R^3$ is a peptide having at least 75% sequence identity (e.g., at least 80%, at least 85%, at least 90%, at least 95%, at least 97%, or at least 99%) to a peptide which is:

$$X^8-X^9-X^{10}-R-G-D-W-X^{18}-X^{19}-X^{20}.\quad \text{(SEQ ID NO: 21)}$$

In some embodiments, $R^3$ is a peptide having at least 75% sequence identity (e.g., at least 80%, at least 85%, at least 90%, at least 95%, at least 97%, or at least 99%) to a peptide which is:

$$X^8-X^9-X^{10}-X^{11}-D-X^{13}-X^{18}-X^{19}-X^{20}.\quad \text{(SEQ ID NO: 22)}$$

In some embodiments, $R^3$ is a peptide having at least 75% sequence identity (e.g., at least 80%, at least 85%, at least 90%, at least 95%, at least 97%, or at least 99%) to a peptide selected from the group consisting of:

$$X^8-X^9-X^{10}-R-G-D-L-X^{15}-X^{16}-L-X^{18}-X^{19}-X^{20};\quad \text{(SEQ ID NO: 23)}$$

$$X^8-X^9-X^{10}-R-G-D-L-X^{15}-X^{16}-I-X^{18}-X^{19}-X^{20};\quad \text{(SEQ ID NO: 24)}$$

$$X^8-X^9-X^{10}-R-G-D-W-X^{18}-X^{19}-X^{20};\quad \text{(SEQ ID NO: 20)}$$

$$X^8-X^9-X^{10}-R-G-D-W-X^{18}-X^{19}-X^{20};\quad \text{(SEQ ID NO: 21)}$$

$$X^8-X^9-X^{10}-I-D-S-X^{18}-X^{19}-X^{20};\quad \text{(SEQ ID NO: 25)}$$

$$X^8-X^9-X^{10}-I-D-T-X^{18}-X^{19}-X^{20};\quad \text{(SEQ ID NO: 26)}$$

$$X^8-X^9-X^{10}-L-D-S-X^{18}-X^{19}-X^{20};\quad \text{(SEQ ID NO: 27)}$$
and $$X^8-X^9-X^{10}-L-D-T-X^{18}-X^{19}-X^{20}.\quad \text{(SEQ ID NO: 28)}$$

In some embodiments, $R^3$ is a peptide having at least 75% sequence identity (e.g., at least 80%, at least 85%, at least 90%, at least 95%, at least 97%, or at least 99%) to a peptide which is:

$$X^8-X^9-X^{10}-R-G-D-L-X^{15}-X^{16}-L-X^{18}-X^{19}-X^{20}.\quad \text{(SEQ ID NO: 23)}$$

In some embodiments, $R^3$ is a peptide having at least 75% sequence identity (e.g., at least 80%, at least 85%, at least 90%, at least 95%, at least 97%, or at least 99%) to a peptide which is:

$$X^8-X^9-X^{10}-R-G-D-L-X^{15}-X^{16}-I-X^{18}-X^{19}-X^{20}.\quad \text{(SEQ ID NO: 24)}$$

In some embodiments. $R^3$ is a peptide having at least 75% sequence identity (e.g., at least 80%, at least 85%, at least 90%, at least 95%, at least 97%, or at least 99%) to a peptide which is:

$$X^8-X^9-X^{10}-I-D-S-X^{18}-X^{19}-X^{20}.\quad \text{(SEQ ID NO: 25)}$$

In some embodiments, $R^3$ is a peptide having at least 75% sequence identity (e.g., at least 80% h, at least 85%, at least 90%, at least 95%, at least 97%, or at least 99%) to a peptide which is:

$$X^8-X^9-X^{10}-I-D-T-X^{18}-X^{19}-X^{20}.\quad \text{(SEQ ID NO: 26)}$$

In some embodiments, $R^3$ is a peptide having at least 75% sequence identity (e.g., at least 80%, at least 85%, at least 90%, at least 95%, at least 97%, or at least 99%) to a peptide which is:

$$X^8-X^9-X^{10}-L-D-S-X^{18}-X^{19}-X^{20}.\quad \text{(SEQ ID NO: 27)}$$

In some embodiments, $R^3$ is a peptide having at least 75% sequence identity (e.g, at least 80%, at least 85%, at least 90%, at least 95%, at least 97%, or at least 99%) to a peptide which is:

$$X^8-X^9-X^{10}-L-D-T-X^{18}-X^{19}-X^{20}.\quad \text{(SEQ ID NO: 28)}$$

Methods of Use

The present application further provides methods of using the integrin inhibiting polypeptides, or pharmaceutically acceptable salts thereof, described herein. Integrins have been established as therapeutic targets in a number of conditions (see e.g., Cox et al., *Nature Reviews Drug Dis-* covery, 2010; 9(10):804-20; Maile et al., Sci. Transl. Med. 2, 18ra11 (2010); and Gerber et al., Nature, 503:126-130 (2013)). Thus, the present application provides methods for inhibiting integrin activity to treat diseases or disorders that would benefit from reduced integrin activity. In some embodiments, the polypeptides provided herein are useful for blocking and/or inhibiting (e.g., reducing) integrin function while decreasing and/or avoiding the side effects that can result from inadvertent activation of the receptor. An exemplary side effect that can result from inadvertent activation of the receptor includes, but is not limited to, thrombocytopenia (e.g., severe thrombocytopenia).

In some embodiments, the present application provides a method of inhibiting integrin binding and activation on a cell and/or in a subject (e.g., in a subject in need thereof). As used herein, the term "subject," refers to any animal, including mammals. Example subjects include, but are not limited to, mice, rats, rabbits, dogs, cats, swine, cattle, sheep, horses, primates, and humans. In some embodiments, the subject is a human.

In some embodiments, the method comprises inhibiting integrin binding and activation on a cell, comprising contacting the cell with a therapeutically effective amount of a polypeptide provided herein, or a pharmaceutically acceptable salt thereof. In some embodiments, method comprises inhibiting integrin binding and activation in a subject, comprising administering to the subject a therapeutically effective amount of a polypeptide provided herein, or a pharmaceutically acceptable salt thereof. In some embodiments, the method is an in vitro method. In some embodiments, the method is an in vivo method.

In some embodiments, the present application further provides a method of treating a disease or disorder associated with abnormal activity of one or more integrins in a subject. In some embodiments, the method comprises administering to the subject (e.g., a subject in need thereof) a therapeutically effective amount of a polypeptide provided herein, or a pharmaceutically acceptable salt thereof. The present disclosure includes methods for the treatment of diseases mediated by integrin function, for example, wherein the integrin has a conserved tyrosine in a position analogous to Tyr122 in beta3. A previously reported alignment of integrin sequences has demonstrated that the following integrins have a conserved Tyrosine:

beta3 integrins: $\alpha$IIb$\beta$3 and $\alpha$V$\beta$3;

beta1 integrins: $\alpha$1$\beta$1, $\alpha$2$\beta$1, $\alpha$4$\beta$1, $\alpha$5$\beta$1, $\alpha$6$\beta$1, $\alpha$7$\beta$1, $\alpha$8$\beta$1, $\alpha$9$\beta$1, $\alpha$1$\beta$1, $\alpha$11$\beta$1, $\alpha$V$\beta$1;

beta2 integrins: $\alpha$L$\beta$2 (LFA-1, CD11a/CD18), $\alpha$M$\beta$2 (CD11b/CD18), $\alpha$X$\beta$2 (p150.95, CD11c/CD18) and $\alpha$D$\beta$2 (CD11d/CD18);

beta7 integrins: $\alpha$4$\beta$7 and $\alpha$E$\beta$7 (see e.g., U.S. Patent Publication No.: 2017/0044236, the disclosure of which is incorporated herein in its entirety).

The following Tyr122-containing integrins have been shown to be involved in various diseases. A representative list of diseases and disorders associated with each integrin are shown below in Table B.

TABLE B

| Integrin | Disease or condition |
|---|---|
| $\alpha_{IIb}\beta_3$ | Thrombosis (e.g., heart attacks, stroke, vascular dementia) |
| $\alpha_V\beta_3$ | Osteoporosis; Fibrosis (e.g., heart, kidney, lung, liver, skin); tumor-indy bone resorption; atherosclerosis, diabetes; tumor angiogenesis, melanonin proteinuria; sickle cell disease vaso-occlusion; T cell lymphoma; Crohn's |

TABLE B-continued

| Integrin | Disease or condition |
|---|---|
| | disease strictures; supra-valvular aortic stenosis associated with William's syndrome; post-cardiac transplant coronary vasculopathy |
| $\alpha_v\beta_1$ | Fibrosis of liver (NASH), lung (IPF), kidney |
| $\alpha_2\beta_1$ | Solid tumors, ADPKD |
| $\alpha_3\beta_1$ | Solid tumors |
| $\alpha_4\beta_1$ | Multiple sclerosis, asthma, ulcerative colitis, Crohn's disease |
| $\alpha_5\beta_1$ | Angiogenesis, age-related macular degeneration |
| $\alpha_L\beta_2$ | Psoriasis, keratoconjunctivitis sicca (dry eye) |
| $\alpha_M\beta_2$ | Ischemia-reperfusion injury syndrome, blunt trauma; pitcher's shoulder injury; fibroinflammation, keratoconjunctivitis sicca (dry eye) |
| $\alpha_4\beta_7$ | inflammatory bowel disease (e.g., ulcerative colitis) |

Accordingly, the present application further provides a method of treating a disease or disorder associated with abnormal activity and/or abnormal expression of one or more integrins in a subject. In some embodiments, the method comprises administering to the subject (e.g., a subject in need thereof) a therapeutically effective amount of a polypeptide provided herein, or a pharmaceutically acceptable salt thereof.

In some embodiments, the disease or disorder is selected from the group consisting of thrombosis, unstable angina, ischemic sudden death, diastolic dysfunction, transient ischemic attack, stroke, atherosclerosis, thrombophlebitis, arterial embolism, myocardial infarction, cerebral embolisms, kidney embolisms, pulmonary embolism, fibrosis, renal fibrosis, delayed graft function, diabetes, tumor angiogenesis, melanoma, cancer metastasis, diabetic nephropathy, diabetic retinopathy, neovascular glaucoma, restenosis, osteoporosis, multiple sclerosis, asthma, ulcerative colitis, random flaps, and macular degeneration.

In some embodiments, the disease or disorder is selected from the group consisting of thrombosis, unstable angina, first or recurrent myocardial infarction, ischemic sudden death, diastolic dysfunction, transient ischemic attack, stroke, atherosclerosis, venous thrombosis, deep vein thrombosis, thrombophlebitis, arterial embolism, coronary and cerebral arterial thrombosis, myocardial infarction, cerebral embolism, kidney embolism, pulmonary embolism, fibrosis, renal fibrosis, delayed graft function, diabetes, tumor angiogenesis, melanoma, cancer metastasis, diabetic nephropathy, diabetic retinopathy, neovascular glaucoma, restenosis, osteoporosis, multiple sclerosis, asthma, ulcerative colitis, skin burns, random flaps, blunt trauma, pitcher shoulder injury, and macular degeneration. In some embodiments the disease or disorder is selected from the group consisting of cancer metastasis, diabetic retinopathy, neovascular glaucoma, thrombosis, restenosis, osteoporosis, and macular degeneration.

In some embodiments, the disease or disorder is selected from the group of diseases and disorders provided in Table B.

In some embodiments, the disease or disorder is selected from the group consisting of thrombosis, fibrosis, multiple sclerosis, and ulcerative colitis.

In some embodiments, the disease or disorder is disorder is thrombosis. In some embodiments, the thrombosis is associated with abnormal activity and/or abnormal expression of integrin $\alpha$IIb$\beta$3. In some embodiments, the thrombosis is selected from the group consisting of venous thrombosis, deep vein thrombosis, coronary arterial thrombosis, and cerebral arterial thrombosis.

In some embodiments, the disease or disorder is disorder is fibrosis. In some embodiments, the fibrosis is associated with abnormal activity and/or abnormal expression of an integrin selected from the group consisting of integrin αvβ1, integrin αvβ3, integrin αvβ5, integrin αvβ6, and integrin αvβ8. In some embodiments, the fibrosis is selected from the group consisting of liver fibrosis, kidney fibrosis (renal fibrosis), lung fibrosis, and pancreatic fibrosis. In some embodiments, the fibrosis is selected from the group consisting of liver fibrosis, lung fibrosis, and pancreatic fibrosis.

In some embodiments, the disease or disorder is disorder is multiple sclerosis. In some embodiments, the multiple sclerosis is associated with abnormal activity and/or abnormal expression of integrin α4β1.

In some embodiments, the disease or disorder is disorder is ulcerative colitis. In some embodiments, the ulcerative colitis is associated with abnormal activity and/or abnormal expression of integrin α4β7.

In some embodiments, the disease or disorder is an angiogenic disorder. As used herein, the term "angiogenic disorder" refers to conditions involving abnormal neovascularization, including but not limited to, tumor metastasis and ocular neovascularization, such as diabetic retinopathy, neovascular glaucoma, age-related macular degeneration, and retinal vein occlusion.

In some embodiments, the disease or disorder is a thromboembolic disorder. As used herein, the term "thromboembolic disorder" refers to conditions involving platelet activation and aggregation, including, but not limited to, arterial or venous cardiovascular or cerebrovascular thromboembolic disorders, such as thrombosis, unstable angina, first or recurrent myocardial infarction, ischemic sudden death, transient ischemic attack, stroke, atherosclerosis, venous thrombosis, deep vein thrombosis, thrombophlebitis, arterial embolism, coronary and cerebral arterial thrombosis, myocardial infarction, cerebral embolism, kidney embolism, pulmonary embolism, or such disorders associated with diabetes. In some embodiments, the disease or disorder is selected from the group consisting of stroke and heart attack.

In some embodiments, the disease or disorder is myocardial infarction. In some embodiments, the myocardial infarction is a first myocardial infarction. In some embodiments, the myocardial infarction is a recurrent myocardial infarction.

In some embodiments, the disease or disorder is associated with a cell adhesion processes. Exemplary diseases or disorders associated with a cell adhesion process include, but are not limited to, inflammation, bone degradation, restenosis, rheumatoid arthritis, asthma, allergy, adult respiratory distress syndrome, graft versus host disease, organ transplantation rejection, septic shock, psoriasis, eczema, contact dermatitis, osteoporosis, osteoarthritis, atherosclerosis, inflammatory bowel disease, and other autoimmune diseases. In some embodiments, the polypeptides provided herein, or a pharmaceutically acceptable salt thereof, may be useful in wound healing.

In some embodiments, the polypeptides provided herein, or a pharmaceutically acceptable salt thereof, are administered to a subject (e.g., a subject in need thereof) in a therapeutically effective amount. As used herein, the phrase "therapeutically effective amount" refers to the amount of active polypeptide or pharmaceutical agent that elicits the biological or medicinal response that is being sought in a tissue, system, animal, individual or human by a researcher, veterinarian, medical doctor or other clinician.

As used herein, the term "treating" or "treatment" refers to one or more of (1) inhibiting the disease; for example, inhibiting a disease, condition or disorder in an individual who is experiencing or displaying the pathology or symptomatology of the disease, condition or disorder (i.e., arresting further development of the pathology and/or symptomatology); and (2) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease or reducing or alleviating one or more symptoms of the disease.

Combination Therapies

One or more additional therapeutic agents such as, for example, anti-coagulant, coagulation inhibitory agents, anti-platelet inhibitory agents, platelet inhibitory agents, thrombin inhibitors, thrombolytic agents, fibrinolytic agents, or anesthetic agents (e.g., for use in combination with a surgical procedure) can be used in combination with the polypeptides and salts provided herein.

Example anti-coagulant or coagulation inhibitory agents include, but are not limited to, heparin, sodium crystalline clathrate, and warfarin.

Example anti-platelet or platelet inhibitory agents include, but are not limited to, aspirin, piroxicam, and ticlopidine;

Example thrombin inhibitors include, but are not limited to, boropeptides, hirudin, and argatroban;

Example thrombolytic agents or fibrinolytic agents include, but are not limited to plasminogen activators, anistreplase, urokinase, and streptokinase.

Example anesthetics include, but are not limited to, local anesthetics (e.g., lidocaine, procain, ropivacaine) and general anesthetics (e.g., desflurane, enflurane, halothane, isoflurane, methoxyflurane, nitrous oxide, sevoflurane, mmobarbital, methohexital, thiamylal, thiopental, diazepam, lorazepam, midazolam, etomidate, ketamine, propofol, alfentanil, fentanyl, remifentanil, buprenorphine, butorphanol, hydromorphone levorphanol, meperidine, methadone, morphine, nalbuphine, oxymorphone, pentazocine).

The polypeptides provided herein can be administered in combination with one or more additional therapeutic agents, for example, to reduce the dosage of each drug required to achieve the desired therapeutic effect. Thus, the combination treatment provided herein may permit the use of lower doses of each polypeptide or salt, with reduced adverse, toxic effects of each polypeptide or salt. A lower dosage can minimize the potential of side effects of the polypeptides or salts, thereby providing an increased margin of safety relative to the margin of safety for each component when used as a single agent. Such combination therapies may be employed to achieve synergistic or additive therapeutic effects for the treatment of thromboembolic or other disorders.

In some embodiments, the additional therapeutic agent is administered simultaneously with a polypeptide or salt provided herein. In some embodiments, the additional therapeutic agent is administered after administration of the polypeptide or salt provided herein. In some embodiments, the additional therapeutic agent is administered prior to administration of the polypeptide or salt provided herein. In some embodiments, the polypeptide or salt provided herein is administered during a surgical procedure. In some embodiments, the polypeptide or salt provided herein is administered in combination with an additional therapeutic agent during a surgical procedure.

Pharmaceutical Formulations

When employed as pharmaceuticals, the polypeptide and salts provided herein can be administered in the form of pharmaceutical compositions. These compositions can be prepared as described herein or elsewhere, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer, intratracheal or intranasal), oral, or parenteral. Parenteral administration includes intravenous, intraarterial, subcutaneous, intraperitoneal intramuscular or injection or infusion; or intracranial, (e.g., intrathecal or intraventricular, administration). Parenteral administration can be in the form of a single bolus dose, or may be, for example, by a continuous perfusion pump. In some embodiments, the polypeptides, salts, and pharmaceutical compositions provided herein are suitable for parenteral administration. In some embodiments, the polypeptide, salts, and pharmaceutical compositions provided herein are suitable for intravenous administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Also provided are pharmaceutical compositions which contain, as the active ingredient, a polypeptide provided herein, or a pharmaceutically acceptable salt thereof, in combination with one or more pharmaceutically acceptable carriers (e.g., excipients). In making the compositions provided herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments, soft and hard gelatin capsules, suppositories, sterile injectable solutions, and sterile packaged powders.

Some examples of suitable excipients include, without limitation, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include, without limitation, lubricating agents such as talc, magnesium stearate, and mineral oil; wetting agents; emulsifying and suspending agents; preserving agents such as methyl- and propylhydroxy-benzoates; sweetening agents; flavoring agents, or combinations thereof.

The active ingredient can be effective over a wide dosage range and is generally administered in a pharmaceutically effective amount. It will be understood, however, that the amount of the polypeptide actually administered will usually be determined by a physician, according to the relevant circumstances, including the condition to be treated, the chosen route of administration, the actual polypeptide administered, the age, weight, and response of the individual subject, the severity of the subject's symptoms, and the like.

Examples

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results.

General Methods and Materials

Reagents and Antibodies

Restriction and modification enzymes were obtained from New England Biolabs Inc. (Beverly, Mass.). Cell culture reagents were purchased from Invitrogen (San Diego, Calif.) or Fisher Scientific (Hampton, N.H.). The Fab fragment of AP5 was prepared by papain digestion followed by anion exchange and size-exclusion chromatography. Hybridoma producing β3 conformation-insensitive mAb AP3 was bought from ATCC and antibody purified by affinity chromatography. Alexa Fluor 488-conjugated mAbs against human CD62P and CD63 were purchased from Santa Cruz Biotechnology, Dallas, Tex. Alexa Fluor647-conjugated anti-human CD42b mAb was purchased from R&D Systems, Minneapolis, Minn. APC-labeled goat anti-mouse Fc-specific antibody was purchased from Jackson ImmunoResearch (West Grove, Pa.). Alexa Fluor 647-conjugated Penta-His mAb was purchased from Qiagen, Germantown, Md. eptifibatide and tirofiban were purchased from Millipore-Sigma (Burlington, Mass.). M-tirofiban [OC(=O) [C2H](CC1=CC=C(OCCCCC2CCNCC2)C=C1)NC(=O)C1=NC2=C(O1)C =CC=C2] was synthesized at the Organic Chemistry Collaborative Center, Columbia University Irving Medical Center, NY. Purity for M-tirofiban was determined through high-performance liquid chromatography and found to be >95% pure. The plasmid pCDF5-Har, containing two copies of a UAG recognizing tRNA and the tRNA synthase (Har-Rs) for charging UAG tRNAs with Har, and the *E. coli* strain B-95ΔA containing a deletion of release factor 1 (prfA) and 95 synonymous TAG stop codon mutations, were provided (RIKEN, Yokohama, Japan) (see e.g., Mukai et al, *Nucleic Acids Res.* 43, 8111-8122 (2015)). L-Har and TRAP-6 were purchased from Bachem. ADP, collagen, ATP, Chrono-luminescence reagent and human thrombin were purchased from Chrono-log (Havertown, βA).

Plasmids, Mutagenesis, Protein Expression, Purification and Mass Spectrometry

Human αVβ3 ectodomain was expressed and purified as previously described (see e.g., Van Agthoven et al, *Nat. Struct. Mol. Biol.* 21, 383-388 (2014)). hFN10 was expressed in BL21-DE3 bacteria and purified by affinity chromatography followed by gel filtration as previously described (Id.). FN10 containing a TAG stop codon at position 1493 was generated by PCR-based mutagenesis with the Quick-change kit (Agilent Technologies), cloned into bacterial expression plasmid pET11a and verified by DNA sequencing. A bacterial stock of *E. coli* strain B-95AA containing plasmids pCDF5-Har and pET-11a/hFN10-TAG grown in LB media supplemented with 5 mM L-Har, 50 μg/ml kanamycin (pCDF5-Har) and 100 μg/mL ampicillin (pET-11a) was prepared and used to express Hr10. Bacterial cultures at ~0.5 A (600 nm) were induced with 0.3 mM IPTG and grown for 8 hours at room temperature. Hr10 was purified as for hFN10 (Id.) and purity assessed by fractionation on gradient SDS-PAGE gels followed by Coomassie staining.

Cell Lines, Cell Culture and Transfection

Human αVβ3-K562 cells have been previously described (Id.). K562 cells stably expressing αIIbβ3 (αIIbβ3-K562) (see e.g., Silverman et al, *J. Mol. Recognit.* 24, 127-135 (2011) were maintained in Iscove's modified Dulbecco's medium plus G418 (0.5-1.0 mg/mL), supplemented with 10% fetal calf serum, 2 mM L-glutamine, penicillin and streptomycin.

Ligand Binding and Flow Cytometry

For ligand binding assays, αIIβ3-K562 or αVβ3-K562 cells (1×10$^6$) were suspended in 100 μL of WB (20 mM Hepes, 150 mM NaCl, pH 7.4, containing 0.1% [w/v] bovine serum albumin, 1 mM each of $MgCl_2$ and $CaCl_2$, and incubated first with Hr10 or hFN10 (each at 3-10 sg/mL) for 30 min at room temperature (RT). After washing, cells were incubated for 30 additional minutes at 4° C. with Alexa Fluor 647 conjugated Penta-His mAb. Integrin expression was independently analyzed for each condition by incubating cells with the Alexa647-conjugated AP3 (10 μg/mL) for 30 min on ice. Cells were washed, re-suspended, fixed in 2% paraformaldehyde and analyzed using FACSCalibur or BD-LSRII flow cytometers (BD Biosciences). Ligand binding was expressed as mean fluorescence intensity (MFI), as determined using FlowJo software. Mean and SD from independent experiments were calculated and compared using Student's t-test.

For ligand binding competition studies, 100 μL of PT-25-activated αIIbβ3-K562 (1×10$^6$) were incubated for 30 minutes at RT with serially diluted concentrations of Hr10, hFN10, or eptifibatide in the presence of 0.5 μM Alexa647-conjugated FB. Cells were washed, fixed in 2% paraformaldehyde and analyzed by flow cytometry. Ligand binding was expressed as $IC_{50}$ of cells in the absence of competitor ligands. Mean and SD from three independent experiments were calculated, and compared using Student's t-test.

Platelet Aggregation and ATP Secretion

Platelet aggregation and ATP secretion in whole blood were performed in a Chrono-Log model 700 two-channel lumi-aggregation system following the manufacturer's instructions. Blood was drawn directly into 3.2% sodium citrate from healthy volunteers, and blood was used within 3 hours. None of the subjects were taking any medications for at least 10 days prior. For impedance aggregation measurements, 0.5 mL of blood was mixed with 0.5 mL physiologic saline supplemented with inhibitors and incubated at 37° C. for 5 minutes without stirring. Measurements were performed with stirring at 1,200 rpm at 37° C. Values for each data point represent impedance measurements following application of agonist integrated over 5 minutes. Data points for an individual dose curve were serially collected from a single draw and analyzed with SigmaPlot (Systat Software, San Jose, Calif.) using a least-square fit to a logistic curve and the $IC_{50}$ value determined from the fitted parameter. ATP secretion proceeded similarly except that 0.45 mL of whole blood were added to 0.45 mL of saline supplemented with various concentrations of Hr10 or eptifibatide to produce the desired concentration at 1.0 mL. Following incubation for 5 minutes at 37° C., 100 μL of Chrono-lume reagent was added and aggregation initiated. The luminescence signal was quantified with a non-aggregated sample supplemented with an ATP standard.

Binding of mAbs

αVβ3-K562 cells or transiently transfected HEK293T (0.5×10$^6$ in 100 μL WB) were incubated in the absence or presence of unlabeled Hr10 or eptifibatide, each at 1.5 μM, for 20 min at RT. Alexa647-labeled AP5 Fab or unlabeled anti-LIBS-1 (each to 10 μg/mL) were added, and cells incubated for an additional 30 min before washing. Alexa647-labeled AP3 was used for normalization of integrin expression. APC-labeled goat anti-mouse Fc-specific antibody was added to anti-LIBS-1-bound cells for an additional 30 min at 4° C., cells washed and processed for flow cytometry. Binding of anti-CD62 and anti-CD63 mAbs to platelets was performed by incubating (20 min, RT) 100 μL of ligand-pretreated 3.2% sodium citrate whole blood with either Alexa488-labeled mAb (at 10 μg/mL) in the presence of 10 μg/mL Alexa647-labeled anti-CD42b. Cells were fixed in 2% paraformaldehyde and CD62 and CD63 expression was analyzed by flow cytometry in the CD42b positive population.

Crystallography, Structure Determination and Refinement

Human αVβ3 ectodomain was purified and crystallized by the hanging drop method as previously described (see e.g., Xiong et al, *Science*, 294, 339-345 (2001)). Hr10 was soaked for 3 weeks into the preformed αVβ3 crystals at 1.5 mM in the crystallization well solution containing 1 mM $Mn^{2+}$. Crystals were harvested in 12% PEG 3500 (polyethylene glycol, molecular weight 3500), in 100 mM sodium acetate, pH 4.5, 800 mM NaCl plus 2 mM $Mn^{2+}$ and FN10 (at 1.5 mM), cryoprotected by addition of glycerol in 2% increments up to 24% final concentration, and then flash-frozen in liquid nitrogen. Diffraction data was collected at ID-19 of APS, indexed, integrated, scaled by HKL2000 (see e.g., Otwinowski et al, *Processing of X-ray diffraction data collected in oscillation mode*, Vol. 276 (Academic Press, 1997)), and solved by molecular replacement using 3IJE as the search model in PHASER. The structure was refined with Phenix using translation-liberation-screw, automatic optimization of X-ray and stereochemistry, and Ramachandran restriction in the final cycle. Data collection and refinement statistics are shown in Table 1. The coordinates and structure factors of αVβ3/Hr10 have been deposited in the Protein Data Bank under accession code 6NAJ. Structural illustrations were prepared with Chimera.

Generation of vWF$^{R1326H}$ H Knock-In (KI) NSG Mice

CRISPR/Cas 9 technology was used to generate the vWF R1326H KI mice of NSG background with a mutation of specific nucleotide at the exon 28 of the mouse vWF gene, resulting in replacing the Arginine (codon CGT) at amino acid no.1326 by Histidine (codon CAT). An sgRNA was designed according to the online resources, the sgRNA Designer: CRISPRko and the Cas-OFFinder, and the sgRNAs with less than 3 mismatches and less than 25 off-target sites were used. The sgRNA target sequence was 5'-CTT-GAGCTCAA GGTAGGCAC-3' (SEQ ID NO: 12). The histidine codon was repaired into the gene with a single-stranded oligos. (5'-ACATCTCTCAGAAGCG-CATCCGCGTGGCAGTGGTAGAGTACCATGATGGA TCCCATGCTTATCTTGAGCTCAAGGCCCG-GAAGCGACCCTCAGAGCTTCG GCGCAT-CACCAGCCAGATTA-3'(SEQ ID NO: 13; Integrated DNA technologies, Inc.). Preparation of sgRNA and Cas9 RNA for pronucleus microinjection followed instruction instructor's manual (AmpliCap-Max™ T7 High Yield Message Maker kit). Pronuclear microinjection was performed on fertilized eggs from NSG mice. Genotyping of founder mice was performed by PCR, TA-cloning, followed by Sanger DNA sequencing. The primer sequences for PCR genotyping were 5'-TCACTGTGATG GTGTGAACC-3' (SEQ ID NO: 14) paring with 5'-CTGACTATCTC ATCTCTTC-3' (SEQ ID NO: 15). PCR condition was 95° C., 5 min, followed by 35 cycles of 95° C., 30 sec, 55° C., 30 sec, and 72° C., 30 sec, and a final extension at 72° C., 7 min. TA-cloning followed an instructor's manual (T3 Cloning kit; ZGene Biotech Inc.). Production of the vWF R1326H KI NSG mice was carried out by the Transgenic Mouse Model Core Facility.

Clot Retraction

750 μL of Tyrode's buffer supplemented with inhibitor was mixed in a glass culture tube with 200 μL of PRP and 5 μL red blood cells. Clotting was initiated by addition of 50 μL thrombin at 10 units/mL in saline and a sealed Pasteur pipette secured in the tube center. Digital photographs of the experiment were taken at 15-minute intervals over 2 hours. Images were analyzed with ImageJ software to determine the area occupied by the clot and plasma. Plots of the relative areas and linear regressions were performed with SigmaPlot (Systat Software, San Jose, Calif.).

Cremaster Laser Injury Animal Studies

Human blood was collected in 0.129 M sodium citrate (10:1 vol/vol). Blood was obtained from healthy donors after informed consent. Platelet-rich plasma (PRP) was separated after centrifugation (200 g, 10 minutes) at room temperature (RT). The platelets were then isolated from PRP, and prostaglandin E1 (Sigma-Aldrich) added to a final concentration of 1 μM. Platelets were then pelleted by centrifugation (800 g, 10 minutes) at RT. The pellet was washed in calcium-free Tyrode's buffer (134 mM NaCl, 3 mM KCl, 0.3 mM $NaH_2PO_4$, 2 mM $MgCl_2$, 5 mM HEPES, 5 mM glucose, 0.1% $NaHCO_3$, and 1 mM EGTA, pH 6.5), and re-suspended in CATCH buffer (PBS and 1.5% bovine serum albumin, 1 mM adenosine, 2 mM theophylline, 0.38% sodium citrate, all from Sigma-Aldrich). Platelet counts were determined using a HemaVet counter (Drew Scientific). Intravital microscopy was performed as previously described (see e.g., Celi et al, *J. Thromb. Haemost.* 1, 60-68 (2003); and Neyman et al, *Blood*, 112, 1101-1108 (2008)). $vWF^{RH\ RH}$NSG male mice were studied after being anesthetized using sodium pentobarbital (80 mg/kg) injected intraperitoneally. Mice were maintained under anesthesia with the same anesthetic delivered via a catheterized jugular vein at 5 mg/mL throughout the experiment. The cremaster muscle was surgically exteriorized and continuously superfused with a physiological buffer (PBS containing 0.9 mM $CaCl_2$ and 0.49 mM $MgCl_2$) maintained at 37° C. throughout the entire experiment and equilibrated with a mixture of 95% $N_2$ and 5% $CO_2$. Human platelets, 400 million per mouse, were labeled with mouse anti-human CD41 F(ab')2 (BD Biosciences) conjugated to Alexa Fluor-488 and infused into the jugular vein, followed by Alexa Fluor-647 rat anti-mouse CD41 F(ab')2 (Thermo Fisher) to detect endogenous mouse platelets (see e.g., Fuentes et al, *J. Clin. Invest.* 126, 483-494 (2016)). Vascular injury was induced with an SRS NL100 pulsed nitrogen dye laser (440 nm) focused on the vessel wall through the microscope objective. Each injury was followed for three minutes. eptifibatide was used at 5 μg/mouse (equivalent to the clinically effective dose of ~1.5 μM (see e.g., Holmes et al, *Am. J. Cardiol.* 84, 203-207 (1999)) and Hr10 at the equimolar concentration (60 μg/mouse). Drugs were infused 5 minutes prior to injury via the jugular vein. Pre and post drug measurements were made in the same animal. Wide-field images of thrombi were recorded using a Hamamatsu ORCA Flash 4.0 V3 CMOS camera (Hamamatsu, Japan) coupled to an Excelitas X-Cite XLED light source. The microscope, cameras, and light sources were all controlled using Slidebook 6.0 software (Intelligent Imaging Innovations). Intensity of the fluorescent signal was used to measure incorporated platelets (see e.g., Neyman et al, *Blood* 112, 1101-1108 (2008)). Eight injuries were made in each of four mice in each group.

Animal Bleeding Studies

Pentobarbital-anesthetized $vWF^{RH\ RH}$NSG mice were infused retroorbitally with $8 \times 10^8$ washed human platelets in a final volume of 200 μL (so that ~40% of the circulating platelets were human). After 5 minutes PBS, 3 μM eptifibatide or Hr10 were administered IV. After another 5 minutes, mouse tail injury was produced by amputating an 8-mm terminal tail segment using a razor blade, which was then placed in a collection tube containing sterile water at 37° C. for 10 minutes. The hemoglobin level in the water was measured by a spectrophotometer, as described (see e.g., Greene et al, *J. Thromb. Haemost.* 8, 2820-2822 (2010)) with the following modifications. Briefly, the hemolyzed whole blood/water mixture was centrifuged at 21,000×g for 5 minutes. Aliquots (20 μL) of clarified, stroma-free supernatant were diluted 10-fold in a Corning 96-well micro-plate and light absorbance measured at 575 nm (Spectramax-190 plate reader, Molecular Devices, San Jose, Calif.). Blood loss during the 10-minute window was measured based on a previously obtained standard curve.

Statistical Calculations

Dose-response experiments for whole blood aggregation and binding to K562 cells were conducted at least three times. Curve-fitting and statistical calculations were performed in SigmaPlot. The data points from each replicate were scaled to one another by an initial fit to a sigmoidal function to determine the minimum and maximum values. Data scaled to a maximum of 1 and a minimum of 0 were combined and fit to a sigmoidal curve to determine the $IC_{50}$ value. The standard error for the $IC_{50}$ estimate was calculated using the reduced $\chi^2$ method. P-values comparing $IC_{50}$s from different inhibitors were determined using the global fit function in SigmaPlot. The two data sets were fit with all parameters separate and again where the $IC_{50}$ value is shared between the data sets. Fisher's F statistic was calculated from the residual sum of squares and degrees of freedom for the unshared ($SS_{un}$, $DF_{un}$) and shared ($SS_{sh}$, $DF_{sh}$) with the equation $F=((SS_{sh}-SS_{un})/(DF_{sh}-DF_{un}))/(SS_{un}/DF_{un})$ and the p-value obtained from the F distribution. Linear regression fits to data from clot retraction experiments proceeded similarly. The Holm-Sidak test following one-way ANOVA (alpha=5.0%) was used to assess if the differences in human platelet accumulation in thrombi between Hr10 and eptifibatide-treated mice were significant. Each time point was analyzed individually, without assuming a consistent standard deviation. For the bleeding studies, the data passed the Shapiro-Wilk normality test and hence compared using the Student's t-test. Number of mice used for bleeding studies was based on the assumption that hemostasis is preserved in 80% of Hr0-treated mice but only 5% of eptifibatide-treated mice (projections supported by published reports of similar studies using eptifibatide, and the predictive clot retraction data). A significance level (p value) of 0.05 is achieved using 4 animals per group, yielding 90% statistical power.

Example 1. Modeling and Chemical Synthesis of Tirofiban Analogs

A pure antagonist of αVβ3 (the RGD-based peptide hFN10; see U.S. Patent Publication No.: US 2017/0044236, the disclosure of which is incorporated herein in its entirety) has been converted into Hr10, a pure bispecific antagonist of both αIIbβ3 and αVβ3, and the crystal structure was determined in complex with αVβ3 integrin. A previously reported tirofiban/β3 integrin complex was superimposed onto the Hr10/integrin complex, as shown in FIG. 1. The ligand Asp1495 of Hr10 and isoAsp of tirofiban superpose, each monodentately ligating the metal ion at MIDAS. Whereas Asp1495 is followed by Trp1496 in Hr10, isoAsp is followed by a sulfonylbutane group in tirofiban, which faces away from Tyr122, whose movement reports the initiating activation cascade of the integrin. Thus, tirofiban allows the activating inward movement of Tyr122 in the tirofiban/integrin complex and explains the partial agonism of tirofiban.

Having observed the proximity of the two amides that follow the respective acidic residues in the two structures (black arrows in FIG. 1), it was hypothesized that replacement of the sulfonylbutane moiety in tirofiban with a 1,3-benzoxazole moiety (which resembles the chemical structure Trp1496) would allow the new moiety to make a π-π interaction with Tyr122 in the inactive conformation (see FIG. 1). Accordingly, three tirofiban analogs (Compounds 1-3) were prepared according to the procedures shown in Scheme 1.

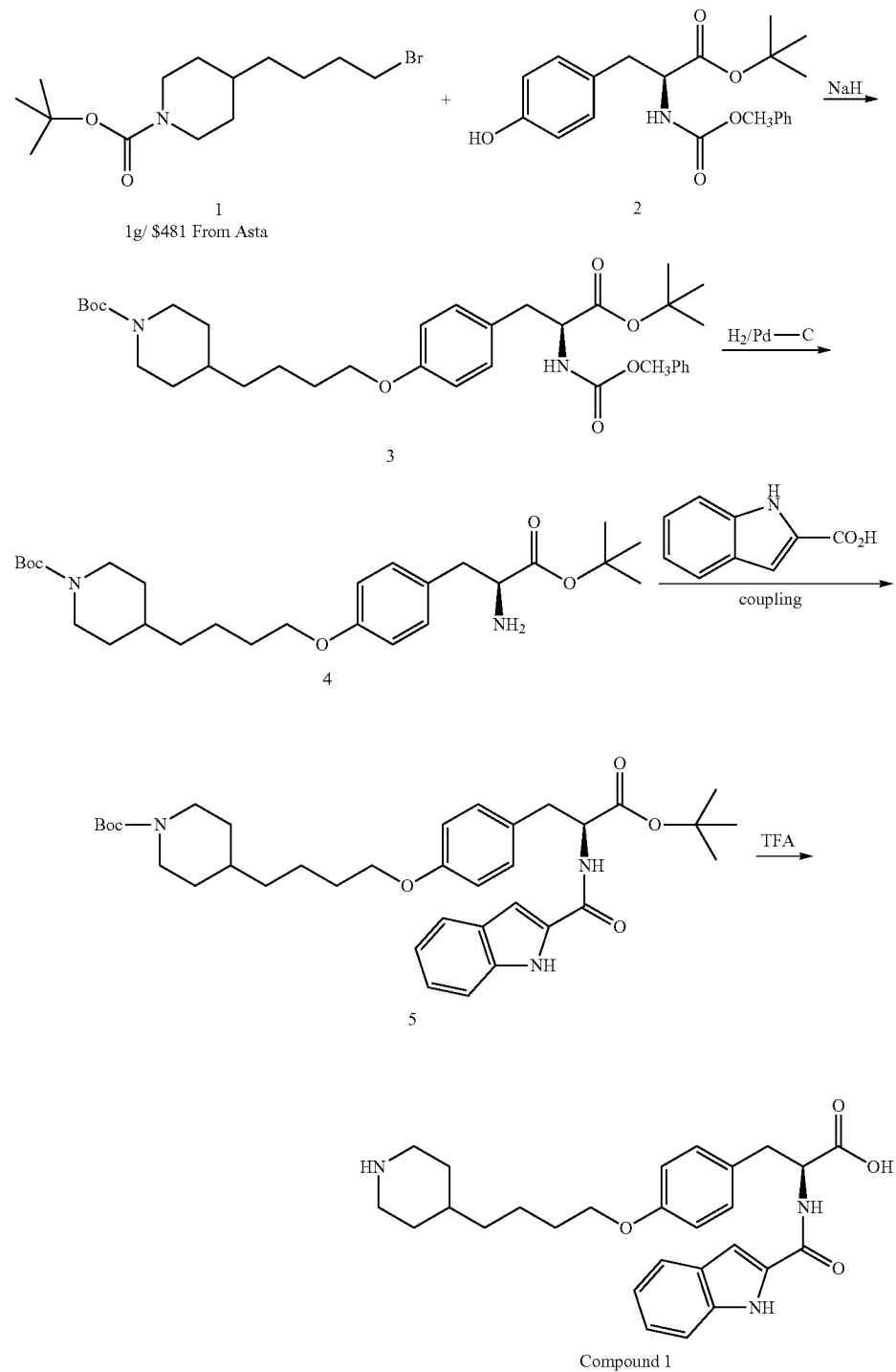

-continued

Compound 2

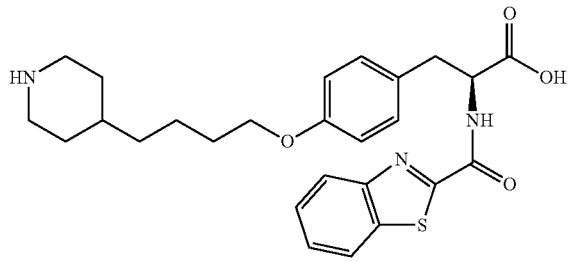

Compound 3

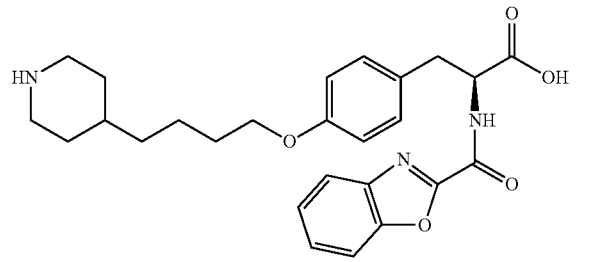

Once prepared, a pilot study that showed that Compound 3 was more effective than Compounds 1-2 in inhibiting human platelet aggregation. Accordingly, Compound 3 was selected for further testing. Without being bound by theory, it is believed that the oxygen in 1,3-benzoxazole of Compound 3 may form a stabilizing H-bond with an amino group in Arg214 of βA.

As shown in FIG. 6A, a structure of this modified tirofiban (i.e., M-tirofiban) in complex with inactive αIIbβ3 (3fcs.pdb) was modeled in Coot (see e.g., Emsley et al, *Acta Crystallogr. D. Biol. Crystallogr.* 66, 486-501 (2010) by geometry minimization with a library generated by eLBOW in Phenix (see e.g., Adams et al, *Acta Crystallogr. D. Biol. Crystallogr.* 66, 213-221 (2010). In this model, the RGD-like moiety of M-tirofiban superimposes on that of tirofiban, with the benzoxazole moiety forming a π-π contact (4.4 Å) with β3-Tyr[112], and the benzoxazole oxygen forming a hydrogen bond (3.2 Å) with Ne of β3-Arg[214], arrangements predicted to freeze the integrin in the inactive conformation.

Example 2. Binding of Compound 3 to Cellular αIIbβ3

Figure 2:
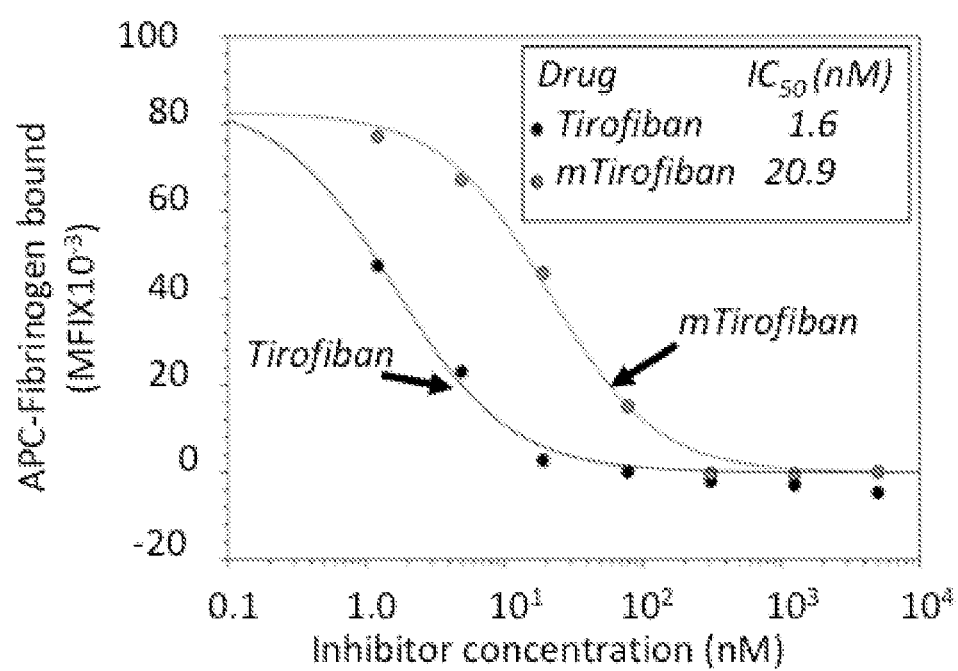
FIG. 2 show inhibition of APC-fibrinogen binding to K562-αIIbβ3 by m-tirofiban and tirofiban.
Figure 3:
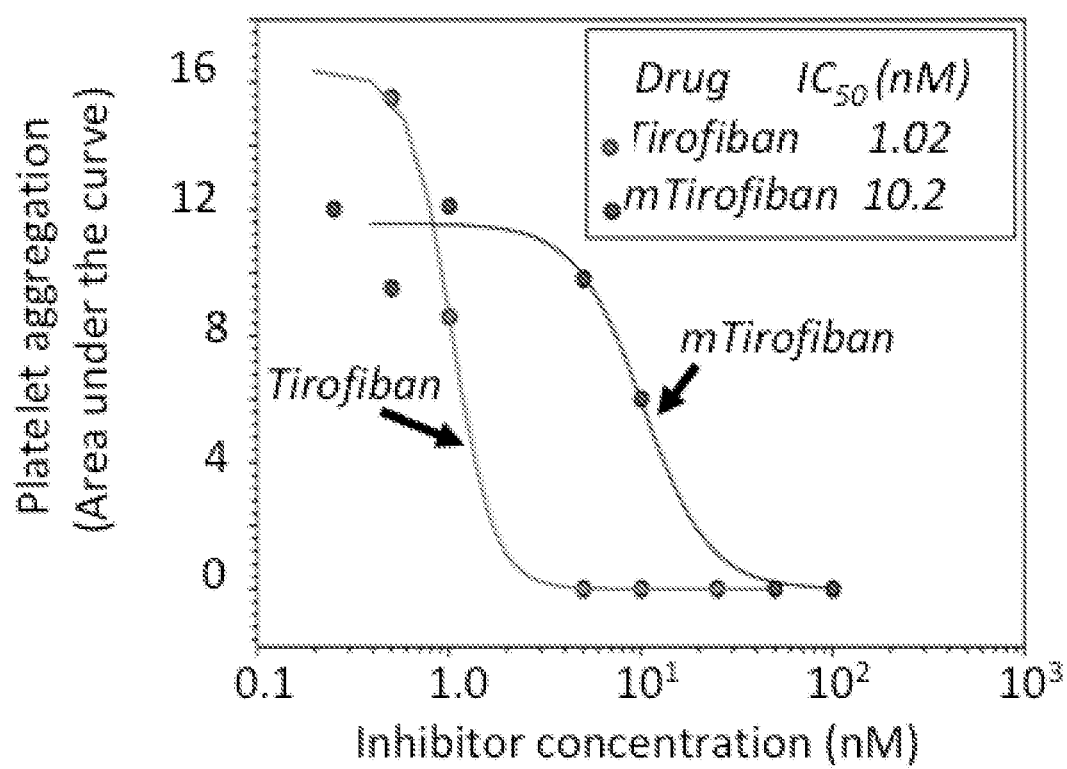
FIG. 3 shows dose response curves comparing the effects of m-tirofiban and tirofiban on ADP-induced platelet aggregation measured by electrical impedance in whole human blood using Chrono-Log 700 Aggregometer.
Figure 6B:
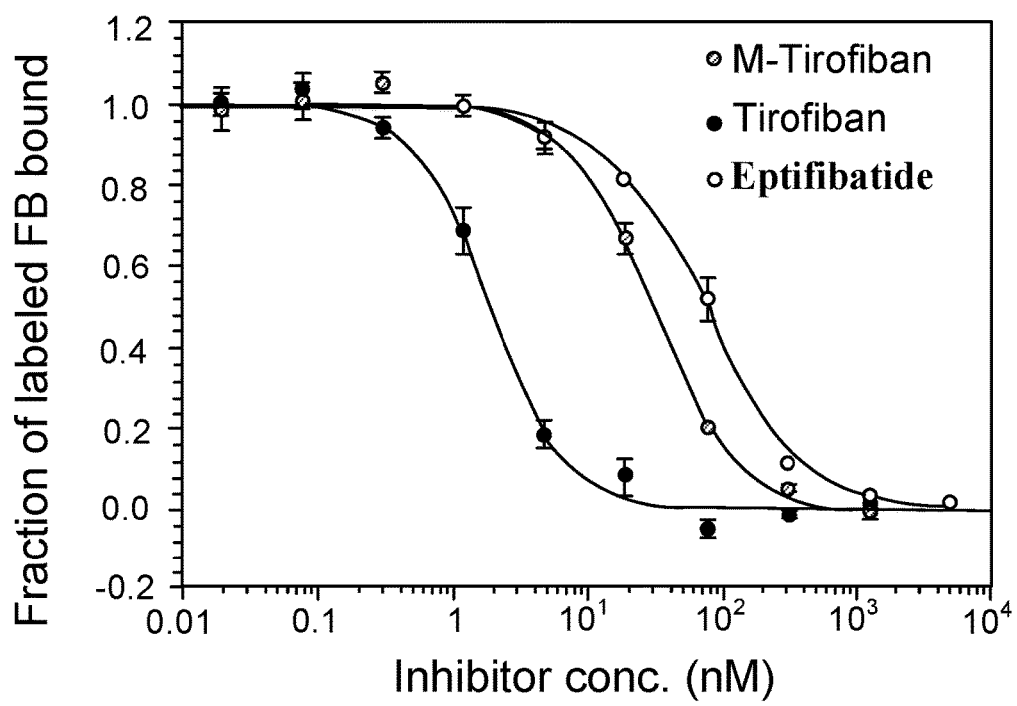
FIG. 6B shows dose response curves (mean±S.E., n=4 experiments) showing displacement of labeled fibrinogen bound to preactivated αIIbβ3-K562 by tirofiban or M-tirofiban yielding $IC_{50}$s of 1.98±0.19 nM, and 30.9±3.3 nM, respectively. Displacement of labeled fibrinogen by eptifibatide is shown for comparison.

APC-labeled fibrinogen binding to K562 stably expressing human αIIbβ3 (K562-αIIbβ3) in presence of increasing concentrations of Compound 3 (i.e., m-tirofiban) or native tirofiban was measured by flow cytometry. As shown in FIGS. 2 and 6B, Compound 3 inhibited binding of APC-fibrinogen to K562-αIIbβ3 in a dose dependent manner.

Example 3. Compound 3 Inhibits Platelet Aggregation

Figure 4:
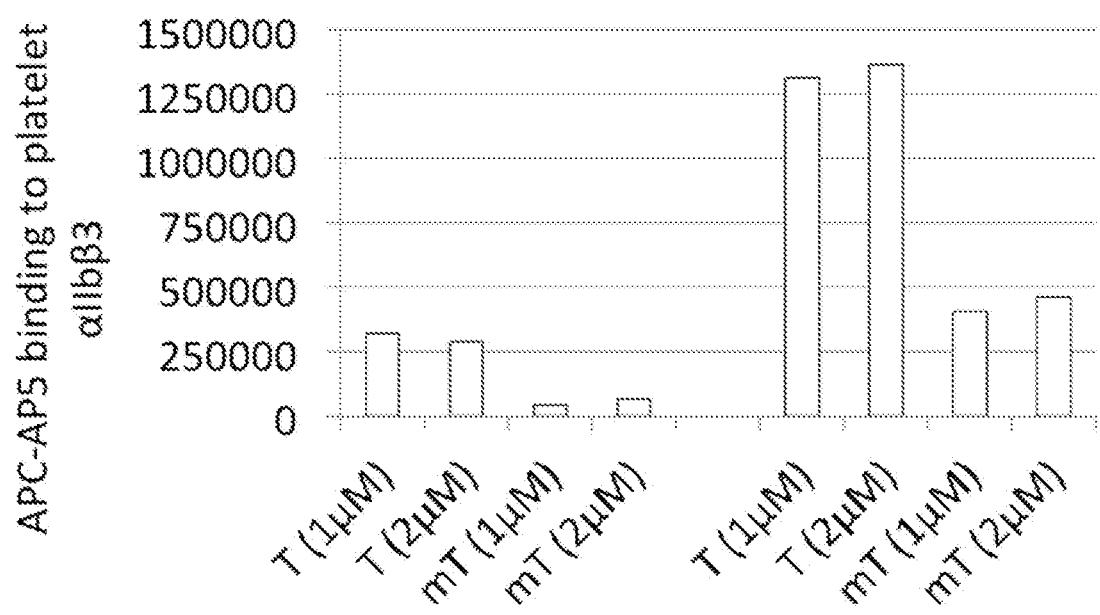
FIG. 4 shows histograms showing binding of APC-labeled AP5 to human platelets in PRP pretreated with saturating concentrations of tirofiban (T) or m-tirofiban (mT) before or 5 minutes after addition of 20 μM ADP. This data shows that m-tirofiban did not induce the activating shape-shifts (conformational changes) in the receptor, i.e., it behaved as "pure" (non-activating) antagonist of αIIbβ3.
Figure 6C:
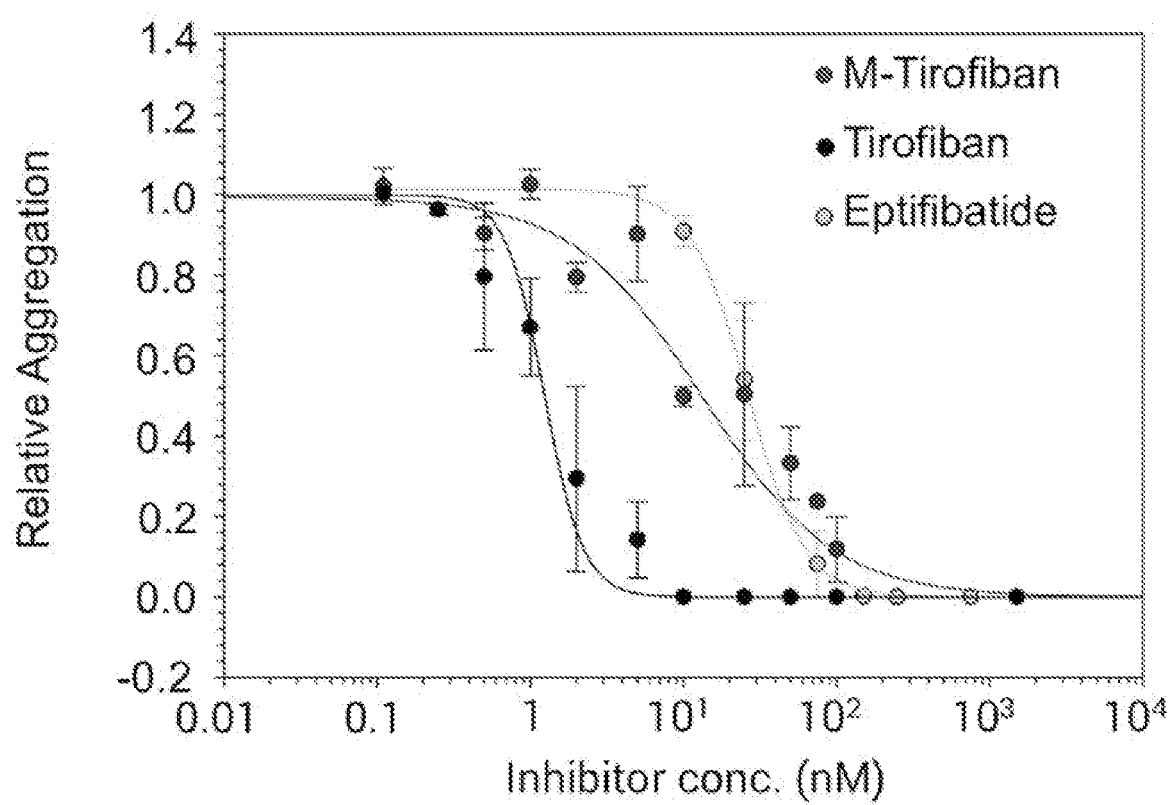
FIG. 6C shows dose response curves (mean±S.E., n=5 experiments) showing effects of tirofiban or M-tirofiban on human platelet aggregation from three different donors induced by ADP (20 μM) yielding $IC_{50}$s of 1.41±0.23 nM and 18.5±5.4 nM, respectively. Effect of eptifibatide on platelet aggregation is shown for comparison.

The effects of Compound 3 vs. tirofiban on ADP-induced aggregation of human platelets in whole blood were analyzed. Platelet aggregation was measured in whole blood by impedance increase with a Chrono-log model 700 according to the manufacturer's protocol. Citrated whole blood was diluted with an equal volume of physiologic saline (Sigma) and incubated for 5 min at 37° C. without stirring. Inhibitors were added to final concentration and the cuvette stirred at 1,200 rpm. Following establishment of stable baseline, ADP (20 µM) was added and tracings recorded for 6 min. The extent of aggregation was determined as the integrated impedance over 5 min. As shown in FIGS. 4, and 6B-6C, Compound 3 inhibited platelet aggregation in a dose-dependent manner but with lower affinity compared to tirofiban, which was consistent with the fibrinogen displacement study data shown in FIG. 2. Prevention of ADP-induced human platelet aggregation (see FIG. 6C) was observed in the low nanomolar range (~18-30 nM), compared with 1.5-2 nM for tirofiban. Without being bound by theory, it is believed that the ~10-fold reduction in affinity of M-tirofiban vs. tirofiban likely reflects weaker H-bonding of the benzoxazole oxygen vs. the sulfonamide oxygen of tirofiban with Ne of β3-Arg[214], and perhaps loss of hydrophobic contacts of the deleted butane moiety with the integrin. The affinity of M-tirofiban calculated in these assays was equivalent to that of the drug eptifibatide, as shown in FIGS. 6B-6C.

Figure 6D:
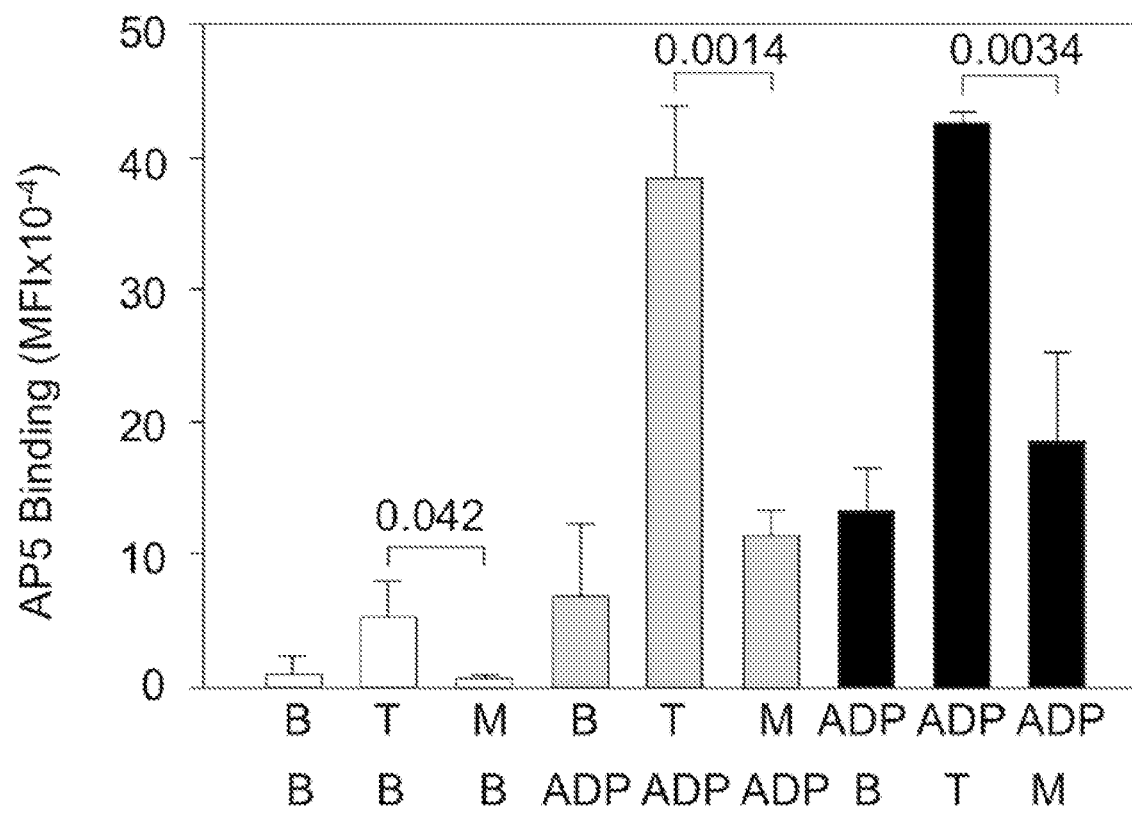
FIG. 6D shows histograms (mean±S.D., n=3 independent experiments) showing binding of AP5 mAb to human platelets in presence of buffer (B), tirofiban (T; 150 nM) and M-tirofiban (M; 1.5 µM) (white histograms) alone, and before (gray histograms) or after (black histograms) addition of ADP (5 µM). Numbers represent p-values. No significant differences were found between B and M before (p=0.273) or after (p=0.81) ADP addition.
Figure 6E:
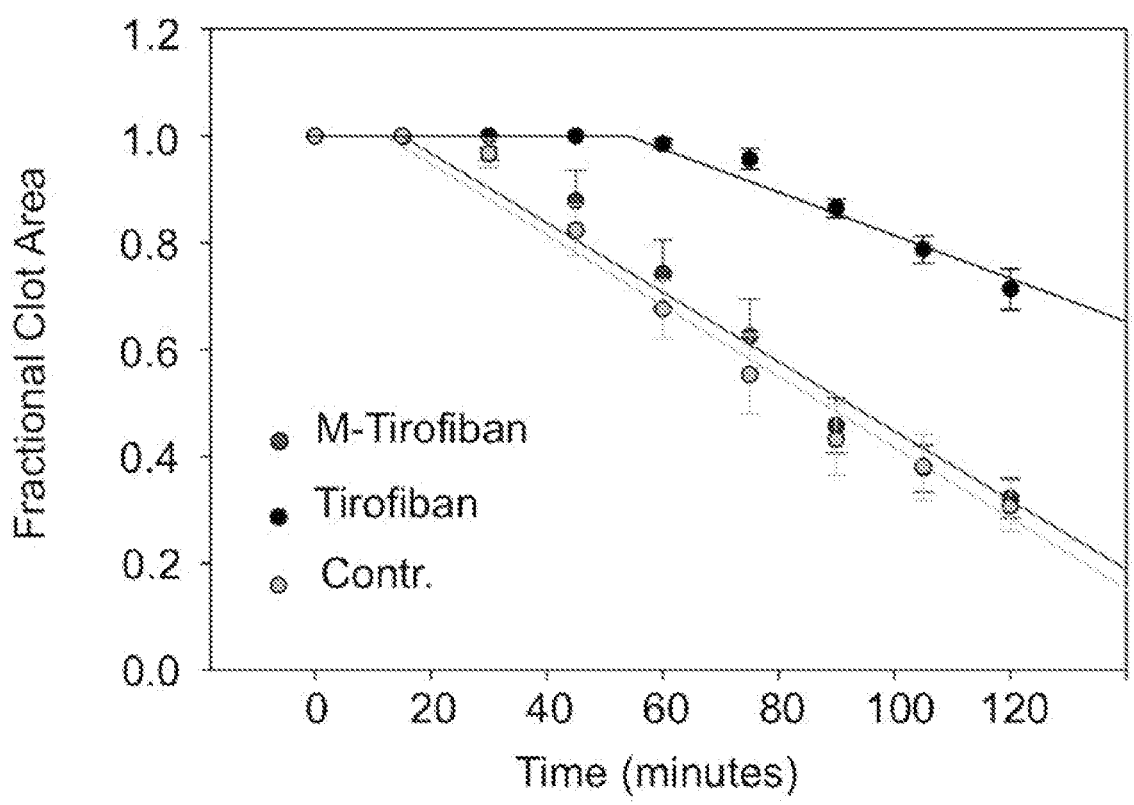
FIG. 6E shows kinetics of clot retraction in the absence or presence of tirofiban, or M-tirofiban (mean±S.E.) from three experiments. Kinetics of clot retraction was not different between buffer control (contr.) and M-tirofiban (p=0.61).
Figure 6F:
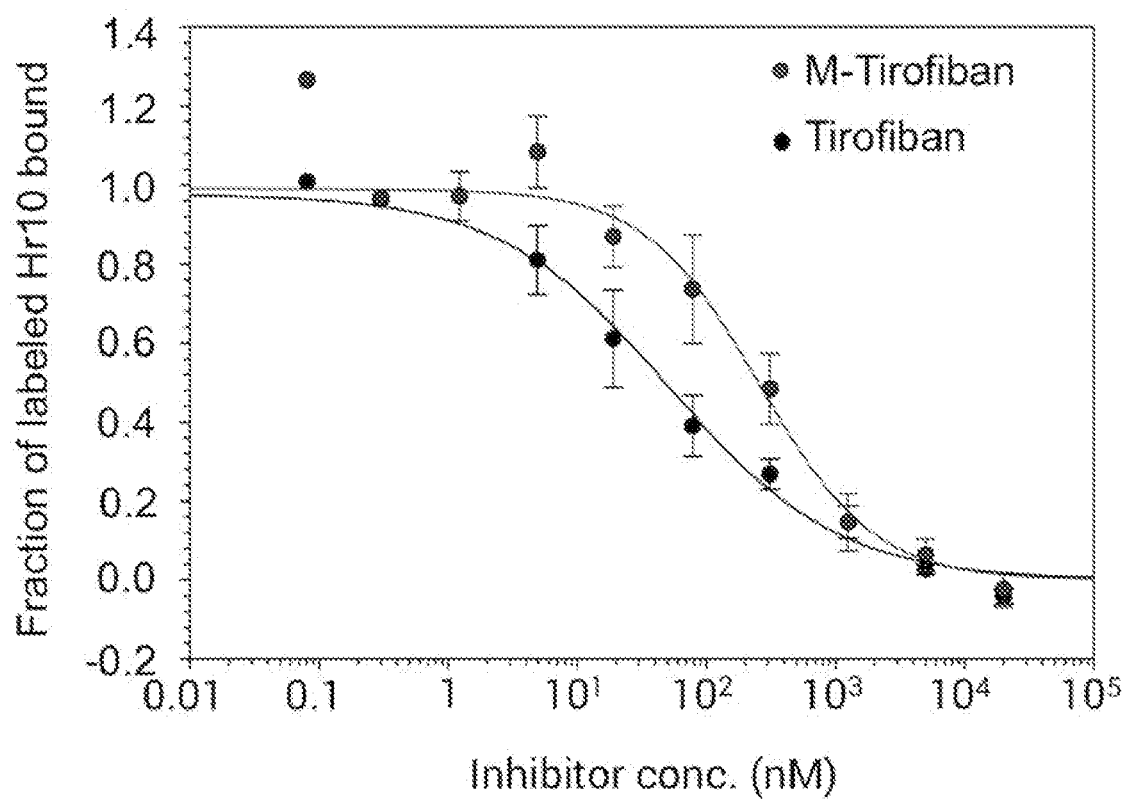
FIGS. 6F-6G show dose response curves (mean±S.E.) comparing displacement of Alexa488-labeled Hr10 binding to inactive (f, n=5) and mAb PT-25-activated αIIbβ3-K562 (g, n=3) by increasing concentrations of tirofiban or M-tirofiban in presence of physiologic concentrations of $Mg^{2+}$ and $Ca^{2+}$ (1 mM each). The respective $IC_{50}$s were 51.3±19.2 nM, and 257.2±88.0 nM for inactive and 16.9±2.4 nM and 247.1±29.3 nM for active αIIbβ3. The lower affinities of both compounds are explained by the requirement for more inhibitor to displace high affinity binding of Hr10 (compared to fibrinogen as shown in FIG. 6B) to αIIbβ3.
Figure 6G:
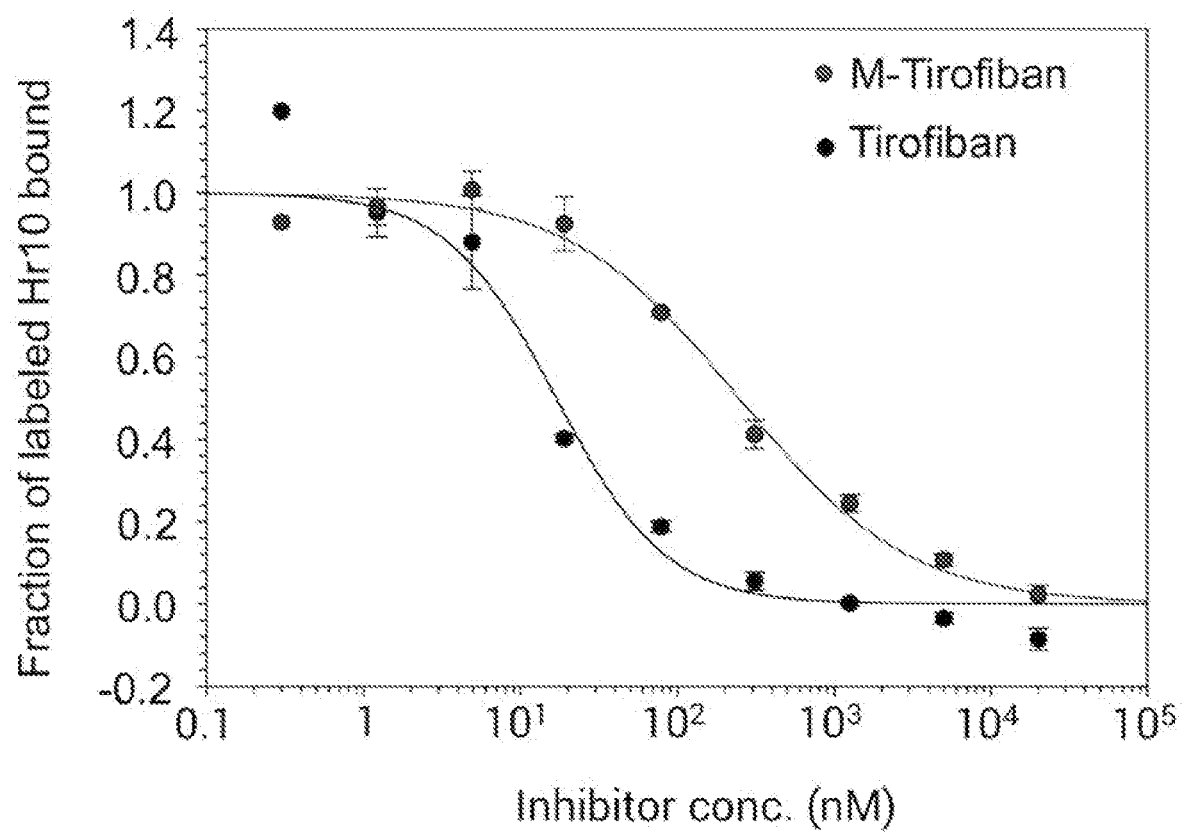

Binding of tirofiban to αIIbβ3 at the clinically effective concentration of 150 nM (see e.g., Bougie et al, *Blood* 100, 2071-2076 (2002)) induced expression of the AP5 epitope, which was markedly increased upon addition of ADP or when tirofiban is added after platelet exposure to ADP, as shown in FIG. 6D. In contrast, M-tirofiban (at the equipotent concentration of 1.5 µM) did not induce AP5 expression, prevented that induced by subsequent addition of ADP and even suppressed ADP-induced AP5 expression when M-tirofiban was added afterwards, as shown in FIG. 6D). While tirofiban effectively blocked thrombin-induced clot retraction, M-tirofiban did not, as shown in FIG. 6E, and showed equivalent binding affinities to inactive and active αIIbβ3, as shown in FIGS. 6F-6G.

Example 4. Compound 3 is a Pure Orthosteric Antagonist of αIIbβ3

In contrast to tirofiban, binding of Compound 3 to human platelets in PRP (each used in saturating amounts), in the absence or presence of 20 µM ADP, did not induce the activating conformational changes in αIIbβ3 as reported by binding of the conformation-sensitive mAb AP5 (see FIG. 4). These preliminary data show the feasibility of using the Hr10/integrin structure to convert small molecule inhibitors of αIIbβ3 into pure integrin antagonists. Without being bound by theory, it is believed that the lower affinity of Compound 3 vs. tirofiban can be improved by introducing structural modifications to extend the reach of the oxygen atom in the indole group for stronger H-bonding to Arg214 in the integrin. Exemplary structural modifications include, but are not limited to, replacement of the 1,3-benzoxazole moiety with an indole, indoline, benzothiazole, or benzoxazole moiety.

Example 5. Compound 3 does not Inhibit Clot Retraction

Figure 5A:
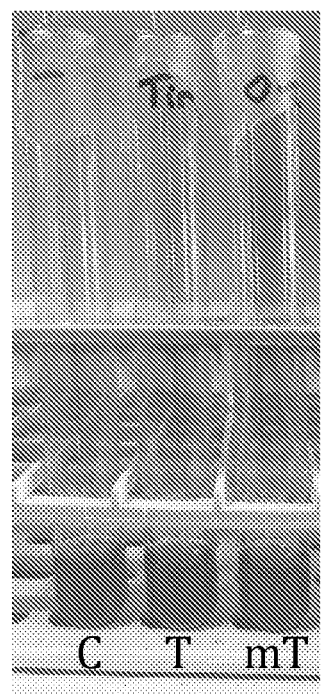
FIG. 5 shows photographs comparing the effects of tirofiban (T; 1.5 μM) and m-tirofiban (mT; 15 μM) on normal clot retraction induced by addition of α-thrombin (0.5 unit/mL; Chrono-Log). No ligands were added to the control tube. Photographs were taken immediately after thrombin addition (FIG. 5A) and at the end of the reaction (FIG. 5B). Clot retraction around the central glass rod placed in each glass test tube before thrombin addition is shown. 5 μL of red blood cells were added per 1 mL reaction to enhance the color contrast for photography. At the concentrations used, tirofiban completely blocked clot retraction, accounting for its ability to potentially cause serious bleeding in treated patients. In contrast, m-tirofiban, at the equivalent concentration, reduced clot retraction minimally (compared with the control).
Figure 5B:
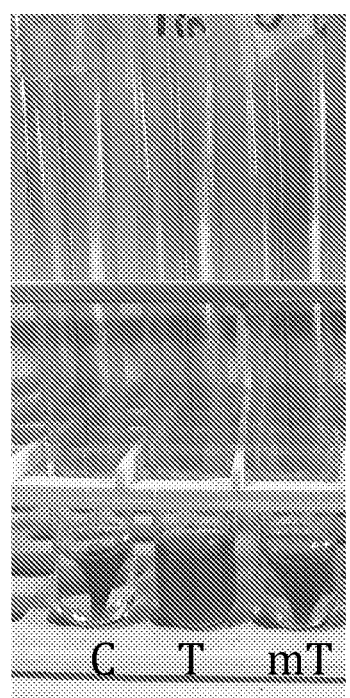

FIG. 5 shows photographs comparing the effects of tirofiban (T; 1.5 µM) and m-tirofiban (mT; 15 µM) on normal clot retraction induced by addition of α-thrombin (0.5 unit/mL; Chrono-Log). No ligands were added to the control tube. Photographs were taken immediately after thrombin addition (FIG. 5A) and at the end of the reaction (FIG. 5B). Clot retraction around the central glass rod placed in each glass test tube before thrombin addition is shown. 5 µL of red blood cells were added per 1 mL reaction to enhance the color contrast for photography. At the concentrations used, tirofiban completely blocked clot retraction, accounting for its ability to potentially cause serious bleeding in treated patients. In contrast, m-tirofiban, at the equivalent concentration, reduced clot retraction minimally (compared with the control).

Example 6. Structure-Guided Conversion of Partial Integrin Antagonists into Pure Integrin Antagonists Using the general modeling procedures described in Example 6, a representative group of partial integrin antagonists was modeled to illustrate the conversion of partial antagonists to pure antagonists. The following compounds were exemplified as models for modification to produce pure integrin antagonists and crystal structure data are shown in FIGS. 7A-7F.

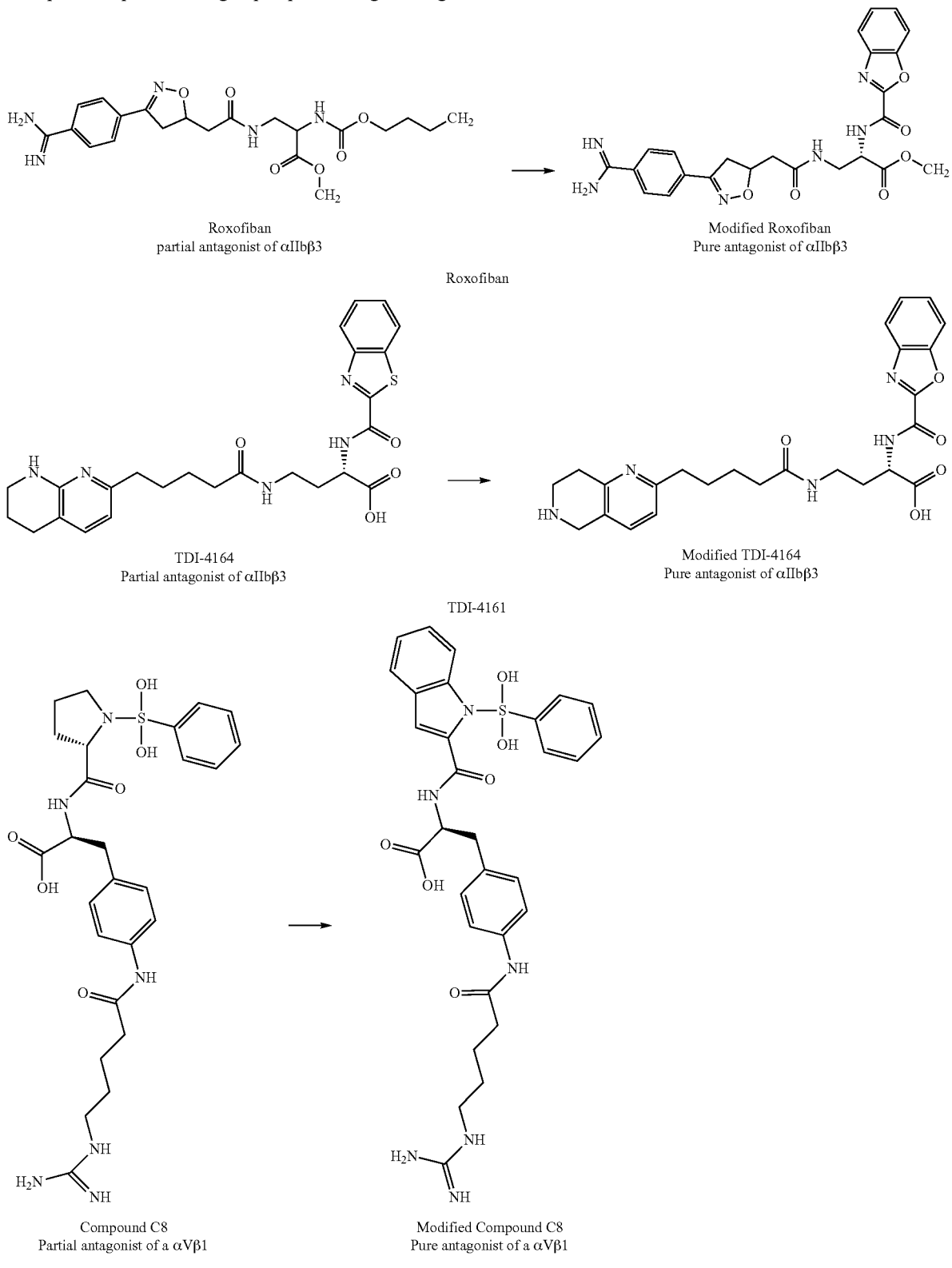

-continued
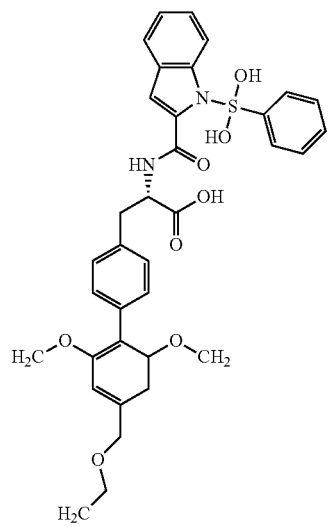
Modified Firategrast
Pure antagonist of α4β1
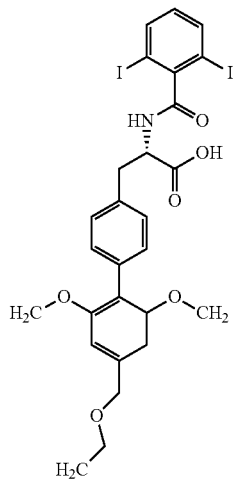
Firategrast
Partial antagonist of α4β1
Firategrast
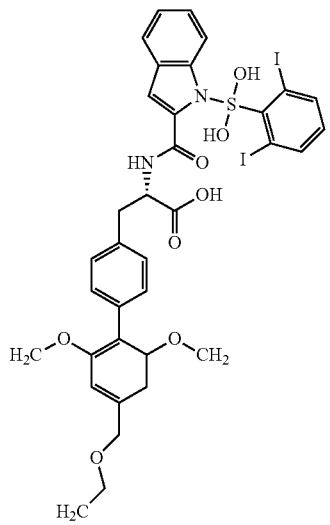
Modified Firategrast
Pure antagonist of α4β1
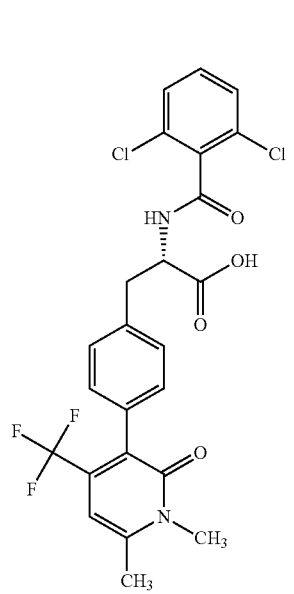
RO0505376
Partial antagonist of α4β7
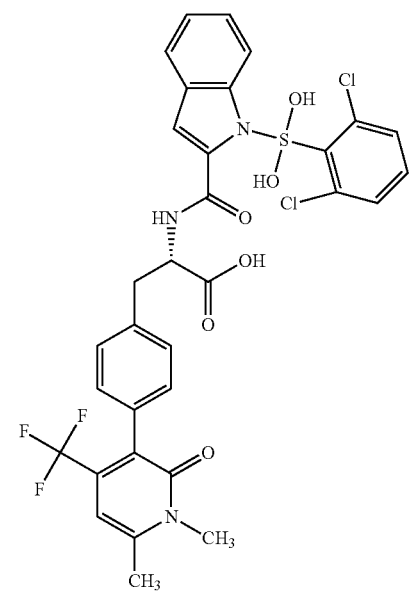
Modified RO0505376
Pure antagonist of α4β7
RO0505376

-continued
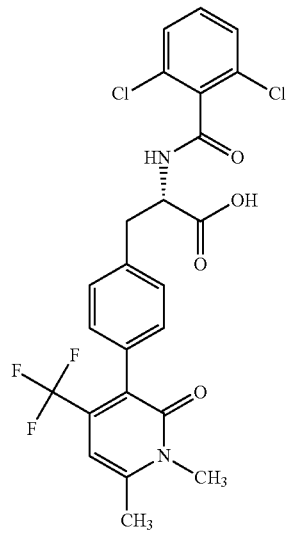
RO0505376
Partial antagonist of α4β7
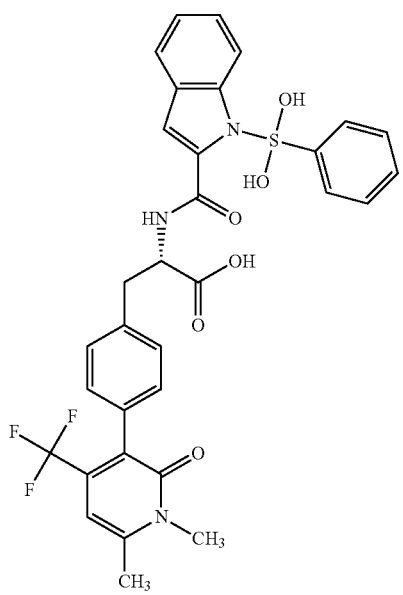
Modified RO0505376
Pure antagonist of α4β7
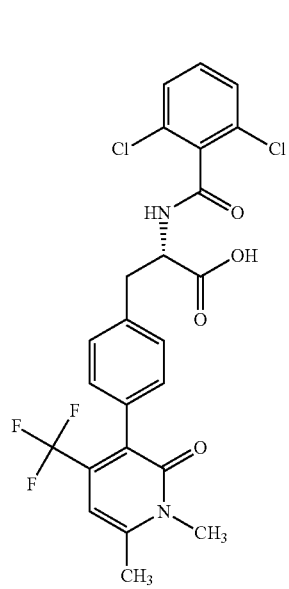
RO0505376
Partial antagonist of α4β7
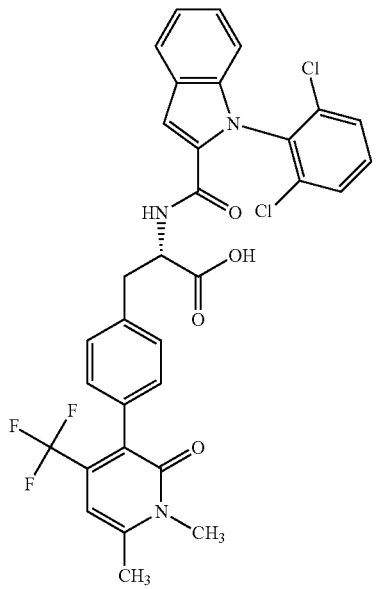
Modified RO0505376
Pure antagonist of α4β7

-continued

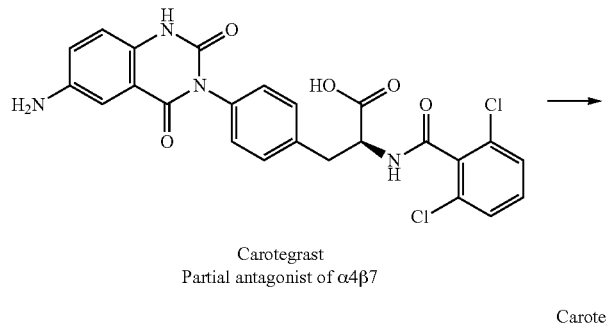

Carotegrast
Partial antagonist of α4β7

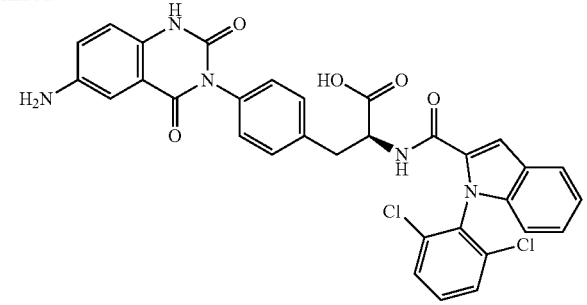

Carotegrast
Pure antagonist of α4β7

Carotegrast

Example 7. Polypeptide Hr10

The inability of hFN10 to bind αIIbβ3 (see e.g., Richards et al, *J. Mol. Biol.* 326, 1475-1488 (2003)) was investigated by superimposing the βA domains from the crystal structures of αIIbβ3/eptifibatide complex (2vdn.pdb) and αVβ3/hFN10, as shown in FIG. 8A. This revealed a potential clash between hFN10 and αIIb propeller involving Serino-Lys in the C-terminal F-G loop of hFN10 and Val$^{156}$-Glu in the longer helix-containing D2-A3 loop of αIIb. In addition, the hFN10 ligand Arg$^{1493}$ could not make the critical bidentate salt bridge with αIIb-Asp$^{224}$. Ser$^{1500}$-Lys in hFN10 was therefore substituted with Gly, and the ligand Arg$^{1493}$ was replaced with the longer L-homoarginine (Ilar), changes that were predicted would not adversely affect FN10 folding or the π-π interaction between β3-Tyr$^{122}$ and Trp$^{1496}$ of the modified peptide Hr10. The presence of Har in Hr10 was confirmed by Mass spectroscopy, as shown in FIGS. 9A-9C.

Figure 8B:
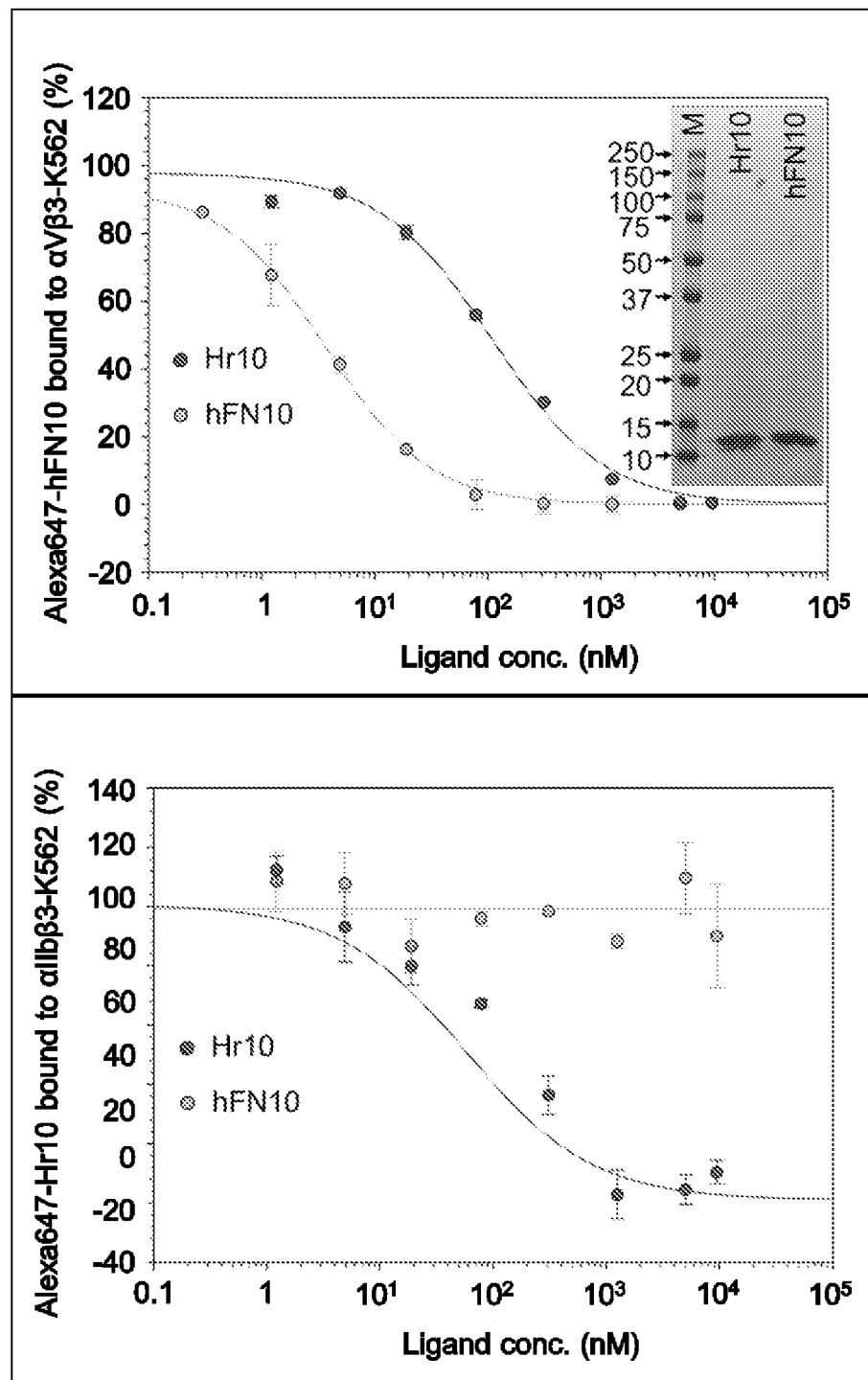
FIG. 8B shows affinity of Hr10 and hFN10 to αVβ and αIIbβ3. The top pane shows dose response curves comparing displacement of Alexa647-labeled hFN10 binding to αVβ3-K562 cells by unlabeled hFN10 or Hr10, yielding $IC_{50}$ values of 3.6±0.72 nM and 107.9±23.1 nM (mean±S.D.), respectively. Cell binding was analyzed by FACS. The mean fluorescence intensity values for individual experiments (n=3) were initially fit with a binding curve to determine minimum and maximum MFI values to use in scaling the data. The points and error bars indicate the mean and standard error for the scaled data. The lines are a least squares fit to the averages. The inset shows a Coomassie stain of 10-20% SDS PAGE showing purified Hr10 and hFN10 (8 µg in each lane). MW markers (in kDa) are indicated. The bottom pane shows dose response curves comparing displacement of Alexa647-labeled Hr10 binding to inactive αIIbβ3-K562 cells by unlabeled Hr10 yielding $IC_{50}$ value of 58.8±24.1 nM (mean±S.D., n=3 independent experiments). No displacement was observed with hFN10. Data was generated as described above for the top pane.
Figure 8C:
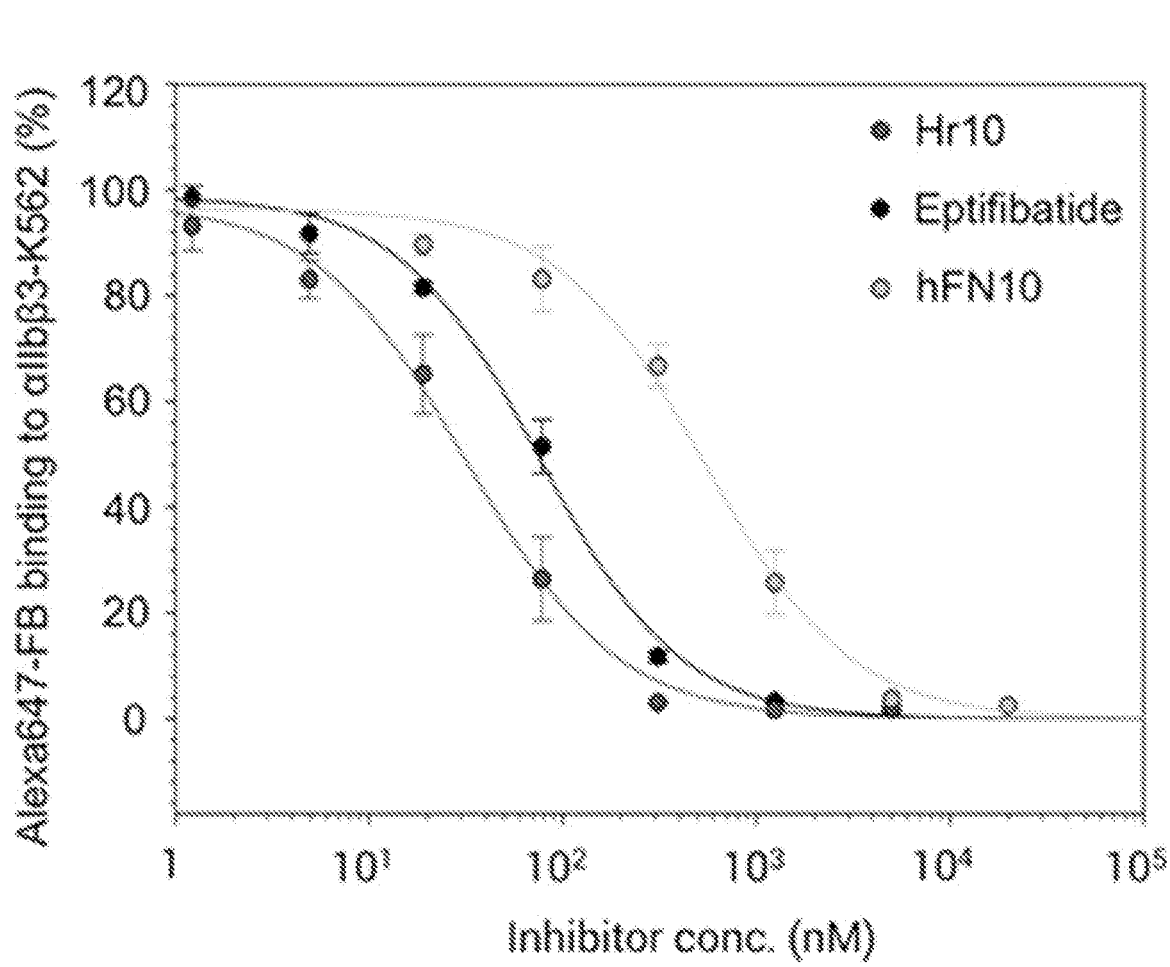
FIG. 8C shows dose response curves (mean±S.E., n=3 independent experiments) generated from FACS analyses showing displacement of Alexa-647 labeled fibrinogen (FB) bound to preactivated αIIbβ3-K562 in the presence of increasing concentrations of unlabeled Hr10, eptifibatide or hFN10. The MFI values from the three separate FACS analyses were normalized individually before averaging as described herein.

Hr10 was verified as a pure antagonist of αIIbβ3. Purified Hr10, but not hFN10, bound K562 cells stably expressing recombinant αIIbβ3 (αIIbβ3-K562), as shown in FIG. 8B, and maintained its binding to αVβ3-K562, as shown in FIG. 8B. Hr10 inhibited binding of Alexa647-labeled soluble FB to activated αIIbβ3 more effectively than eptifibatide (IC$_{50}$ 30.3:k 4.8 nM [mean±S.E., n=3] vs. 73.2 t 7.0 nM for eptifibatide, p=1.79×10$^5$), as shown in FIG. 8C. hFN10 bound minimally to activated αIIbβ3-K562, with an order of magnitude higher IC$_{50}$ of 474.0±73.4 nM, as shown in FIG. 8C.

Figure 8D:
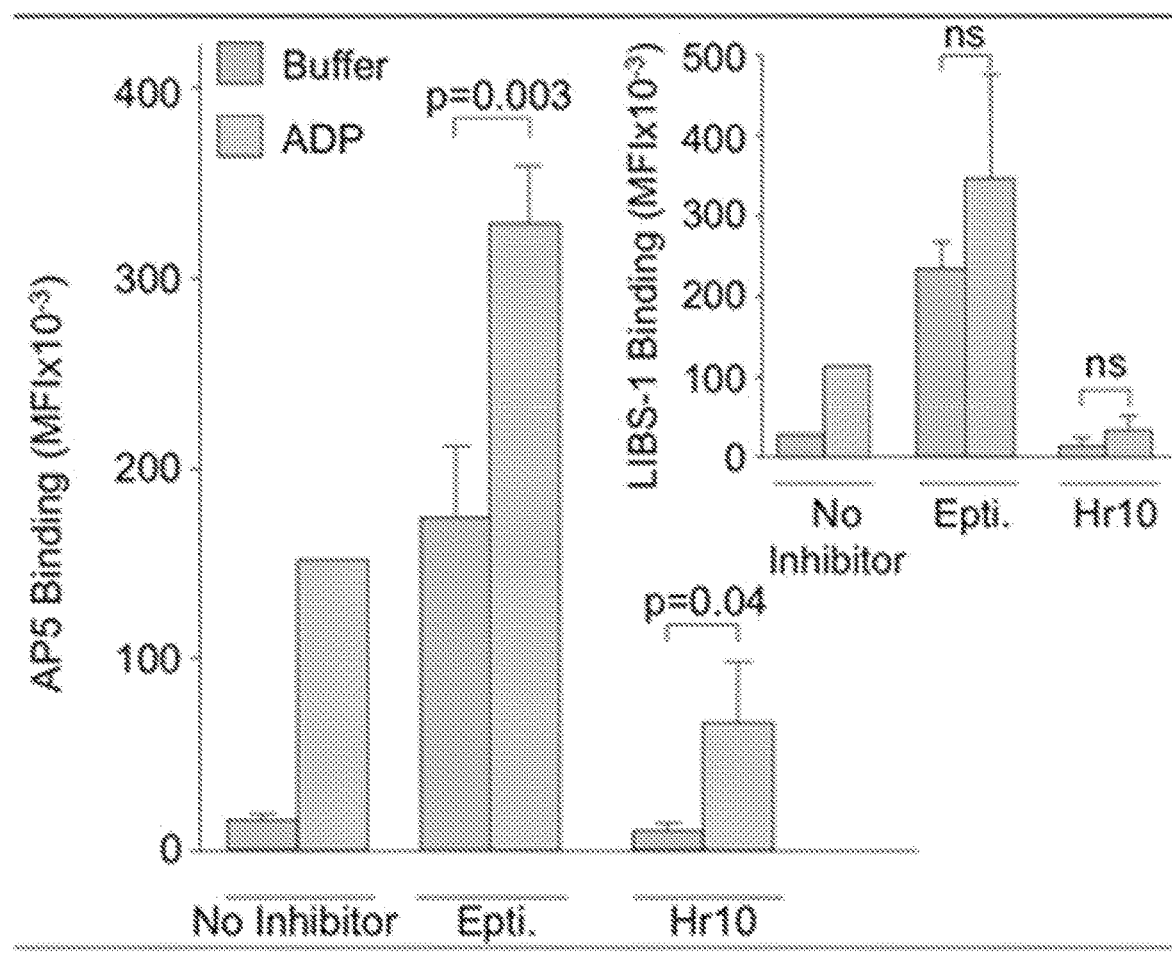
FIG. 8D shows histograms (mean±S.D., n=3 experiments) showing effects of Hr10 vs. eptifibatide (each at 1.5 µM) on integrin conformational changes. Binding of the activation-sensitive mAb AP5 or the extension-sensitive mAb LIBS-1 (inset) to human platelets in the absence or presence of ADP (5 µM) was assessed following flow cytometry.

Binding of eptifibatide (1.5 μM) to human platelets in the absence or presence of 5 μM ADP induced conformational changes in αIIbβ3 reported by binding of the activation-sensitive and extension-sensitive mAbs AP5 and LIBS-1, respectively, shown in FIG. 8D (see e.g., Van Agthoven et al, *Nat. Struct. Mol. Biol.* 21, 383-388 (2014)). In contrast, binding of Hr10 (1.5 μM) did not induce these changes, and suppressed AP5 and LIBS-1 binding to ADP-activated platelets, as shown in FIG. 8D. Thus Hr10 was shown to act as a pure antagonist of αIIbβ3.

Example 8. Crystal Structure of Hr10/β3 Integrin Complex

To elucidate the structural basis of pure antagonism, we determined the crystal structure of the Hr10/integrin complex at 3.1 Å resolution, as shown in FIG. 10A and Table 1, by soaking Hr10 into preformed αVβ3 ectodomain crystals (crystal packing of the αIIbβ3 ectodomain does not allow access of large ligands to MIDAS). The structure confirmed presence of the homoarginine at position 1493 in Hr10. Har$^{1493}$ forms a bidentate salt bridge with αV-Asp$^{218}$ and a cation-π interaction with αV-Tyr$^{178}$, but did not contact αV-Thr$^{212}$ (which replaced αIIb-Asp$^{224}$). The ligand Asp$^{1495}$ directly coordinated the metal ion at MIDAS, with Trp$^{1496}$ making a π-π interaction with βA-Tyr$^{122}$, stabilized by an π-π interaction with βA-Met$^{180}$, as shown in FIG. 10A, and a critical hydrogen bond between the carbonyl of Trp$^{1496}$ and Nε of βA-Arg$^{214}$. Bound Hr10 prevented the activating inward movement of the al helix (reported by β-Tyr$^{122}$) towards MIDAS, and the conformational changes at the C-terminal end of βA domain, which trigger integrin extension. Superposition of the βA domains from the Hr10/αVβ3 and eptifibatide/αIIbβ3 structures, as shown in FIG. 10B, show that the Ser$^{1500}$-Lys/Gly substitution removed the predicted clash with the αIIb propeller. The Nε, Nh1 and Nh2 amino groups of the ligand Har$^{1493}$ superposed well on those of Har$^2$ in eptifibatide, and could likewise form the critical bidentate salt bridge with αIIb-Asp$^{224}$, accounting for the high affinity binding of Hr10 to αIIbβ3. β3-Tyr$^{122}$ was replaced with Phe$^{122}$ in mouse β3, and the stabilizing salt bridge β3-Arg$^{214}$ makes with β3-Asp$^{179}$ was replaced with a H-bond with β3-Asn$^{179}$ in mouse, both substitutions likely contributing to the poor binding of Hr10 to mouse αIIbβ3.

TABLE 1

| Data collection | αVβ3/Hr10 |
|---|---|
| PDB Code | 6NAJ |
| Beamline | ID19 at APS |
| Space group | P3$_2$21 |
| Unit cell dimensions (Å, °) | a = b = 129.7, c = 308.2; |
|  | α = β = 90, γ = 120 |
| Resolution range (Å) | 50-3.1 |
| Wavelength (Å) | 0.97932 |
| Total reflections | 1,044,981 |
| Unique reflections | 55,225 (5,444)* |
| Completeness | 100 (100) |
| Redundancy | 8.2 (8.0) |
| Molecules in asymmetric unit 1 | |
| Average I/σ | 24.9 (2.0) |
| R$_{merge}$ (%) | 9.7 (100) |
| R$_{meas}$ (%) | 10.3 (100) |
| R$_{sym}$ (%) | 3.6 (38.8) |
| Wilson B-factor | 59.6 |

TABLE 1-continued

| Data collection | αVβ3/Hr10 |
|---|---|
| Refinement statistics | |
| Resolution range (Å) | 49.2-3.1 |
| $R_{factor}$ (%) | 24.9 (33.9) |
| $R_{free}$ (%)# | 27.4 (38.9) |
| No. of atoms | 13,498 |
| Protein | 13,137 |
| Water | 4 |
| $Mn^{2+}$ | 8 |
| Glc-NAc | 349 |
| Average B-factor | |
| for all atoms (Å$^2$) | 71.1 |
| r.m.s. deviations | |
| Bond lengths (Å) | 0.004 |
| Bond angles (°) | 1.03 |
| Ramachandran plot | |
| Most favored (%) | 90.9 |
| Allowed regions (%) | 8.7 |
| Outliers (%) | 0.4 |
| Clashscore (%) | 7.7 |

Example 9. Effects of Hr10 on Human Platelet Aggregation and Secretion

Figure 11A:
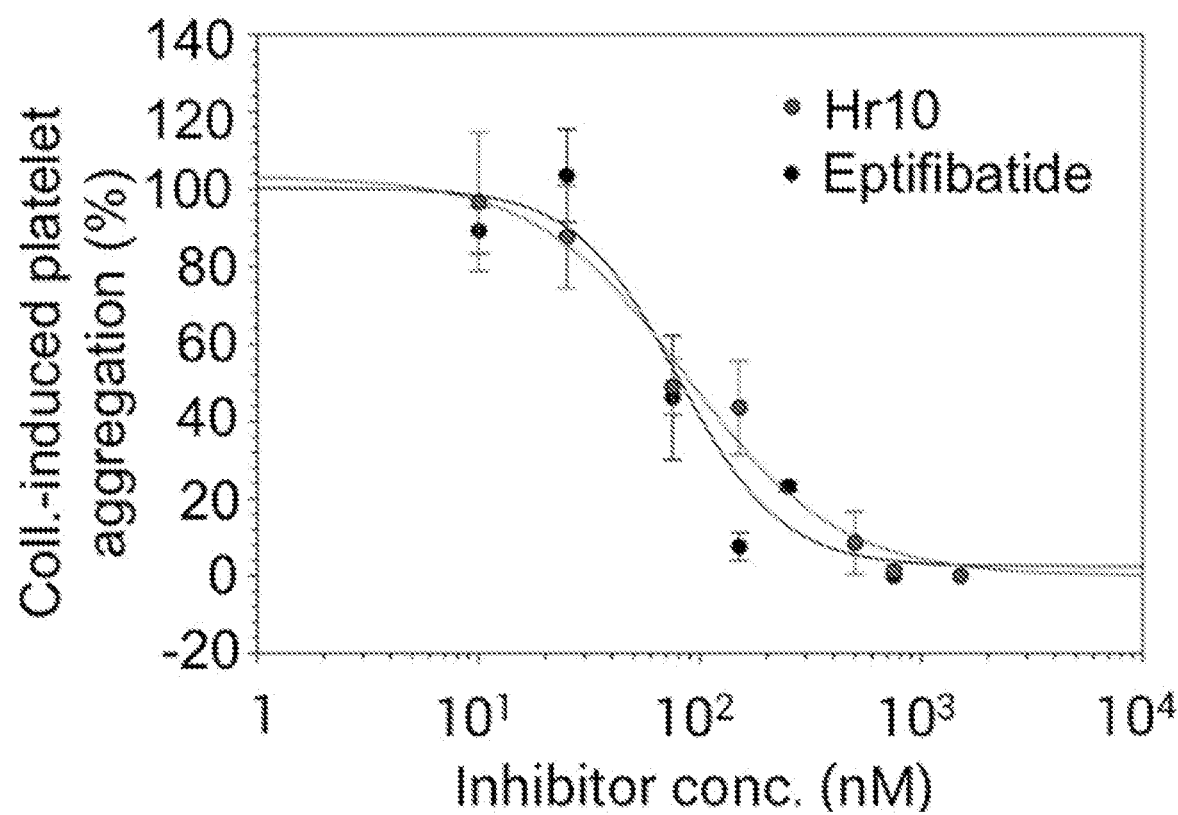
FIGS. 11A-11C show dose response curves (mean S.E., n=3 experiments from 3 different donors) showing effects of the inhibitors on aggregation induced by collagen (2 µg/mL) (FIG. 11A), ADP (20 µM) (FIG. 11B), or TRAP (10 µM) (FIG. 11C). Points for the integrated impedance from the three experiments were individually normalized prior to averaging and are displayed with least-squares fits to the mean values.
Figure 11B:
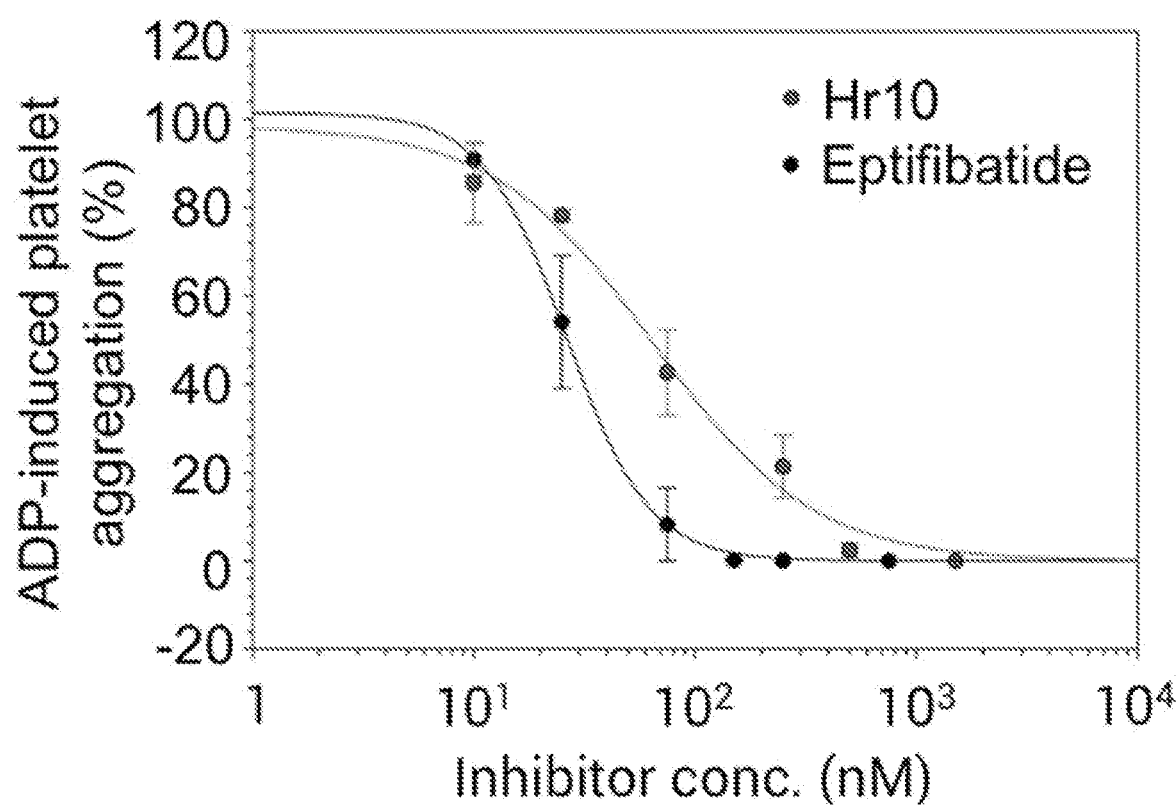
Figure 11C:
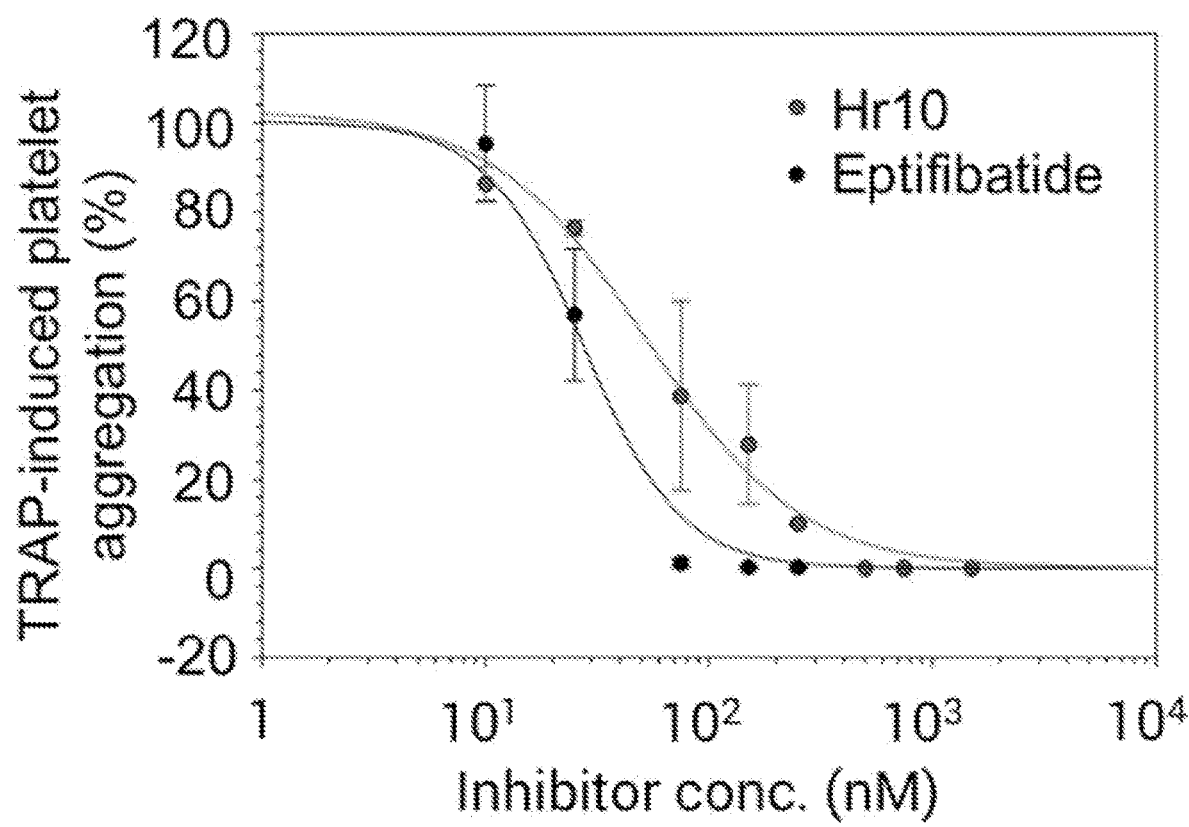
Figure 11E:
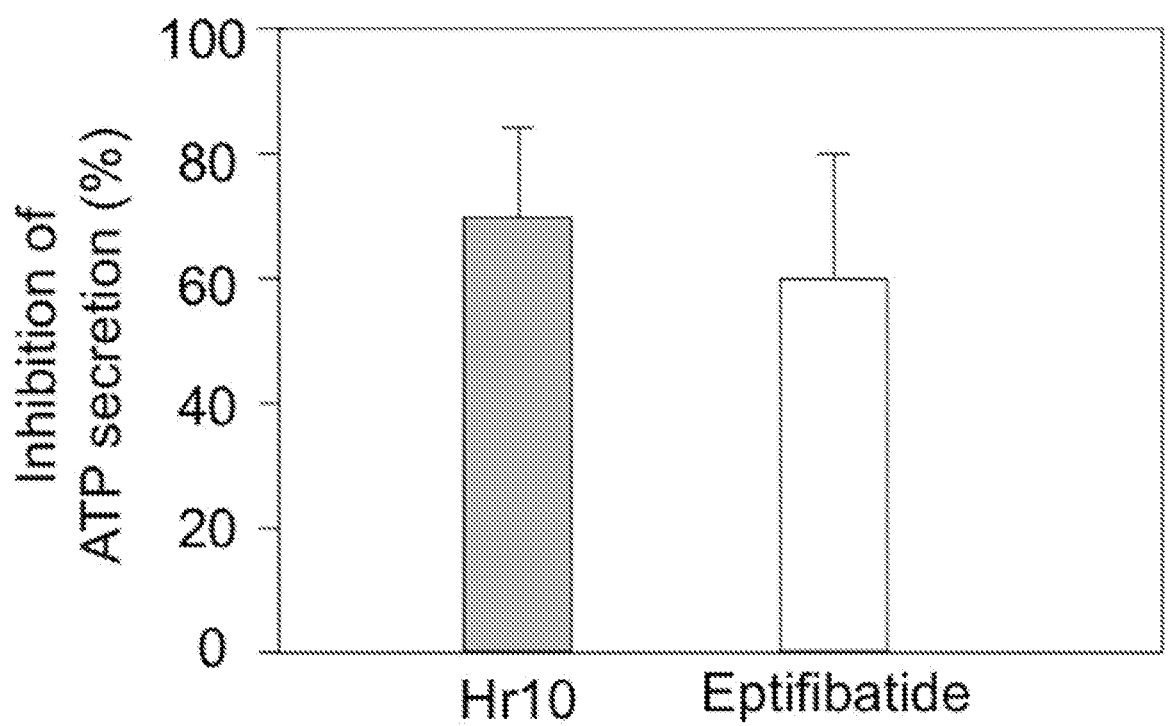
FIGS. 11E-11F show histograms (mean±S.D., n=3) showing the effect of Hr10 and eptifibatide (each at 1.5 µM) on ADP (20 µM)-induced ATP secretion (FIG. 11E; p=0.5) and surface expression of CD63 and CD62P (FIG. 11F) in human platelets. No differences in expression of CD63 (p=0.15) or CD62P (p=0.72) were found in platelets exposed to eptifibatide or Hr10.
Figure 11F:
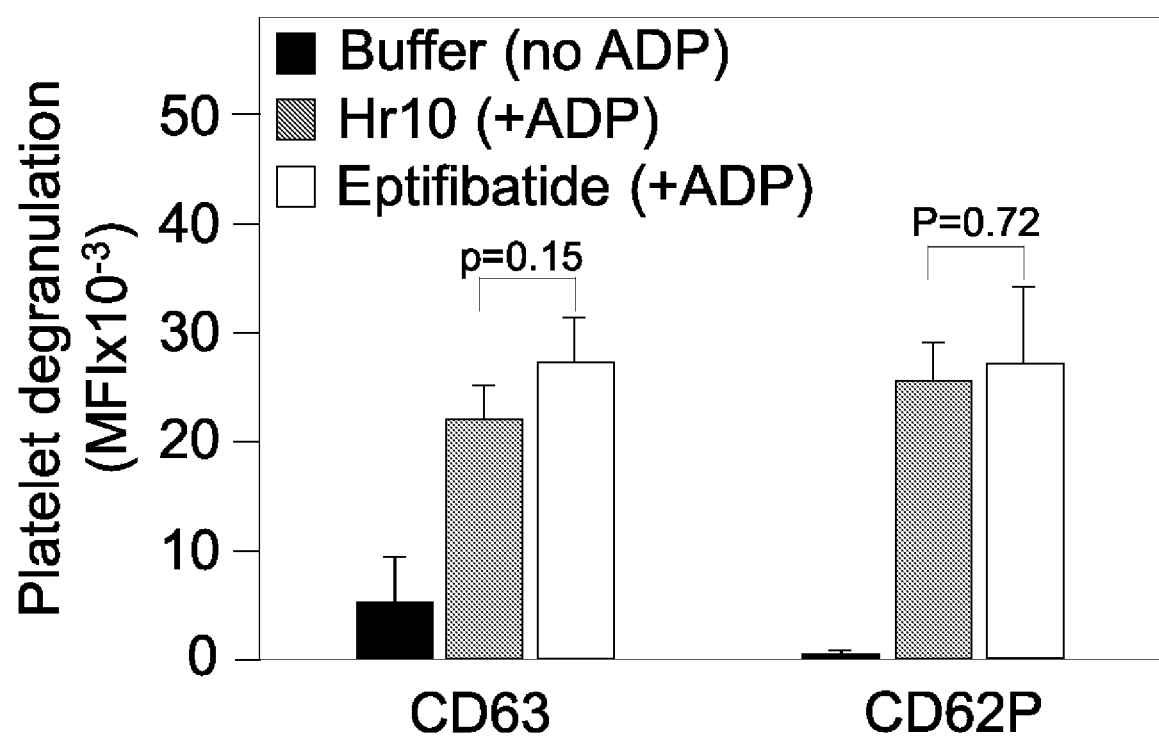

Hr10 blocked platelet aggregation induced by the agonists collagen, ADP and TRAP as effectively as eptifibatide, as shown in FIGS. 11A-11D. The adenine nucleotides ADP and ATP are co-released from dense (δ-) granules during platelet activation, and interact with the platelet $P_2$ receptors to amplify ongoing platelet activation. Both Hr10 and eptifibatide (at 1.5 μM) inhibited ADP (20 μM)-induced ATP secretion from dense (δ-) granules in whole blood by 71 f 14% and 60±20%, respectively, as shown in FIG. 11E, but did not significantly alter ADP-induced secretion from human platelet α-granules (reported by CD62P expression) or from lysosomes (reported by CD63 expression), as shown in FIG. 11F, and as noted above for abciximab (see e.g., Massberg et al, *Am. Heart J.* 146, E19 (2003)) and tirofiban (see e.g., Klinkhardt et al, *Thromb. Res.* 97, 201-207 (2000)).

Example 10. Hr10 Preserves Thrombin-Induced Clot Retraction

The mechanism by which prevention of the agonist-induced conformational changes in αIIbβ3 by pure antagonists results in preservation of clot retraction is presently unknown. Clot retraction occurs in response to the binding of polymeric fibrin to αIIbβ3, thus linking the integrin to actomyosin (see e.g., Jenkins et al, *J. Biol. Chem.* 273, 13878-13885 (1998)). When compared with fibrinogen, polymeric fibrin binds αIIbβ3 with higher affinity (see e.g., Litvinov et al, *J. Biol. Chem.* 291, 7858-7867 (2016)). Without being bound by theory, one hypothesis is that high affinity of the partial agonists is necessary to block fibrin-αIIbβ3 interaction and hence clot retraction. This is unlikely since Hr10, as described herein, and eptifibatide have comparable affinities in blocking soluble fibrinogen binding to activated αIIbβ3 and agonist-induced platelet aggregation. Preservation of clot retraction by the pure antagonists could not be explained either by a weaker affinity to inactive αIIbβ3 (see e.g., Mousa et al, *Arterioscler. Thromb. Vasc. Biol.* 20, 1162-1167 (2000)) since affinities of the pure antagonists to inactive and active αIIbβ3 are similar. A recent study showed that fibrin binds αIIbβ3 even when all the RGD motifs in fibrin are deleted (see e.g., Litvinov et al, *J. Biol. Chem.* 291, 7858-7867 (2016)) reflecting presence of MIDAS-independent fibrin binding sites, localized recently to the αIIb propeller domain (see e.g., Podolnikova et al, *J. Biol. Chem.* 289, 2371-2383 (2014). Since αIIbβ3 on non-activated platelets binds surface-immobilized fibrin (see e.g., Savage et al, *J. Biol. Chem.* 266, 11227-11233 (1991); and Hamaguchi et al, *Blood* 81, 2348-2356 (1993), it is expected to also do so when occupied by Hr10 or M-tirofiban, as described herein. It has been shown that αIIbβ3-dependent fibrin clot retraction kinetics correlates with intracellular protein tyrosine dephosphorylation, which is inhibited by binding of eptifibatide or abciximab to αIIbβ3 (see e.g., Osdoit et al, *J. Biol. Chem.* 276, 6703-6710 (2001)). It is believed that the availability of the pure orthosteric inhibitors of αIIbβ3 provide a tool to analyze the mechanisms linking integrin conformation to clot retraction, as is described herein.

Figure 12A:
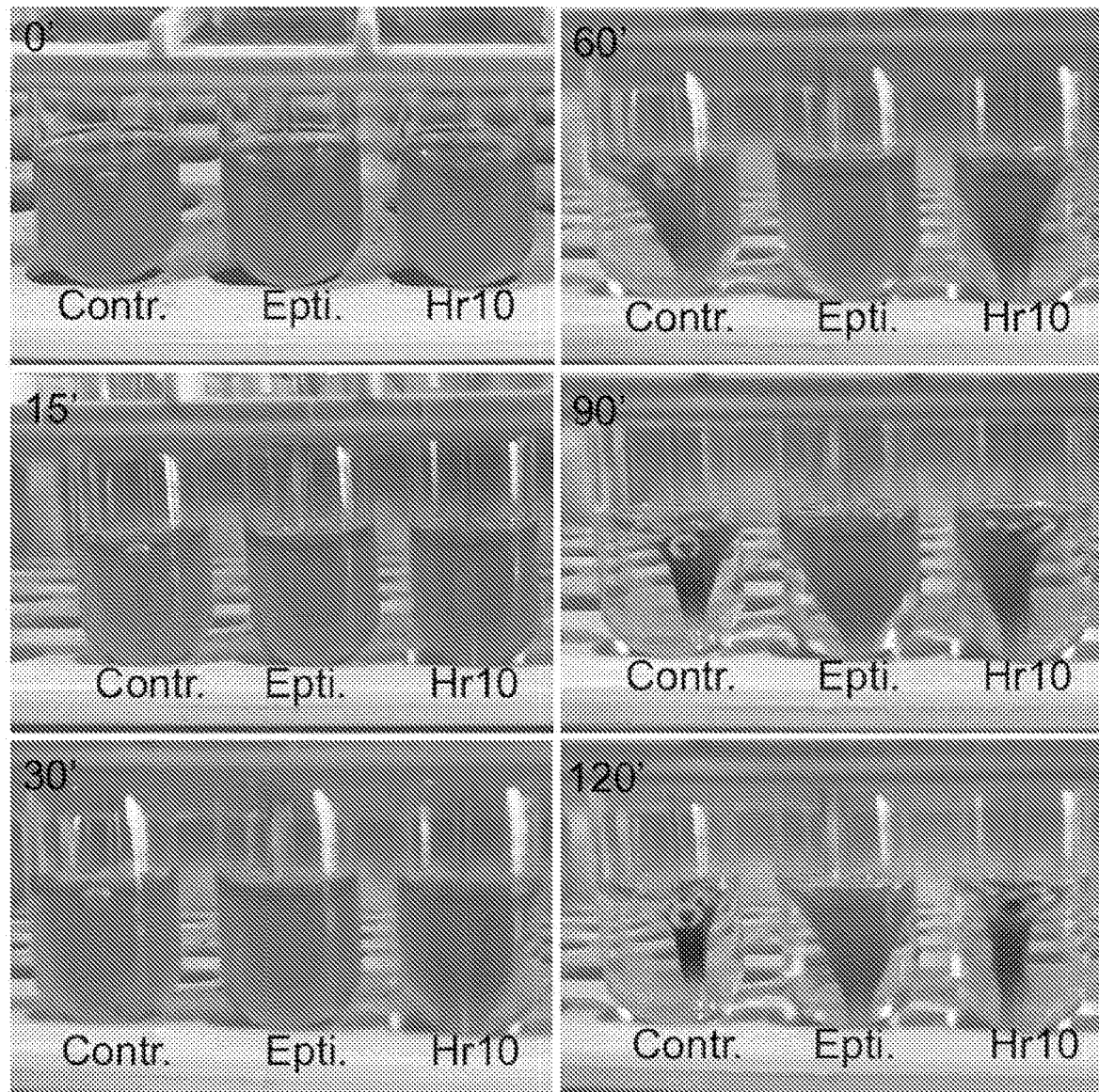
FIG. 12A shows representative kinetics of clot retraction in the absence (Contr.) and presence of Hr10 or eptifibatide (Epti.). Clot retraction took place around a central glass rod. 5 µL of red blood cells were added per 1 mL reaction to enhance the color contrast for photography. Photographs shown were taken at 0, 15, 30, 60, 90 and 120 minutes after addition of thrombin.
Figure 12B:
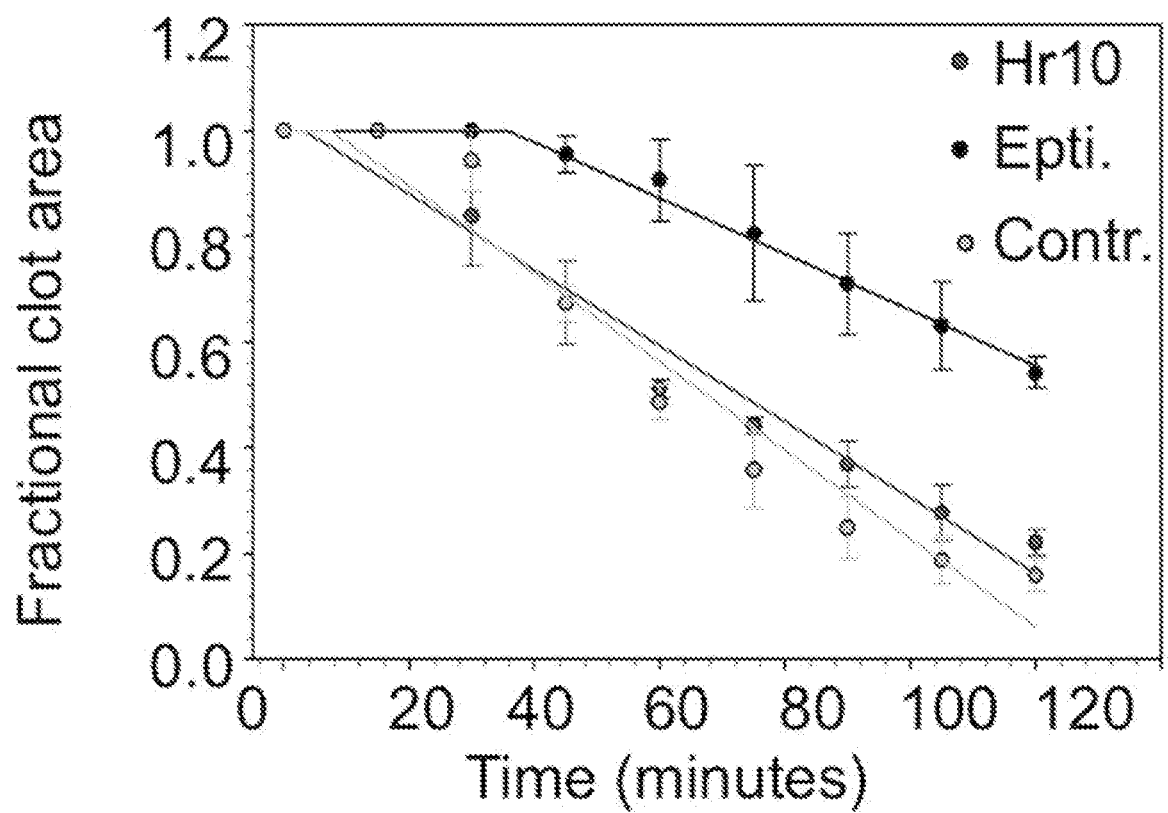
FIG. 12B shows time course (mean±S.E.) from three clot retraction experiments (including the experiment illustrated in FIG. 11A. The plot shows the fractional area occupied by the clot at 15-minute intervals with a linear regression through the points. No significant differences (p=0.125) were found in kinetics of clot retraction in buffer vs. Hr10. A lag period is noted with eptifibatide and clot retraction was significantly reduced vs buffer (p=4.5×10$^{-15}$).
Figure 12C:
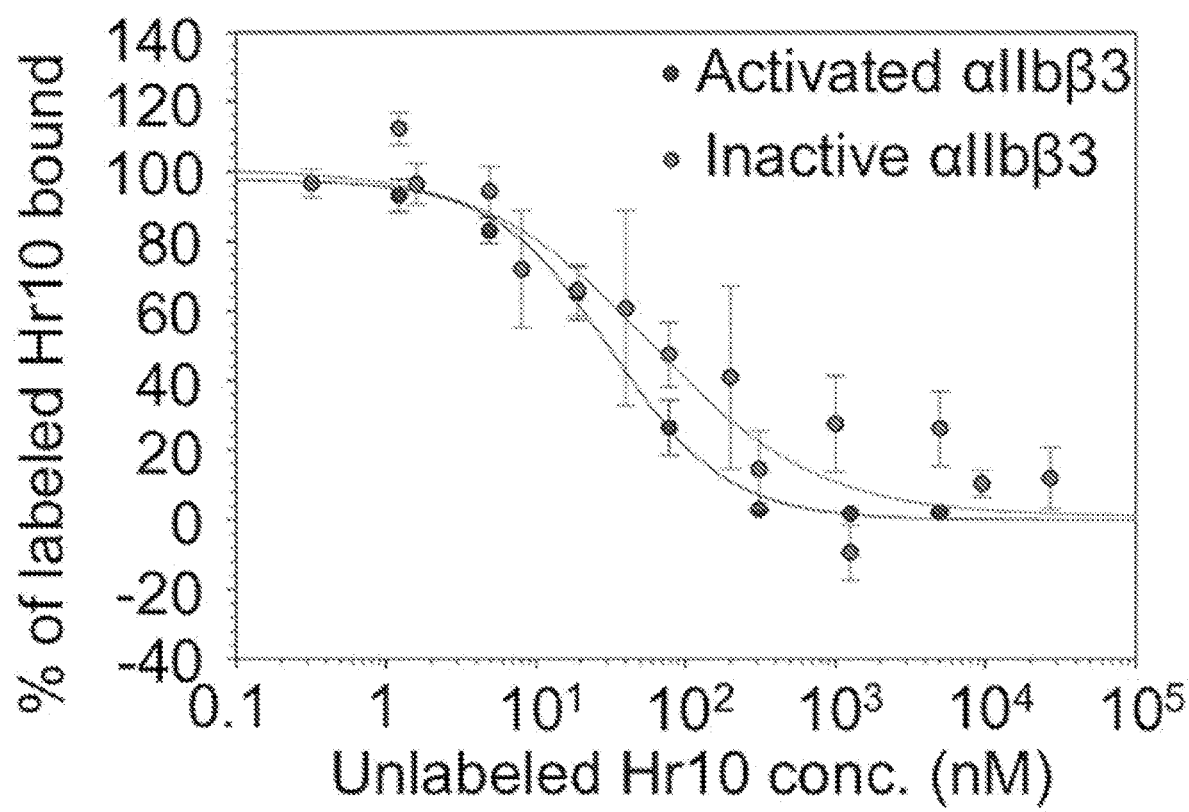
FIG. 12C shows dose response curves comparing displacement of Alexa488-labeled Hr10 binding to inactive and PT-25-activated αIIbβ3 on K562 cells by increasing concentrations of unlabeled Hr10. Cell binding was analyzed by FACS. The mean fluorescence intensity values for individual Hr10 experiments (four independent experiments and 6 determinations) were initially fit with a binding curve to determine minimum and maximum MFI values to use in scaling the data. The points and error bars indicate the mean and standard error for the scaled data. The red and black lines are a least squares fit to the averages. No differences were found (p=0.54).

Clot retraction normally helps secure hemostasis in vivo as evidenced by increased bleeding in mice with impaired clot retraction (see e.g., Leon et al, *Blood* 110, 3183-3191, doi:10.1182/blood-2007-03-080184 (2007)), or in recipients of any of the three anti-αIIbβ3 drugs (see e.g., Tutwiler et al, *Biophys. J.* 112, 714-723 (2017); Osdoit et al, *J. Biol. Chem.* 276, 6703-6710 (2001); Haling et al, *Blood* 117, 1719-1722 (2011)). The effects of Hr10 and eptifibatide on thrombin-induced clot retraction in fresh human platelet-rich plasma (PRP) (see e.g., Tucker et al, *Methods Mol. Biol.* 788, 101-107 (2012)) were compared. The kinetics of clot retraction were determined from quantification of serial images of the reaction acquired every 15 minutes for the 2-hour duration of the assay. As shown in FIGS. 12A-12B, Hr10 did not inhibit clot retraction vs. buffer alone (p=0.125). In contrast, eptifibatide significantly blocked clot retraction vs. buffer (p=4.5×10$^{-5}$), as previously shown (see e.g., Osdoit et al, *J. Biol. Chem.* 276, 6703-6710 (2001); and Shen et al Nature, 503, 131-135 (2013)). It has been reported that that αIIbβ3 antagonists that block platelet aggregation but not clot retraction exhibit affinities to inactive αIIbβ3 that are 2-3 logs lower than those to the active integrin (see e.g., Hantgan et al, *Thromb. Res.* 89, 271-279 (1998). This was not the case with Hr10, however, as its binding to inactive αIIbβ3 (IC$_{50}$=58.8±24.1 nM) was not significantly different from that to active αIIbβ3 (IC$_{50}$ 35.2±5.7 nM, n=3 experiments; p=0.54) (see FIG. 12C), and are also comparable to the affinity of eptifibatide to αIIbβ3 on resting platelets (k$_D$=120 nM) (see e.g., Schror & Weber *J. Thromb. Thrombolysis*, 15, 71-80 (2003).

Figure 13A:
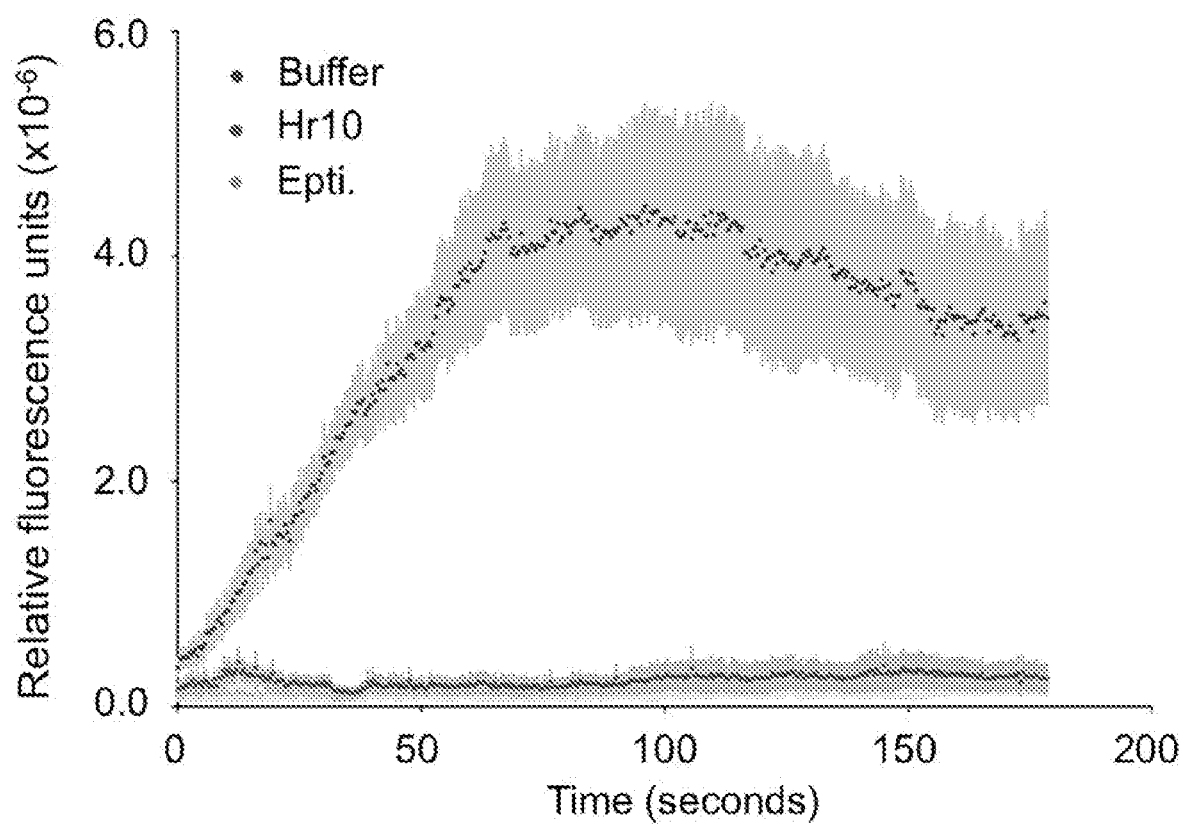
FIG. 13A shows graphs showing kinetics (mean±S.E., n=4 mice with laser-induced injuries at 8 different sites made in each) of human platelet accumulation at nascent injuries during infusion of buffer (PBS) or equimolar amounts of Hr10 or eptifibatide. n=4 animals per arm. There was no significant difference in human platelet accumulation in thrombi, between Hr10- and eptifibatide-treated mice at each time point.
Figure 13B:
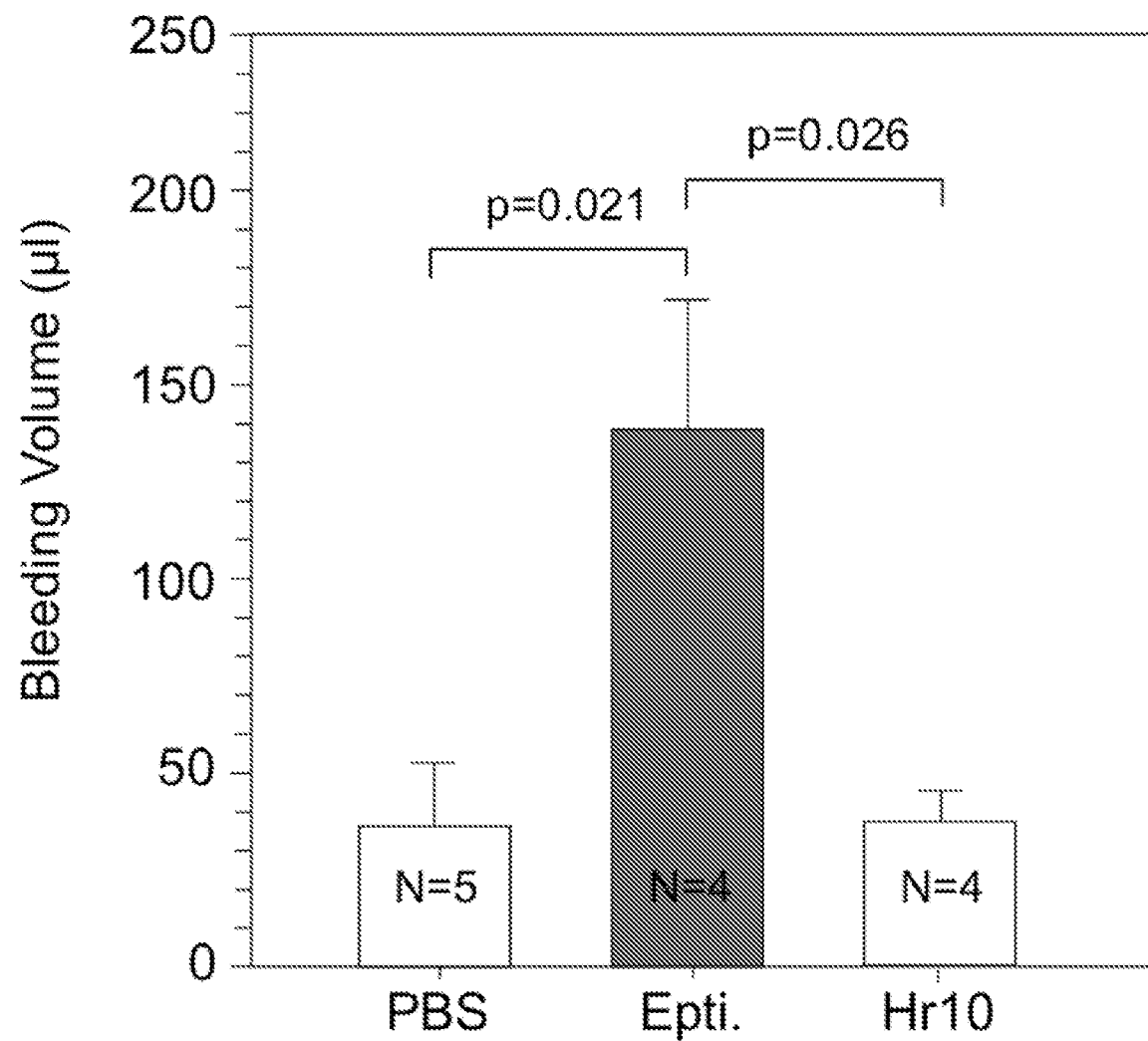
FIG. 13B shows histograms (mean±S.E.) showing baseline bleeding volume in vWF$^{RH\ RH}$NSG mice infused with human platelets before (PBS) or after administration of eptifibatide (Epti.) or Hr10. Epti. caused excessive bleeding (~10% of blood volume of a normal mouse). This was completely averted in presence of Hr10. p-values are indicated p=0.94 between PBS and Hr10 receiving mice). Other p-values are shown.

Example 11. Hr10 Blocks Microvascular Thrombosis without Increasing Bleeding in Humanized Mice To evaluate the effects of the peptides Hr10 and eptifibatide on nascent thrombus formation under flow, we induced thrombin-mediated arteriolar injury in a humanized mouse model that predicts clinical efficacy of anti-platelet agents (see e.g., Magallon et al, *Circulation*, 123, 319-326 (2011)). NSG (NOD-scid-IL-2Rγ$^{null}$) mice were made homozygous for human von Willebrand factor R$^{1326H}$ (vWF$^{RH/RH}$) (Id.), a substitution that switches binding of vWF from mouse to human glycoprotein (GP) Ib/IX, which accounts for the increased bleeding risk in these mice unless mice are infused with human platelets. To assess the effects of Hr10 and eptifibatide on bleeding, each inhibitor was given to mice infused with human platelets. Hr10 in equimolar concentrations to eptifibatide was as effective in completely preventing nascent occlusive thrombus formation at multiple sites of laser-induced arteriolar injury, as shown in FIG. 13A. Significantly, however, and in contrast to eptifibatide, Hr10 did not increase bleeding in the humanized vWF$^{RH}$ $^{RH}$NSG mice, as shown in FIG. 13B.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A polypeptide comprising a sequence having at least 99% sequence identity to the sequence of:

(SEQ ID NO: 1)
$R^1$-SDVPRDLEVVAATPTSLLISWDAPAVTVRYYRITYGETGGNSPVQEFT VPGSKSTATISGLKPGVDYTITVYAVTP(Har)GDWNEGGPISINYRT-$R^2$;

wherein:
   $R^1$ is absent or selected from the group consisting of a histidine tag, the human Fc fragment of IgG comprising a C-terminal histidine tag, an intervening spacer sequence, or a combination thereof, and
   $R^2$ is absent or GKKGK (SEQ ID NO: 6).

2. The polypeptide of claim 1, wherein $R^1$ is a histidine tag.

3. The polypeptide of claim 1, wherein the histidine tag comprises a polypeptide having at least 95% sequence identity to a polypeptide having the sequence ASHHHHHHLVPRGS (SEQ ID NO: 5).

4. The polypeptide of claim 1, wherein the histidine tag comprises a fluorescent small molecule.

5. The polypeptide of claim 1, wherein $R^1$ is absent.

6. The polypeptide of claim 1, wherein $R^2$ is GKKGK (SEQ ID NO: 6).

7. The polypeptide of claim 1, wherein $R^2$ is absent.

8. The polypeptide of claim 1, comprising the sequence of:

(SEQ ID NO: 7)
SDVPRDLEVVAATPTSLLISWDAPAVTVRYYRITYGETGGNSPVQEFTVPG SKSTATISGLKPGVDYTITVYAVTP(Har)GDWNEGGPISINYRT.

9. The polypeptide of claim 1, comprising the sequence of:

(SEQ ID NO: 8)
ASHHHHHHLVPRGSSDVPRDLEVVAATPTSLLISWDAPAVTVRYYRITYGE TGGNSPVQEFTVPGSKSTATISGLKPGVDYTITVYAVTP(Har)GDWNEGG PISINYRT.

10. The polypeptide of claim 1, comprising the sequence of:

(SEQ ID NO: 9)
ASHHHHHHLVPRGSSDVPRDLEVVAATPTSLLISWDAPAVTVRYYRITYGE

TGGNSPVQEFTVPGSKSTATISGLKPGVDYTITVYAVTP(Har)GDWNEGG

PISINYRTGKKGK.

11. A pharmaceutical composition comprising a polypeptide of claim 1 and a pharmaceutically acceptable carrier.

12. A method of treating a disease or disorder associated with abnormal expression or activity of one or more integrins in a subject, comprising administering to the subject a therapeutically effective amount of a polypeptide of claim 1.

13. The method of claim 12, wherein the integrin is selected from the group consisting of αVβ3, αIIbβ3, αvβ1, α4β1, α4β7, αvβ5, αvβ6, and αvβ8.

14. The method of claim 13, wherein the disease or disorder is selected from the group consisting of thrombosis, unstable angina, first myocardial infarction, recurrent myocardial infarction, ischemic sudden death, diastolic dysfunction, transient ischemic attack, stroke, atherosclerosis, venous thrombosis, deep vein thrombosis, thrombophlebitis, arterial embolism, coronary arterial thrombosis, cerebral arterial thrombosis, cerebral embolism, kidney embolism, pulmonary embolism, fibrosis, renal fibrosis, delayed graft function, diabetes, tumor angiogenesis, melanoma, cancer metastasis, diabetic nephropathy, diabetic retinopathy, neovascular glaucoma, restenosis, osteoporosis, multiple sclerosis, asthma, ulcerative colitis, skin burns, random flaps, blunt trauma, pitcher shoulder injury, and macular degeneration.

15. The method of claim 14, wherein the disease or disorder is thrombosis.

16. The method of claim 15, wherein the thrombosis is associated with abnormal activity of integrin αIIbβ3.

17. The method of claim 14, wherein the thrombosis is associated with abnormal expression of integrin αIIbβ3.

18. The method of claim 14, wherein the disease or disorder is fibrosis.

19. The method of claim 18, wherein the fibrosis is associated with abnormal activity of an integrin selected from the group consisting of integrin αvβ1, integrin αvβ3, integrin αvβ5, integrin αvβ6, and integrin αvβ8.

20. The method of claim 18, wherein the fibrosis is selected from the group consisting of liver fibrosis, lung fibrosis, and pancreatic fibrosis.

21. The method of claim 14, wherein the disease or disorder is multiple sclerosis.

22. The method of claim 21, wherein the multiple sclerosis is associated with abnormal activity of integrin α4β1.

23. The method of claim 14, wherein the disease or disorder is ulcerative colitis.

24. The method of claim 23, wherein the ulcerative colitis is associated with abnormal activity of integrin α4β7.

* * * * *

UNITED STATES PATENT AND TRADEMARK OFFICE
CERTIFICATE OF CORRECTION

PATENT NO. : 11,685,717 B2
APPLICATION NO. : 17/266339
DATED : June 27, 2023
INVENTOR(S) : M. Amin Arnaout It is certified that error appears in the above-identified patent and that said Letters Patent is hereby corrected as shown below:

In the Claims

In Column 73, Line 58 (approx.), Claim 1, delete "thereof," and insert -- thereof; --

Signed and Sealed this
Twenty-fourth Day of October, 2023

Katherine Kelly Vidal
*Director of the United States Patent and Trademark Office*

```
                              SEQUENCE LISTING

<160> NUMBER OF SEQ ID NOS: 31

<210> SEQ ID NO 1
<211> LENGTH: 94
<212> TYPE: PRT
<213> ORGANISM: Artificial
<220> FEATURE:
<223> OTHER INFORMATION: synthetic polypeptide that binds integrin
<220> FEATURE:
<221> NAME/KEY: MISC_FEATURE
<222> LOCATION: (1)..(1)
<223> OTHER INFORMATION: X is is absent or selected from the group
      consisting of a histidine tag, the human Fc fragment of IgG
      comprising a C-terminal histidine tag, an intervening spacer
      sequence, or a combination thereof
<220> FEATURE:
<221> NAME/KEY: MISC_FEATURE
<222> LOCATION: (78)..(78)
<223> OTHER INFORMATION: X = homoarginine
<220> FEATURE:
<221> NAME/KEY: MISC_FEATURE
<222> LOCATION: (94)..(94)
<223> OTHER INFORMATION: X is absent or SEQ ID No: 4 wherein X is absent
      or G

<400> SEQUENCE: 1

Xaa Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Val Thr Pro Xaa Gly Asp
65                  70                  75                  80

Trp Asn Glu Gly Gly Pro Ile Ser Ile Asn Tyr Arg Thr Xaa
                85                  90

<210> SEQ ID NO 2
<211> LENGTH: 94
<212> TYPE: PRT
<213> ORGANISM: Artificial
<220> FEATURE:
<223> OTHER INFORMATION: synthetic polypeptide that binds integrin
<220> FEATURE:
<221> NAME/KEY: MISC_FEATURE
<222> LOCATION: (1)..(1)
<223> OTHER INFORMATION: X is absent or selected from the group
      consisting of a histidine tag, the human Fc fragment of IgG
      comprising a C-terminal histidine tag, an intervening spacer
      sequence, or a combination thereof
<220> FEATURE:
<221> NAME/KEY: MISC_FEATURE
<222> LOCATION: (94)..(94)
<223> OTHER INFORMATION: X is absent or SEQ ID No: 4 wherein X is absent
      or G

<400> SEQUENCE: 2

Xaa Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
```

```
                        20                  25                  30

Arg Ile Thr Tyr Gly Glu Thr Gly Gly Asn Ser Pro Val Gln Glu Phe
                35                  40                  45

Thr Val Pro Gly Ser Lys Ser Thr Ala Thr Ile Ser Gly Leu Lys Pro
        50                  55                  60

Gly Val Asp Tyr Thr Ile Thr Val Tyr Ala Val Thr Pro Lys Gly Asp
65                  70                  75                  80

Trp Asn Glu Gly Gly Pro Ile Ser Ile Asn Tyr Arg Thr Xaa
                85                  90

<210> SEQ ID NO 3
<211> LENGTH: 94
<212> TYPE: PRT
<213> ORGANISM: Artificial
<220> FEATURE:
<223> OTHER INFORMATION: synthetic polypeptide that binds integrin
<220> FEATURE:
<221> NAME/KEY: MISC_FEATURE
<222> LOCATION: (1)..(1)
<223> OTHER INFORMATION: X is absent or selected from the group
      consisting of a histidine tag, the human Fc fragment of IgG
      comprising a C-terminal histidine tag, an intervening spacer
      sequence, or a combination thereof
<220> FEATURE:
<221> NAME/KEY: MISC_FEATURE
<222> LOCATION: (94)..(94)
<223> OTHER INFORMATION: X is absent or SEQ ID NO: 4 wherein X is absent
      or G

<400> SEQUENCE: 3

Xaa Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
                20                  25                  30

Arg Ile Thr Tyr Gly Glu Thr Gly Gly Asn Ser Pro Val Gln Glu Phe
                35                  40                  45

Thr Val Pro Gly Ser Lys Ser Thr Ala Thr Ile Ser Gly Leu Lys Pro
        50                  55                  60

Gly Val Asp Tyr Thr Ile Thr Val Tyr Ala Val Thr Pro Arg Gly Asp
65                  70                  75                  80

Trp Asn Glu Gly Gly Pro Ile Ser Ile Asn Tyr Arg Thr Xaa
                85                  90

<210> SEQ ID NO 4
<211> LENGTH: 5
<212> TYPE: PRT
<213> ORGANISM: Artificial
<220> FEATURE:
<223> OTHER INFORMATION: synthetic polypeptide that binds integrin
<220> FEATURE:
<221> NAME/KEY: misc_feature
<222> LOCATION: (1)..(1)
<223> OTHER INFORMATION: Xaa is absent of Gly

<400> SEQUENCE: 4

Xaa Lys Lys Gly Lys
1               5

<210> SEQ ID NO 5
<211> LENGTH: 14
<212> TYPE: PRT
<213> ORGANISM: Artificial
<220> FEATURE:
<223> OTHER INFORMATION: synthetic polypeptide that binds integrin
```

```
<400> SEQUENCE: 5

Ala Ser His His His His His Leu Val Pro Arg Gly Ser
1               5                   10

<210> SEQ ID NO 6
<211> LENGTH: 5
<212> TYPE: PRT
<213> ORGANISM: Artificial
<220> FEATURE:
<223> OTHER INFORMATION: synthetic polypeptide that binds integrin

<400> SEQUENCE: 6

Gly Lys Lys Gly Lys
1               5

<210> SEQ ID NO 7
<211> LENGTH: 92
<212> TYPE: PRT
<213> ORGANISM: Artificial
<220> FEATURE:
<223> OTHER INFORMATION: synthetic polypeptide that binds integrin
<220> FEATURE:
<221> NAME/KEY: MISC_FEATURE
<222> LOCATION: (77)..(77)
<223> OTHER INFORMATION: X = homoarginine

<400> SEQUENCE: 7

Ser Asp Val Pro Arg Asp Leu Glu Val Val Ala Ala Thr Pro Thr Ser
1               5                   10                  15

Leu Leu Ile Ser Trp Asp Ala Pro Ala Val Thr Val Arg Tyr Tyr Arg
            20                  25                  30

Ile Thr Tyr Gly Glu Thr Gly Gly Asn Ser Pro Val Gln Glu Phe Thr
        35                  40                  45

Val Pro Gly Ser Lys Ser Thr Ala Thr Ile Ser Gly Leu Lys Pro Gly
    50                  55                  60

Val Asp Tyr Thr Ile Thr Val Tyr Ala Val Thr Pro Xaa Gly Asp Trp
65                  70                  75                  80

Asn Glu Gly Gly Pro Ile Ser Ile Asn Tyr Arg Thr
                85                  90

<210> SEQ ID NO 8
<211> LENGTH: 106
<212> TYPE: PRT
<213> ORGANISM: Artificial
<220> FEATURE:
<223> OTHER INFORMATION: synthetic polypeptide that binds integrin
<220> FEATURE:
<221> NAME/KEY: MISC_FEATURE
<222> LOCATION: (91)..(91)
<223> OTHER INFORMATION: X = homoarginine

<400> SEQUENCE: 8

Ala Ser His His His His His Leu Val Pro Arg Gly Ser Ser Asp
1               5                   10                  15

Val Pro Arg Asp Leu Glu Val Val Ala Ala Thr Pro Thr Ser Leu Leu
            20                  25                  30

Ile Ser Trp Asp Ala Pro Ala Val Thr Val Arg Tyr Tyr Arg Ile Thr
        35                  40                  45

Tyr Gly Glu Thr Gly Gly Asn Ser Pro Val Gln Glu Phe Thr Val Pro
    50                  55                  60

Gly Ser Lys Ser Thr Ala Thr Ile Ser Gly Leu Lys Pro Gly Val Asp
65                  70                  75                  80
```

```
Tyr Thr Ile Thr Val Tyr Ala Val Thr Pro Xaa Gly Asp Trp Asn Glu
                85                  90                  95

Gly Gly Pro Ile Ser Ile Asn Tyr Arg Thr
            100                 105
```

<210> SEQ ID NO 9
<211> LENGTH: 111
<212> TYPE: PRT
<213> ORGANISM: Artificial
<220> FEATURE:
<223> OTHER INFORMATION: synthetic polypeptide that binds integrin
<220> FEATURE:
<221> NAME/KEY: MISC_FEATURE
<222> LOCATION: (91)..(91)
<223> OTHER INFORMATION: X = homoarginine

<400> SEQUENCE: 9

```
Ala Ser His His His His His His Leu Val Pro Arg Gly Ser Ser Asp
1               5                   10                  15

Val Pro Arg Asp Leu Glu Val Val Ala Ala Thr Pro Thr Ser Leu Leu
            20                  25                  30

Ile Ser Trp Asp Ala Pro Ala Val Thr Val Arg Tyr Tyr Arg Ile Thr
        35                  40                  45

Tyr Gly Glu Thr Gly Gly Asn Ser Pro Val Gln Glu Phe Thr Val Pro
    50                  55                  60

Gly Ser Lys Ser Thr Ala Thr Ile Ser Gly Leu Lys Pro Gly Val Asp
65                  70                  75                  80

Tyr Thr Ile Thr Val Tyr Ala Val Thr Pro Xaa Gly Asp Trp Asn Glu
                85                  90                  95

Gly Gly Pro Ile Ser Ile Asn Tyr Arg Thr Gly Lys Lys Gly Lys
            100                 105                 110
```

<210> SEQ ID NO 10
<211> LENGTH: 92
<212> TYPE: PRT
<213> ORGANISM: Artificial
<220> FEATURE:
<223> OTHER INFORMATION: synthetic polypeptide that binds integrin

<400> SEQUENCE: 10

```
Ser Asp Val Pro Arg Asp Leu Glu Val Val Ala Ala Thr Pro Thr Ser
1               5                   10                  15

Leu Leu Ile Ser Trp Asp Ala Pro Ala Val Thr Val Arg Tyr Tyr Arg
            20                  25                  30

Ile Thr Tyr Gly Glu Thr Gly Gly Asn Ser Pro Val Gln Glu Phe Thr
        35                  40                  45

Val Pro Gly Ser Lys Ser Thr Ala Thr Ile Ser Gly Leu Lys Pro Gly
    50                  55                  60

Val Asp Tyr Thr Ile Thr Val Tyr Ala Val Thr Pro Lys Gly Asp Trp
65                  70                  75                  80

Asn Glu Gly Gly Pro Ile Ser Ile Asn Tyr Arg Thr
                85                  90
```

<210> SEQ ID NO 11
<211> LENGTH: 92
<212> TYPE: PRT
<213> ORGANISM: Artificial
<220> FEATURE:
<223> OTHER INFORMATION: synthetic polypeptide that binds integrin

<400> SEQUENCE: 11

```
Ser Asp Val Pro Arg Asp Leu Glu Val Val Ala Ala Thr Pro Thr Ser
1               5                   10                  15

Leu Leu Ile Ser Trp Asp Ala Pro Ala Val Thr Val Arg Tyr Tyr Arg
            20                  25                  30

Ile Thr Tyr Gly Glu Thr Gly Gly Asn Ser Pro Val Gln Glu Phe Thr
            35                  40                  45

Val Pro Gly Ser Lys Ser Thr Ala Thr Ile Ser Gly Leu Lys Pro Gly
    50                  55                  60

Val Asp Tyr Thr Ile Thr Val Tyr Ala Val Thr Pro Arg Gly Asp Trp
65                  70                  75                  80

Asn Glu Gly Gly Pro Ile Ser Ile Asn Tyr Arg Thr
                85                  90

<210> SEQ ID NO 12
<211> LENGTH: 20
<212> TYPE: DNA
<213> ORGANISM: Artificial
<220> FEATURE:
<223> OTHER INFORMATION: sgRNA target sequence

<400> SEQUENCE: 12
cttgagctca aggtaggcac                                           20

<210> SEQ ID NO 13
<211> LENGTH: 120
<212> TYPE: PRT
<213> ORGANISM: Artificial
<220> FEATURE:
<223> OTHER INFORMATION: synthetic polypeptide that binds integrin

<400> SEQUENCE: 13

Ala Cys Ala Thr Cys Thr Cys Thr Cys Ala Gly Ala Ala Gly Cys Gly
1               5                   10                  15

Cys Ala Thr Cys Cys Gly Cys Gly Thr Gly Gly Cys Ala Gly Thr Gly
            20                  25                  30

Gly Thr Ala Gly Ala Gly Thr Ala Cys Cys Ala Thr Gly Ala Thr Gly
            35                  40                  45

Gly Ala Thr Cys Cys Ala Thr Gly Cys Thr Thr Ala Thr Cys Thr Thr
    50                  55                  60

Thr Gly Ala Gly Cys Thr Cys Ala Ala Gly Gly Cys Cys Cys Gly Gly
65                  70                  75                  80

Ala Ala Gly Cys Gly Ala Cys Cys Thr Cys Ala Gly Ala Gly Cys
                85                  90                  95

Thr Thr Cys Gly Gly Cys Gly Cys Ala Thr Cys Ala Cys Cys Ala Gly
            100                 105                 110

Cys Cys Ala Gly Ala Thr Thr Ala
            115                 120

<210> SEQ ID NO 14
<211> LENGTH: 20
<212> TYPE: PRT
<213> ORGANISM: Artificial
<220> FEATURE:
<223> OTHER INFORMATION: primer sequence for PCR genotyping

<400> SEQUENCE: 14

Thr Cys Ala Cys Thr Gly Thr Gly Ala Thr Gly Gly Thr Gly Thr Gly
1               5                   10                  15

Ala Ala Cys Cys
            20
```

<210> SEQ ID NO 15
<211> LENGTH: 19
<212> TYPE: PRT
<213> ORGANISM: Artificial
<220> FEATURE:
<223> OTHER INFORMATION: primer sequence for PCR genotyping

<400> SEQUENCE: 15

Cys Thr Gly Ala Cys Thr Ala Thr Cys Thr Cys Ala Thr Cys Thr Cys
1               5                   10                  15

Thr Thr Cys

<210> SEQ ID NO 16
<211> LENGTH: 238
<212> TYPE: PRT
<213> ORGANISM: Homo sapiens

<400> SEQUENCE: 16

Gly Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Ala Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys His His His His His His
225                 230                 235

<210> SEQ ID NO 17
<211> LENGTH: 88
<212> TYPE: PRT
<213> ORGANISM: Artificial
<220> FEATURE:
<223> OTHER INFORMATION: synthetic polypeptide for identifying the pure
      integrin antagonist
<220> FEATURE:
<221> NAME/KEY: MISC_FEATURE
<222> LOCATION: (76)..(76)
<223> OTHER INFORMATION: X can be any of SEQ ID NOs: 19, 20, 21, 22

<400> SEQUENCE: 17

Gly Ser Ser Asp Val Pro Arg Asp Leu Glu Val Val Ala Ala Thr Pro
1               5                   10                  15

Thr Ser Leu Leu Ile Ser Trp Asp Ala Pro Ala Val Thr Val Arg Tyr
            20                  25                  30

Tyr Arg Ile Thr Tyr Gly Glu Thr Gly Gly Asn Ser Pro Val Gln Glu
        35                  40                  45

Phe Thr Val Pro Gly Ser Lys Ser Thr Ala Thr Ile Ser Gly Leu Lys
    50                  55                  60

Pro Gly Val Asp Tyr Thr Ile Thr Val Tyr Ala Xaa Ile Ser Ile Asn
65                  70                  75                  80

Tyr Arg Thr Gly Lys Lys Gly Lys
                85

<210> SEQ ID NO 18
<211> LENGTH: 13
<212> TYPE: PRT
<213> ORGANISM: Artificial
<220> FEATURE:
<223> OTHER INFORMATION: synthetic polypeptide for identifying the pure
      integrin antagonist
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be Arg, Ile and Leu
<220> FEATURE:
<221> NAME/KEY: misc_feature
<222> LOCATION: (5)..(5)
<223> OTHER INFORMATION: Xaa can be Gly and Asp
<220> FEATURE:
<221> NAME/KEY: misc_feature
<222> LOCATION: (6)..(6)
<223> OTHER INFORMATION: Xaa can be Asp, Ser and Thr
<220> FEATURE:
<221> NAME/KEY: misc_feature
<222> LOCATION: (7)..(7)
<223> OTHER INFORMATION: Xaa can be Leu and Trp
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be can be Leu and Ile
<220> FEATURE:
<221> NAME/KEY: misc_feature
<222> LOCATION: (11)..(13)
<223> OTHER INFORMATION: Xaa can be any naturally occurring amino acid

<400> SEQUENCE: 18

Xaa Xaa Xaa Xaa Xaa Xaa Xaa Xaa Xaa Xaa Xaa Xaa Xaa
1               5                   10

<210> SEQ ID NO 19

```
<211> LENGTH: 13
<212> TYPE: PRT
<213> ORGANISM: Artificial
<220> FEATURE:
<223> OTHER INFORMATION: synthetic polypeptide for identifying the pure
      integrin antagonist
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be can be Leu and Ile
<220> FEATURE:
<221> NAME/KEY: misc_feature
<222> LOCATION: (11)..(13)
<223> OTHER INFORMATION: Xaa can be any naturally occurring amino acid

<400> SEQUENCE: 19

Xaa Xaa Xaa Arg Gly Asp Leu Xaa Xaa Xaa Xaa Xaa Xaa
1               5                   10

<210> SEQ ID NO 20
<211> LENGTH: 10
<212> TYPE: PRT
<213> ORGANISM: Artificial
<220> FEATURE:
<223> OTHER INFORMATION: synthetic polypeptide for identifying the pure
      integrin antagonist
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (8)..(10)
<223> OTHER INFORMATION: Xaa can be any naturally occurring amino acid

<400> SEQUENCE: 20

Xaa Xaa Xaa Arg Gly Asp Trp Xaa Xaa Xaa
1               5                   10

<210> SEQ ID NO 21
<211> LENGTH: 10
<212> TYPE: PRT
<213> ORGANISM: Artificial
<220> FEATURE:
<223> OTHER INFORMATION: synthetic polypeptide for identifying the pure
      integrin antagonist
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid
<220> FEATURE:
```

```
<221> NAME/KEY: misc_feature
<222> LOCATION: (8)..(10)
<223> OTHER INFORMATION: Xaa can be any naturally occurring amino acid

<400> SEQUENCE: 21

Xaa Xaa Xaa Arg Gly Asp Trp Xaa Xaa Xaa
1               5                   10

<210> SEQ ID NO 22
<211> LENGTH: 9
<212> TYPE: PRT
<213> ORGANISM: Artificial
<220> FEATURE:
<223> OTHER INFORMATION: synthetic polypeptide for identifying the pure
      integrin antagonist
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be Arg, Ile and Leu
<220> FEATURE:
<221> NAME/KEY: misc_feature
<222> LOCATION: (6)..(6)
<223> OTHER INFORMATION: Xaa can be Asp, Ser and Thr
<220> FEATURE:
<221> NAME/KEY: misc_feature
<222> LOCATION: (7)..(9)
<223> OTHER INFORMATION: Xaa can be any naturally occurring amino acid

<400> SEQUENCE: 22

Xaa Xaa Xaa Xaa Asp Xaa Xaa Xaa Xaa
1               5

<210> SEQ ID NO 23
<211> LENGTH: 13
<212> TYPE: PRT
<213> ORGANISM: Artificial
<220> FEATURE:
<223> OTHER INFORMATION: synthetic polypeptide for identifying the pure
      integrin antagonist
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid
<220> FEATURE:
<221> NAME/KEY: misc_feature
<222> LOCATION: (11)..(13)
<223> OTHER INFORMATION: Xaa can be any naturally occurring amino acid

<400> SEQUENCE: 23

Xaa Xaa Xaa Arg Gly Asp Leu Xaa Xaa Leu Xaa Xaa Xaa
1               5                   10

<210> SEQ ID NO 24
<211> LENGTH: 13
<212> TYPE: PRT
<213> ORGANISM: Artificial
<220> FEATURE:
```

```
<223> OTHER INFORMATION: synthetic polypeptide for identifying the pure
      integrin antagonist
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid
<220> FEATURE:
<221> NAME/KEY: misc_feature
<222> LOCATION: (11)..(13)
<223> OTHER INFORMATION: Xaa can be any naturally occurring amino acid

<400> SEQUENCE: 24

Xaa Xaa Xaa Arg Gly Asp Leu Xaa Xaa Ile Xaa Xaa Xaa
1               5                   10

<210> SEQ ID NO 25
<211> LENGTH: 9
<212> TYPE: PRT
<213> ORGANISM: Artificial
<220> FEATURE:
<223> OTHER INFORMATION: synthetic polypeptide for identifying the pure
      integrin antagonist
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (7)..(9)
<223> OTHER INFORMATION: Xaa can be any naturally occurring amino acid

<400> SEQUENCE: 25

Xaa Xaa Xaa Ile Asp Ser Xaa Xaa Xaa
1               5

<210> SEQ ID NO 26
<211> LENGTH: 9
<212> TYPE: PRT
<213> ORGANISM: Artificial
<220> FEATURE:
<223> OTHER INFORMATION: XXXIDTXXX
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (7)..(9)
<223> OTHER INFORMATION: Xaa can be any naturally occurring amino acid

<400> SEQUENCE: 26

Xaa Xaa Xaa Ile Asp Thr Xaa Xaa Xaa
1               5

<210> SEQ ID NO 27
<211> LENGTH: 9
<212> TYPE: PRT
```

```
<213> ORGANISM: Artificial
<220> FEATURE:
<223> OTHER INFORMATION: synthetic polypeptide for identifying the pure
      integrin antagonist
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (7)..(9)
<223> OTHER INFORMATION: Xaa can be any naturally occurring amino acid

<400> SEQUENCE: 27

Xaa Xaa Xaa Leu Asp Ser Xaa Xaa Xaa
1               5

<210> SEQ ID NO 28
<211> LENGTH: 9
<212> TYPE: PRT
<213> ORGANISM: Artificial
<220> FEATURE:
<223> OTHER INFORMATION: synthetic polypeptide for identifying the pure
      integrin antagonist
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (7)..(9)
<223> OTHER INFORMATION: Xaa can be any naturally occurring amino acid

<400> SEQUENCE: 28

Xaa Xaa Xaa Leu Asp Thr Xaa Xaa Xaa
1               5

<210> SEQ ID NO 29
<211> LENGTH: 91
<212> TYPE: PRT
<213> ORGANISM: Artificial
<220> FEATURE:
<223> OTHER INFORMATION: synthetic polypeptide for identifying the pure
      integrin antagonist
<220> FEATURE:
<221> NAME/KEY: MISC_FEATURE
<222> LOCATION: (76)..(76)
<223> OTHER INFORMATION: X can be any of SEQ ID NOs: 19, 20, 21, 22

<400> SEQUENCE: 29

Gly Ser Ser Asp Val Pro Arg Asp Leu Glu Val Val Ala Ala Thr Pro
1               5                   10                  15

Thr Ser Leu Leu Ile Ser Trp Asp Ala Pro Ala Val Thr Val Arg Tyr
            20                  25                  30

Tyr Arg Ile Thr Tyr Gly Glu Thr Gly Gly Asn Ser Pro Val Gln Glu
        35                  40                  45

Phe Thr Val Pro Gly Ser Lys Ser Thr Ala Thr Ile Ser Gly Leu Lys
    50                  55                  60

Pro Gly Val Asp Tyr Thr Ile Thr Val Tyr Ala Xaa Gly Gly Pro Ile
65                  70                  75                  80

Ser Ile Asn Tyr Arg Thr Gly Lys Lys Gly Lys
```

```
<210> SEQ ID NO 30
<211> LENGTH: 91
<212> TYPE: PRT
<213> ORGANISM: Artificial
<220> FEATURE:
<223> OTHER INFORMATION: polypeptide for identifying the pure integrin
      antagonist
<220> FEATURE:
<221> NAME/KEY: MISC_FEATURE
<222> LOCATION: (76)..(76)
<223> OTHER INFORMATION: X can be any of SEQ ID NOs: 19, 20, 21, 22

<400> SEQUENCE: 30

Gly Ser Ser Asp Val Pro Arg Asp Leu Glu Val Val Ala Ala Thr Pro
1               5                   10                  15

Thr Ser Leu Leu Ile Ser Trp Asp Ala Pro Ala Val Thr Val Arg Tyr
            20                  25                  30

Tyr Arg Ile Thr Tyr Gly Glu Thr Gly Gly Asn Ser Pro Val Gln Glu
        35                  40                  45

Phe Thr Val Pro Gly Ser Lys Ser Thr Ala Thr Ile Ser Gly Leu Lys
    50                  55                  60

Pro Gly Val Asp Tyr Thr Ile Thr Val Tyr Ala Xaa Gly Gly Pro Ile
65                  70                  75                  80

Ser Ile Asn Tyr Arg Thr Gly Lys Lys Gly Lys
                85                  90

<210> SEQ ID NO 31
<211> LENGTH: 4
<212> TYPE: PRT
<213> ORGANISM: Artificial Sequence
<220> FEATURE:
<223> OTHER INFORMATION: synthetic polypeptide that binds integrin

<400> SEQUENCE: 31

Lys Lys Gly Lys
1
```